US005693617A

United States Patent [19]
Stein et al.

[11] Patent Number: 5,693,617
[45] Date of Patent: Dec. 2, 1997

[54] INHIBITORS OF THE 26S PROTEOLYTIC COMPLEX AND THE 20S PROTEASOME CONTAINED THEREIN

[75] Inventors: Ross L. Stein, Sudbury; Yu-Ting Ma, Needham; Stephen Brand, Lincoln, all of Mass.

[73] Assignee: ProScript, Inc., Cambridge, Mass.

[21] Appl. No.: 404,866

[22] Filed: Jan. 15, 1995

Related U.S. Application Data

[63] Continuation-in-part of Ser. No. 212,909, Mar. 15, 1994, abandoned.

[51] Int. Cl.$^6$ .................. A61K 38/00; C07K 5/00; C07C 271/00; C07C 229/00
[52] U.S. Cl. ............... 514/18; 514/19; 530/331; 560/20; 560/27; 560/31; 560/32; 560/41; 560/47; 560/159
[58] Field of Search ................ 560/20, 27, 31, 560/32, 41, 47, 159; 530/331; 514/18, 19

[56] References Cited

U.S. PATENT DOCUMENTS

| | | | |
|---|---|---|---|
| 4,261,868 | 4/1981 | Hora et al. | 252/529 |
| 4,369,183 | 1/1983 | Jones et al. | 424/263 |
| 4,499,082 | 2/1985 | Shenvi et al. | 514/2 |
| 4,510,130 | 4/1985 | Platt et al. | 514/2 |
| 4,525,309 | 6/1985 | Matteson et al. | 260/462 |
| 4,537,707 | 8/1985 | Severson, Jr. | 252/545 |
| 4,537,773 | 8/1985 | Shenvi | 514/63 |
| 4,842,769 | 6/1989 | Shulman et al. | 252/8.6 |
| 4,963,655 | 10/1990 | Kinder et al. | 530/331 |
| 4,997,929 | 3/1991 | Collins et al. | 536/27 |
| 5,030,378 | 7/1991 | Venegas | 252/174.12 |
| 5,106,948 | 4/1992 | Kinder et al. | 530/331 |
| 5,169,841 | 12/1992 | Kleeman et al. | 514/63 |
| 5,187,157 | 2/1993 | Kettner et al. | 514/18 |
| 5,242,904 | 9/1993 | Kettner et al. | 514/18 |
| 5,250,720 | 10/1993 | Kettner et al. | 558/288 |
| 5,340,736 | 8/1994 | Goldberg et al. | 435/226 |

FOREIGN PATENT DOCUMENTS

| | | | |
|---|---|---|---|
| 0 145 441 | 6/1985 | European Pat. Off. | C07K 5/08 |
| 0 293 881 | 12/1988 | European Pat. Off. | C07K 5/00 |
| 0 315 574 | 5/1989 | European Pat. Off. | C07K 5/02 |
| 0 363 284 | 10/1989 | European Pat. Off. | C07K 5/02 |
| 0 364 344 | 10/1989 | European Pat. Off. | C07K 5/02 |
| 0 354 522 | 2/1990 | European Pat. Off. | A61K 37/64 |
| 0 393457 | 4/1990 | European Pat. Off. | C07K 5/06 |
| 0 471 651 | 2/1992 | European Pat. Off. | C07K 5/06 |
| 0 478 050 | 4/1992 | European Pat. Off. | C11D 3/386 |
| 0 381 262 | 8/1992 | European Pat. Off. | C11D 3/386 |
| 0 511 456 | 11/1992 | European Pat. Off. | C11D 3/386 |
| 0 583 536 | 2/1994 | European Pat. Off. | C11D 3/386 |
| 38 27 340 | 2/1990 | Germany | A61K 37/02 |
| 2 040 291 | 8/1980 | United Kingdom | C07C 103/52 |
| WO88/10266 | 12/1988 | WIPO | C07K 5/04 |
| WO 91/13904 | 9/1991 | WIPO | C07K 3/00 |
| WO 92/07869 | 5/1992 | WIPO | C07K 5/08 |
| WO 92/11850 | 7/1992 | WIPO | A61K 31/137 |
| WO 92/12140 | 7/1992 | WIPO | C07D 265/30 |
| WO 92/19707 | 11/1992 | WIPO | C11D 3/386 |
| WO 92/19709 | 11/1992 | WIPO | C11D 3/386 |
| WO 93/21213 | 10/1993 | WIPO | C07K 5/06 |
| WO 93/21214 | 10/1993 | WIPO | C07K 5/06 |
| WO 94/21668 | 9/1994 | WIPO | C07K 1/08 |
| WO 95/09858 | 4/1995 | WIPO | C07F 5/02 |

OTHER PUBLICATIONS

Angelastro et al., "α–Diketone and α–Keto Ester Derivatives of N–Protected Amino Acids and Peptides as Novel Inhibitors of Cysteine and Serine Proteinases," *J. Med. Chem.* 33(1):11–13 (1990).

Angliker et al., "The Synthesis of Lysylfluoromethanes and Their Properties as Inhibitors of Trypsin, Plasmin and Cathepsin B," *Biochem. J.* 241:871–875 (1987).

Aoyagi et al., "Structures and Activities of Protease Inhibitors of Microbial Origin," in: *Proteases and Biological Control*, Cold Spring Harbor, NY: Cold Spring Harbor Laboratory Press, pp. 429–454 (1975).

Bachmair et al., "In Vivo Half–Life of a Protein Is a Function of Its Amino–Terminal Residue," *Science* 234:179–186 (1986).

Badalamente et al., "Neuromuscular Recovery Using Calcium Protease Inhibition After Median Nerve Repair in Primates," *Proc. Natl. Acad. Sci. USA* 86:5983–5987 (1989).

Boches et al., "Role for the Adenosine Triphosphate–Dependent Proteolytic Pathway in Reticulocyte Maturation," *Science* 215:978–980 (1982).

Brown, H.C., and Gupta, S.K., "The Facile Redistribution of Trialkylboranes with Trimethylene Borate. A Simple, General Synthesis of Alkaneboronic Esters and Acids from Olefins via Hydroboration," *J. Am. Chem. Soc.* 92:6983–6984 (1970).

Brown, H.C., and Gupta, S.K., "1,3,2–Benzodioxaborole, a Convenient Monofunctional Hydroborating Agent. A Simple New Synthesis of Alkaneboronic Esters and Acids from Olefins via Hydroboration," *J. Am. Chem. Soc.* 93:1816–1818 (1971).

Brown et al., "Structural and Serological Similarity of MHC–linked LMP and Proteasome (Multicatalytic Proteinase) Complexes," *Nature* 353:355–357 (1991).

Carbone et al., "Class I–Restricted Processing and Presentation of Exogenous Cell–Associated Antigen In Vivo," *J. Exp. Med.* 171:377–387 (1990).

Ciechanover et al., "Ubiquitin Dependence of Selective Protein Degradation Demonstrated in the Mammalian Cell Cycle Mutant ts85," *Cell* 37(1):57–66 (1984).

Dick et al., "Degradation of Oxidized Insulin B Chain by the Multiproteinase Complex Macropain (Proteasome)," *Biochemistry* 30:2725–2734 (1991).

(List continued on next page.)

*Primary Examiner*—Jerry D. Johnson
*Attorney, Agent, or Firm*—Sterne, Kessler, Goldstein & Fox, P.L.L.C.

[57] ABSTRACT

Disclosed herein is a method for reducing the rate of degradation of proteins in an animal comprising contacting cells of the animal with certain proteasome inhibitors. The structure of the inhibitors are also disclosed.

22 Claims, 8 Drawing Sheets

OTHER PUBLICATIONS

Donehower et al., "Mice Deficient for p53 are Developmentally Normal but Susceptible to Spontaneous Tumours," *Nature* 356:215–221 (1992).

Driscoll et al., "A Controlled Breakdown: Antigen Processing and the Turnover of Viral Proteins," *Cell* 68:823–825 (1992).

Driscoll et al., "The Proteasome (Multicatalytic Protease) Is a Component of the 1500–kDa Proteolytic Complex Which Degrades Ubiquitin–Conjugated Proteins," *J. Biol. Chem.* 265(9):4789–4792 (1990).

Dubiel et al., "Purification of a 11S Regulator of the Multicatalytic Protease," *J. Biol. Chem.* 267(31):22369–22377 (1992).

Ewoldt et al., "Sulfonyl Fluoride Serine Protease Inhibitors Inactivate RNK–16 Lymphocyte Granule Proteases and Reduce Lysis by Granule Extracts and Perforin," *Molec. Immunol.* 29(6):713–721 (1992).

Eytan et al., "ATP–dependent Incorporation of 20S Protease into the 26S Complex That Degrades Proteins Conjugated to Ubiquitin," *Proc. Natl. Acad. Sci. USA* 86:7751–7755 (1989).

Fehrentz et al., "An Efficient Synthesis of Optically Active α–(t–Butoxycarbonylamino)–aldehydes From α–Amino Acids," *Synthesis*, pp.676–678 (1983).

Fehrentz et al., "Synthesis of Aldehydic Peptides Inhibiting Renin," *Int. J. Peptide Protein Res.* 26:236–241 (1985).

Furuno et al., "Role of Different Proteolytic Systems in the Degradation of Muscle Proteins during Denervation Atrophy," *J. Biol. Chem.* 265(15):8550–8557 (1990).

Ganoth et al., "A Multicomponent System That Degrades Proteins Conjugated to Ubiquitin," *J. Biol. Chem.* 263 (25):12412–12419 (1988).

Glynne et al., "A Proteasome–Related Gene Between the Two ABC Transporter Loci in the Class II Region of the Human MHC," *Nature* 353:357–360 (1991).

Goldberg, A.L., "The Mechanism and Functions of ATP––dependent Proteases in Bacterial and Animal Cells," *Eur. J. Biochem.* 203:9–23 (1992).

Goldberg et al., "Proteolysis, Proteasomes and Antigen Presentation," *Nature* 357:375–379 (1992).

Gonda et al., "Universality and Structure of the N–end Rule," *J. Biol. Chem.* 264(28):16700–16712 (1989).

Green et al., "Peptidyl Diazomethyl Ketones Are Specific Inactivators of Thiol Proteinases," *J. Biol. Chem.* 256(4):1923–1928 (1981).

Gronostajski et al., "The ATP Dependence of the Degradation of Short– and Long–Lived Proteins in Growing Fibroblasts," *J. Biol Chem.* 260(6):3344–3349 (1985).

Hall et al., "High Levels of p53 Protein in UV–irradiated Normal Human Skin," *Oncogene* 8:203–207 (1993).

Hanada et al., "Characterization of the Three New Analogs of E–64 and Their Therapeutic Application," *in: Proteinase Inhibitors: Medical and Biological Aspects,* Katunuma et al. (eds.), New York: Springer–Verlag Publishers, pp. 25–36 (1983).

Hayashi et al., "Activation of Intracellular Calcium–Activated Neutral Proteinase in Erythrocytes and Its Inhibition by Exogenously Added Inhibitors," *Biochim. Biophys. Acta* 1094:249–256 (1991).

Hernandez et al., "Effect of the 7–Amino Substituent on the Inhibitory Potency of Mechanism–Based Isocoumarin Inhibitors for Porcine Pancreatic and Human Neutrophil Elastases," *J. Med. Chem.* 35:1121–1129 (1992).

Hershko et al., "The Ubiquitin System For Protein Degradation," *Annu. Rev. Biochem.* 61:761–807 (1992).

Hiwasa et al., "Cysteine Proteinase Inhibitors and Ras Gene Products Share the Same Biological Activities Including Transforming Activity Toward NIH3T3 Mouse Fibroblasts and the Differentiation–Inducing Activity Toward PC12 Rat Pheochromocytoma Cells," *Carcinogenesis* 11(1):75–80 (1990).

Hough et al., "Purification of Two High Molecular Weight Proteases from Rabbit Reticulocyte Lysate," *J. Biol. Chem.* 262(17):8303–8313 (1987).

Hudig et al., "The Function of Lymphocyte Proteases," *J. Immunol.* 147(4):1360–1368 (1991).

Hudig et al., "Selective Isocoumarin Serine Protease Inhibitors Block RNK–16 Lymphocyte Granule–Mediated Cytolysis," *Molec. Immunol.* 26(8):793–798 (1989).

Inoue et al., "Inhibition of Degradation of 3–Hydroxy–3–methylglutaryl–coenzyme A Reductase in Vivo by Cysteine Protease Inhibitors," *J. Biol. Chem.* 266(20):13311–13317 (1991).

Ito et al., "The Synthesis and Properties of Tripeptide Aldehydes Having Neurite–Extension Activity," *Chem. Abstr.* 118:885, Abstract No. 148014h (1992).

Kajiwara et al., "Elucidation of Calpain Dependent Phosphorylation of Myosin Light Chain Human Platelets," *Biochemi. Int.* 15 (5):935–944 (1987).

Kam et al., "Mechanism–Based Isocoumarin Inhibitors for Trypsin and Blood Coagulation Serine Proteases: New Anticoagulants," *Biochemistry* 27:2547–2557 (1988).

Kam et al., "Thioester Chromogenic Substrates for Human Factor VIIa: Substituted Isocoumarins Are Inhibitors of Factor VIIa and In Vitro Anticoagulants," *Thrombosis and Haemostasis* 64 (1):133–137 (1990).

Kastan et al., "A Mammalian Cell Cycle Checkpoint Pathway Utilizing p53 and GADD45 Is Defective in Ataxia–Telangiectasia," *Cell* 71:587–597 (1992).

Kastan et al., "Participation of p53 Protein in the Cellular Response to DNA Damage," *Cancer Res.* 51:6304–6311 (1991).

Kelly et al., "Second Proteasome–Related Gene in the Human MHC class II Region," *Nature* 353:667–668 (1991).

Kennedy et al., "Mechanism of Association of a Specific Aldehyde 'Transition–State Analogue' to the Active Site of α–Chymotrypsin," *Biochemistry* 18 (2):349–356 (1979).

Kettelhut et al., "Endocrine Regulation of Protein Breakdown in Skeletal Muscle," *Diabetes/Metabolism Rev.* 4(8):751–772 (1988).

Kuerbitz et al., "Wild–type p53 Is a Cell Cycle Checkpoint Determinant Following Irradiation," *Proc. Natl. Acad. Sci. USA* 89:7491–7495 (1992).

Lane, D.P., "p53, Guardian of the Genome," *Nature* 358:15–16 (1992).

Li et al., "Isolation and Characterization of a Novel Endogenous Inhibitor of the Proteasome," *Biochemistry* 30:9709–9715 (1991).

Lowell et al., "Evidence That Lysosomes Are Not Involved in the Degradation of Myofibrillar Proteins in Rat Skeletal Muscle," *Biochem. J.* 234:237–240 (1986).

Luca et al., "Control of Programmed Cyclin Destruction in a Cell–free System," *J. Cell Biol.* 109:1895–1909 (1989).

Maltzman et al., "UV Irradiation Stimulates Levels of p53 Cellular Tumor Antigen in Nontransformed Mouse Cells," *Molec. and Cell. Biol.* 4(9):1689–1694 (1984).

Martinez et al., "Homology of Proteasome Subunits to a Major Histocompatibility Complex-Linked LMP Gene," *Nature* 353:664–666 (1991).

Matteson, D.S., and Majumdar, D., "α–Chloro Boronic Esters from Homologation of Boronic Esters," *J. Am. Chem. Soc.* 102:7588–7590 (1980).

Matteson, D.S., and Ray, R., "Directed Chiral Synthesis with Pinanediol Boronic Esters," *J. Am. Chem. Soc.* 102:7590–7591 (1980).

Matteson, D.S., et al., "(R)–1–Acetamido–2–phenylethaneboronic Acid. A Specific Transition–State Analogue for Chymotrypsin," *J. Am. Chem.* Soc. 103:5241–5242 (1981).

Matteson, D.S., and Arne, K.H., "Carbanions from α–Phenylthio Boronic Esters as Synthetic Intermediates," *Organometallics* 1:280–288 (1982).

Matteson, D.S., and Erdik, E., "Epimerization of α–Chloro Boronic Esters by Lithium and Zinc Chlorides," *Organometallics* 2:1083–1088 (1983).

Matteson, D.S., and Majumdar, D., "α–Trimethylsilyl Boronic Esters. Pinacol Lithio(trimethylsilyl-)methaneboronate, Homologation of Boronic Esters with [Chloro(trimethylsilyl)methyl]lithium, and Comparisons with Some Phosphorus and Sulfur Analogues," *Organometallics* 2:230–236 (1983).

Matteson, D.S., and Majumdar, D., "Homologation of Boronic Estes to αChloro Boronic Esters," *Organometallics* 2:1529–1535 (1983).

Matteson, D.S., et al., "Directed Chiral Synthesis by Way of α–Chloro Boronic Esters," *Organometallics* 2:1536–1543 (1983).

Matteson, D.S., and Sadhu, K.M., "Boronic Ester Homologation with 99% Chiral Selectivity and Its Use in Syntheses of the Insect Pheromones (3S,4S)–4–Methyl–3–heptanol and exo–Brevicomin," *J. Am. Chem. Soc.* 105:2077–2078 (1983).

Matthews et al., "Involvement of the Proteasome in Various Degradative Processes in Mammalian Cells," *Proc. Natl. Acad. Sci. USA* 86(8):2597–2601 (1989).

McGuire et al., "An Enzyme Related to the High Molecular Weight Multicatalytic Proteinase, Macropain, Participates in a Ubiquitin–Mediated, ATP–stimulated Proteolytic Pathway in Soluble Extracts of BHK 21/C13 Fibroblasts," *Biochim. et Biophys. Acta* 967:195–203 (1988).

Michalek et al., "A Role for the Ubiquitin–Dependent Proteolytic Pathway in MHC Class I–Restricted Antigen Presentation," *Nature* 363:552–554 (1993).

Monaco et al., "Identification of a Fourth Class of Proteins Linked to the Murine Major Histocompatibility Complex," *Proc. Natl. Acad. Sci. USA* 79:3001–3005 (1982).

Monaco et al., "The LMP Antigens: A Stable MHC–Controlled Multisubunit Protein Complex," *Human Immunol.* 15:416–426 (1986).

Monaco, J.J., "A Molecular Model of MHC Class–I–R-estricted Antigen Processing," *Immunol. Today* 13:173–179 (1992).

Moore et al., "Introduction of Soluble Protein Into the Class I Pathway of Antigen Processing and Presentation," *Cell* 54:777–785 (1988).

Morrison et al., "Differences in Antigen Presentation to MHC Class I– and Class II–Restricted Influenza Virus–Specific Cytolytic T Lymphocyte Clones," *J. Exp. Med.* 163:903–921 (1986).

Murakami et al., "Endogenous Inhibitor of Nonlysosomal High Molecular Weight Protease and Calcium–Dependent Protease," *Proc. Natl. Acad. Sci. USA* 83:7588–7592 (1986).

Odake et al., "Human and Murine Cytotoxic T Lymphocyte Serine Proteases: Subsite Mapping with Peptide Thioester Substrates and Inhibition of Enzyme Activity and Cytolysis by Isocoumarins," *Biochemistry* 30:2217–2227 (1991).

Orlowski et al., "Substrate Specificity and Inhibitors of a Capillary Injury–Related Protease from Sheep Lung Lymph," *Arch. Biochem. Biophys.* 269(1):125–136 (1989).

Orlowski, M., "The Multicatalytic Proteinase Complex, a Major Extralysosomal Proteolytic System," *Biochemistry* 29(45):10289–10297 (1990).

Orlowski et al., "Evidence for the Presence of Five Distinct Proteolytic Components in the Pituitary Multicatalytic Proteinase Complex," *Biochemistry* 32:1563–1572 (1993).

Ortiz–Navarrete et al., "Subunit of the '20S' Proteasome (Multicatalytic Proteinase) Encoded by the Major Histocompatibility Complex," *Nature* 353:662–664 (1991).

Oweida et al., "In Vivo Determination of the Anticoagulant Effect of a Substituted Isocoumarin (Acitic)," *Thromb. Res.* 58:191–197 (1990).

Parham, P., "Transporters of Delight," *Nature* 348:674–675 (1990).

Parkes et al., "Calpain Inhibition by Peptide Epoxides," *Biochem. J.* 230:509–516 (1985).

Powers et al., "Inhibitors of Serine Proteinases" *in: Proteinase Inhibitors,* Barrett et al. (eds.), Amsterdam: Elsevier Publishers, pp.55–152 (1986).

Powers et al., "Mechanism–Based Isocoumarin Inhibitors for Serine Proteases: Use of Active Site Structure and Substrate Specificity in Inhibitor Design," *J. Cell. Biochem.* 39:33–46 (1989).

Powers et al., "Reaction of Porcine Pancreatic Elastase with 7–Substituted 3–Alkoxy–4–chloroisocoumarins: Design of Potent Inhibitors Using the Crystal Structure of the Complex Formed with 4–Chloro–3–ethoxy–7–guanidinoisocoumarin," *Biochemistry* 29:3108–3118 (1990).

Powis et al., "Restoration of Antigen Presentation to the Mutant Cell Line RMA–S by an MHC–linked Transporter," *Nature* 354:528–531 (1991).

Puri et al., "Thrombin–Induced Platelet Aggregation Involves an Indirect Proteolytic Cleavage of Aggregin by Calpain," *Arch. Biochem. Biophys.* 271 (2):346–358 (1989).

Rao et al., "Influence of a Calcium Dependent Protease Inhibitor on Platelet Activation and Secretion," *Thromb. Res.* 47:625–637 (1987).

Rechsteiner, M., "Ubiquitin–Mediated Pathways for Intracellular Proteolysis," *Ann. Rev. Cell Biol.* 3:1–30 (1987).

Rivett A.J., "The Multicatalytic Proteinase," *J. Biol. Chem.* 264(21):12215–12219 (1989).

Rivett, A.J., "The Multicatalytic Proteinase of Mammalian Cells," *Arch. Biochem. Biophy.* 268(1):1–8 (1989).

Rock et al., "Generation of Class I MHC–Restricted T–T Hybridomas," *J. Immunol.* 145(3):804–811 (1990).

Saito et al., "The Structure–Function Relationship Between Peptide Aldehyde Derivatives on Initiation of neurite Outgrowth in PC12h Cells," *Chem. Abstr.* 115:562, Abstract No. 46708h (1991).

Scheffner et al., "The HPV–16 E6 and E6–AP Complex Functions as a Ubiquitin–Protein Ligase in the Ubiquitination of p53," *Cell* 75:495–505 (1993).

Sharma et al., "Peptide Transport by the Multidrug Resistance Pump," *J. Biol. Chem.* 267 (9):5731–5734 (1992).

Sheehan et al., "A Rapid Synthesis of Oligopeptide Derivatives without Isolation of Intermediates," *J. Am. Chem. Soc.* 87(11):2492–2493 (1965).

Sherwood et al., "In Vivo Inhibition of Cyclin B Degradation and Induction of Cell–Cycle Arrest in Mammalian Cells by the Neutral Cysteine Protease Inhibitor N–Acetylleucylleucylnorleucinal," *Proc. Natl. Acad. Sci. USA* 90:3353–3357 (1993).

Speiser et al., "Loss of ATP–dependent Proteolysis with Maturation of Reticulocytes and Erythrocytes," *J. Biol. Chem.* 257(23):14122–14127 (1982).

Spies et al., "Restored Expression of Major Histocompatibility Class I Molecules by Gene Transfer of a Putative Peptide Transporter," *Nature* 351:323–324 (1991).

Staubli et al., "Chronic Administration of a Thiol–proteinase Inhibitor Blocks Long–term Potentiation of Synaptic Responses," *Brain Research* 444:153–158 (1988).

Takahashi, Y., et al., "Electrochemical Reaction of Trialkylboranes with Acetone," *Chem. Letters*:669–672 (1978).

Tanaka et al., "Proteasomes: Protein and Gene Structures," *The New Biologist* 4(3):173–187 (1992).

Townsend et al., "Cytotoxic T Cells Recognize Fragments of the Influenza Nucleoprotein," *Cell* 42:457–467 (1985).

Townsend et al., "Cytotoxic T Lymphocytes Recognize Influenza Haemaggtutinin That Lacks a Signal Sequence," *Nature* 324:575–577 (1986).

Townsend et al., "Defective Presentation to Class I–Restricted Cytotoxic T Lymphocytes in Vaccinia–Infected Cells is Overcome by Enhanced Degradation of Antigen," *J. Exp. Med.* 168:1211–1224 (1988).

Townsend et al., "Assembly of MHC Class I Molecules Analyzed In Vitro," *Cell* 62:285–295 (1990).

Tsai, D.J.S., and Matteson, D.S., "Pinanediol [α(Trimethylsilyl)allyl]boronate and related Boronic Esters," *Organometallics* 2:236–241 (1983).

Tsai D.J.S., et al. "Diastereoselection in Reactions of Pinanediol Dichloromethaneboronate," *Organometallics* 2:1543–1545 (1983).

Tsubuki et al., "Purification and Characterization of a Z–Leu–Leu–Leu–MCA Degrading Protease Expected to Regulate Neurite Formation: A Novel Catalytic Activity in Proteasome," *Biochem. Biophys. Res. Comm* 196(3):1195–1201 (1993).

Tsujinaka et al., "Synthesis of a New Cell Penetrating Calpain Inhibitor (Calpeptin)," *Biochem. Biophys. Res. Comm.* 153(3):1201–1208 (1988).

Vijayalakshmi et al., "Structural Study of Porcine Pancreatic Elastase Complexed with 7–Amino–3–(2–bromoethoxy)–4–chloroisocoumarin as a Nonreactivatable Doubly Covalent Enzyme–Inhibitor Complex," *Biochemistry* 30:2175–2183 (1991).

Vinitsky et al., "Inhibition of the Chymotrypsin–like Activity of the Pituitary Multicatalytic Proteinase Complex," *Biochemistry* 31:9421–9428 (1992).

Vlasek et al., "Influenza C Virus Esterase: Analysis of Catalytic Site, Inhibition, and Possible Function," *J. Virol.* 63(5):2056–2062 (1989).

Waxman et al., "Demonstration of Two Distinct High Molecular Weight Proteases in Rabbit Reticulocytes, One of Which Degrades Ubiquitin Conjugates," *J. Biol. Chem.* 262(6):2451–2457 (1987).

Wilkinson et al., "A Specific Inhibitor of the Ubiquitin Activating Enzyme: Synthesis and Characterization of Adenosyl–Phospho–Ubiquitinol, a Nonhydrolyzable Ubiquitin Adenylate Analogue," *Biochemistry* 29:7373–7380 (1990).

Yang et al., "Proteasomes Are Regulated by Interferon γ: Implications for Antigen Processing," *Proc. Natl. Acad. Sci. USA* 89:4928–4932 (1992).

Yewdell et al., "Cell Biology of Antigen Processing and Presentation to Major Histocompatibility Complex Class I Molecule–Restricted T Lymphocytes," *Adv. Immunolo.* 52:1–123 (1992).

Zunino et al., "Localization, Implications for Function, and Gene Expression of Chymotrypsin–like Proteinases of Cytotoxic RNK–16 Lymphocytes," *Biochim.Biophys. Acta* 967:331–340 (1988).

English Translation of PCT Publication No. WO 94/23045, published on Oct. 13, 1994.

Derwent English Abstract of European Patent Office Publication No. Ep 0 315 574 (Doc. Ref. No. AN2), WPI Accession No. C89–061672 (3 pages). (Date unknown).

Derwent English Abstract of European Patent Office Publication No. EP 0 354 522 (Doc. Ref. No. AN2), WPI Accession No. C90–020104 (2 pages). (Date unknown).

INHIBITORS OF THE 26S PROTEOLYTIC COMPLEX AND THE 20S PROTEASOME CONTAINED THEREIN

CROSS-REFERENCES TO RELATED APPLICATIONS

This application is a continuation-in-part of U.S. patent application Ser. No. 08/212,909 filed Mar. 15, 1994, abandoned. The disclosure of this earlier filed application is hereby incorporated herein by reference.

BACKGROUND OF THE INVENTION

1. Field of the Invention

The present invention relates to a method for reducing the rate of intracellular protein breakdown by use of certain inhibitors of the proteasome.

2. Description of Related Art

Work undertaken to learn which of the proteolytic systems in mammalian cells is responsible for a large increase in protein breakdown in skeletal muscle during denervation atrophy, fasting, and other catabolic states (e.g., fever) has shown that most of the accelerated proteolysis in muscle in fasting or denervation atrophy is due to activation of a nonlysosomal (cytosolic) ATP-ubiquitin-dependent proteolytic process.

In the cytosol, there is a soluble proteolytic pathway that requires ATP and involves covalent conjugation of the cellular proteins with the small polypeptide ubiquitin ("Ub") (Hershko et al., *A. Rev. Biochem.* 61:761–807 (1992); Rechsteiner et al., *A. Rev. Cell. Biol.* 3:1–30 (1987)). Thereafter, the conjugated proteins are hydrolyzed by a 26S proteolytic complex containing a 20S degradative particle called the proteasome (Goldberg, *Eur. J. Biochem.* 203:9–23 (1992); Goldberg et al., *Nature* 357:375–379 (1992)). This multicomponent system is known to catalyze the selective degradation of highly abnormal proteins and short-lived regulatory proteins. However, the system also appears to be responsible for the breakdown of most proteins in maturing reticulocytes (Boches et al., *Science* 215:978–980 (1982); Spenser et al., *J. Biol. Chem.* 257:14122–14127 (1985)) and in growing fibroblasts (Ciechanover et al., *Cell* 37:57–66 (1984); Gronostajski et al., *J. Biol. Chem.* 260:3344–3349 (1985)).

There is also a system in the cytosol that generates antigenic particles from endogenously synthesized cellular and viral proteins (Moore et al., *Cell* 54:777–785 (1988); Morrison et al., *J. Exp. Med.* 163:903–921 (1986); Powis et al., *Nature* 354:529–531 (1991); Spies et al., *Nature* 351:323–324 (1991); Townsend et al., *Cell* 42:457–467 (1985); Townsend et al., *Nature* 324:575–577 (1986)). These low molecular weight peptides (LMP's), which are structurally similar to, if not identical with, proteasome subunits, bind to newly synthesized class I major histocompatibility complex molecules in the endoplasmic reticulum, and peptide/class I complexes are then transported to the cell surface for presentation to cytotoxic T cells (Monaco et al., *Proc. Natl. Acad. Sci. U.S.A.* 79:3001–3005 (1982); Monaco, *Immun. Today* 13:173–179 (1992); Yewdell et al., *Adv. Immun.* 52:1–123 (1992)). The means by which these peptides are produced is unknown, but a modification that promotes ubiquitin-dependent degradation of a viral protein enhances its presentation with class I (Townsend et al., *J. Exp. Med.* 168:1211–1224 (1988)) and indirect evidence suggests a role for proteolytic particles closely resembling and perhaps identical to the proteasome (Goldberg et al., *Nature* 357:375–379 (1992); Monaco, *Immun. Today* 13:173–179 (1992); Parham, *Nature* 348:674–675 (1990); Yang et al., *Proc. Natl. Acad. Sci. U.S.A.* 89:4928–4932 (1992)). Furthermore, the subunit patterns of the LMP complex and the proteasome are very similar and the two complexes display serological cross-reactivity (Brown et al., *Nature* 353:355–357 (1991)). Accordingly, it has been hypothesized that the proteasome may be responsible for cytoplasmic processing of MHC class I antigen molecules.

The 20S proteasome is composed of about 15 distinct 20–30 kDa subunits. It contains three or four different peptidases that cleave specifically on the carboxyl side of the hydrophobic, basic, and acidic amino acids (Goldberg et at., *Nature* 357:375–379 (1992); Goldberg, *Eur. J. Biochem.* 203:9–23 (1992); Orlowski, *Biochemistry* 29:10289 (1990); Rivett et al., *Archs. Biochem. Biophys.* 218:1 (1989); Rivett et al., *J. Biol. Chem.* 264:12,215–12,219 (1989); Tanaka et al., *New Biol.* 4:1–11 (1992)). These peptidases are referred to as the chymotrypsin-like peptidase, the trypsin-like peptidase, and the peptidylglutamyl peptidase, respectively. Which subunits are responsible for these activities is unknown, although the cDNA's encoding several subunits have been cloned (Tanaka et al., *New Biol.* 4:1–11 (1992)).

Recent studies have found that the 20S proteasomes resemble in size and subunit composition the MHC-linked LMP particles (Driscoll et al., *Cell* 68:823 (1992); Goldberg et al., *Nature* 357:375–379 (1992); Matthews et al., *Proc. Natl. Acad. Sci. U.S.A.* 86:2586 (1989); Monaco et al., *Human Immunology* 15:416 (1986); Parham, *Nature* 348:674–675 (1990); Martinez et al., *Nature* 353:664 (1991); Oritz-Navarette et al., *Nature* 353:662 (1991); Glynne et al., *Nature* 353:357 (1991); Kelly et al., *Nature* 353:667 (1991); Monaco et al., *Proc. Natl. Acad. Sci. U.S.A.* 79:3001 (1982); Brown et al., *Nature* 353:355 (1991); Goldberg, *Eur. J. Biochem.* 203:9–23 (1992); Tanaka et al., *New Biol.* 4:1–11 (1992)). The LMP particles contain two polypeptides, LMP 2 and LMP 7, which are encoded in the MHC chromosomal region. Immunochemical studies strongly suggest that LMP 2 and LMP 7 are two subunits of particles representing a small fraction of the 20S proteasome population.

Peptidases of the proteasome are distinctly regulated and changes in the relative activities of the peptidases can alter the nature of peptides that are generated by the proteasome and that are available for MHC-I antigen presentation. The MHC-encoded subunits are involved in the regulation of the peptidase activities. A defect in ubiquitin conjugation, an early step in the ATP-ubiquitin-dependent proteolytic pathway, leads to reduced MHC-I-restricted antigen presentation. A block at either an early step (ubiquitin conjugation) or a late step (processing of carboxyl-termini of the peptides) in the proteolysis of intracellular proteins by the ATP-ubiquitin system can inhibit class I restricted presentation.

Various inhibitors of the peptidases of the proteasome have been reported (Dick et al, *Biochemistry* 30:2725–2734 (1991); Goldberg et al., *Nature* 357:375–379 (1992); Goldberg, *Eur. J. Biochem.* 203:9–23 (1992); Orlowski, *Biochemistry* 29:10289 (1990); Rivett et al., *Archs. Biochem. Biophys.* 218:1 (1989); Rivett et al., *J. Biol. Chem.* 264:12,215–12,219 (1989); Tanaka et al., *New Biol.* 4:1–11 (1992)). These include known inhibitors of chymotrypsin-like and trypsin-like proteases, as well as inhibitors of thiol (or cysteine) and serine proteases. In addition, some endogenous inhibitors of proteasome activities have been isolated. These include the 240 kDa and the 200 kDa inhibitors isolated from human erythrocytes (Murakami et al., *Proc.*

*Natl. Acad. Sci. U.S.A.* 83:7588–7592 (1986); Li et al., *Biochemistry* 30:9709–9715 (1991)) and purified CF-2 (Goldberg, *Eur. J. Biochem.* 203:9–23 (1992)). In addition to antibiotic inhibitors originally isolated from actinomycetes (Aoyagi et al., *Proteases and Biological Control*, Cold Spring Harbor Laboratory Press, pp. 429–454 (1975)), a variety of peptide aldehydes have been synthesized, such as the inhibitors of chymotrypsin-like proteases described by Siman et al. (WO 91/13904).

Novel molecules can also be obtained and tested for inhibitory activity. As illustrated by the above cited references, various strategies are known in the art for obtaining the inhibitors for a given protease. Compound or extract libraries can be screened for inhibitors using peptidase assays. Alternatively, peptide and peptidomimetic molecules can be designed based on knowledge of the substrates of the protease. For example, substrate analogs can be synthesized containing a reactive group likely to interact with the catalytic site of the protease (see, e.g., Siman et al., WO 91/13904; Powers et al., in *Proteinase Inhibitors*, Barrett et al. (eds.), Elsevier, pp. 55–152 (1986)). The inhibitors can be stable analogs of catalytic transition states (transition state analog inhibitors), such as Z-Gly-Gly-Leu-H, which inhibits the chymotrypsin-like activity of the proteasome (Orlowski, *Biochemistry* 29:10289–10297 (1990); see also Kennedy and Schultz, *Biochemistry* 18:349 (1979)).

Various natural and chemical protease inhibitors reported in the literature, or molecules similar to them, include peptides containing an α-diketone or an α-keto ester, peptide chloromethyl ketones, isocoumarins, peptide sulfonyl fluorides, peptidyl boronates, peptide epoxides, and peptidyl diazomethanes (Angelastro et al., *J. Med Chem.* 33:11–13 (1990); Bey et al., EPO 363,284; Bey et al., EPO 364,344; Grubb et al., WO 88/10266; Higuchi et al., EPO 393,457; Ewoldt et al., *Molecular Immunology* 29(6):713–721 (1992); Hernandez et al., *Journal of Medicinal Chemistry* 35(6): 1121–1129 (1992); Vlasak et al., *Journal of Virology* 63(5):2056–2062 (1989); Hudig et al., *Journal of Immunology* 147(4):1360–1368 (1991); Odake et al., *Biochemistry* 30(8):2217–2227 (1991); Vijayalakshmi et al., *Biochemistry* 30(8):2175–2183 (1991); Kam et al., *Thrombosis and Haemostasis* 64(1):133–137 (1990); Powers et al., *Journal of Cellular Biochemistry* 39(1):33–46 (1989); Powers et al., *Proteinase Inhibitors*, Barrett et al., Eds., Elsevier, pp. 55–152 (1986); Powers et al., *Biochemistry* 29(12):3108–3118 (1990); Oweida et al., *Thrombosis Research* 58(2):391–397 (1990); Hudig et al., *Molecular Immunology* 26(8):793–798 (1989); Orlowski et al., *Archives of Biochemistry and Biophysics* 269(1):125–136 (1989); Zunino et al., *Biochimica et Biophysica Acta.* 967(3):331–340 (1988); Kam et al., *Biochemistry* 27(7):2547–2557 (1988); Parkes et al., *Biochem J.* 230:509–516 (1985); Green et al., *J. Biol. Chem.* 256:1923–1928 (1981); Angliker et al., *Biochem. J.* 241:871–875 (1987); Puri et al., *Arch. Biochem. Biophys.* 27:346–358 (1989); Hanada et al., *Proteinase Inhibitors: Medical and Biological Aspects*, Katunuma et al., Eds., Springer-Verlag pp. 25–36 (1983); Kajiwara et al., *Biochem. Int.* 15:935–944 (1987); Rao et al., *Thromb. Res.* 47:635–637 (1987); Tsujinaka et al., *Biochem. Biophys. Res. Commun.* 153:1201–1208 (1988)).

Various inhibitors of ubiquitin conjugation to proteins are also known (Wilkinson et al., *Biochemistry* 29:7373–7380 (1990)).

Certain peptide aldehydes and peptide α-keto esters containing a hydrophobic residue in the $P_1$ position were tested by Vinitsky et al. (*Biochemistry* 31:9421–9428 (1992), see also, Orlowski et al. *Biochemistry* 32:1563–1572 (1993)) as potential inhibitors of the chymotrypsin-like activity of the proteasome. Three peptide aldehydes, (benzyloxycarbonyl) -Leu-Leu-phenylalaninal (Z-LLF-H), N-acetyl-Leu-Leu-Norleucinal (Ac-LLnL-H), and N-acetyl-Leu-Leu-methioninal (Ac-LLM-H) were found to be slow binding inhibitors with $K_i$ values of 0.46, 5.7, and 33 μM, respectively. Of the several peptide α-keto ester inhibitors tested, Z-Leu-Leu-Phe-COOEt was the most potent inhibitor of the chymotrypsin-like activity with a $K_i$ of 53 μM.

Other tripeptides that have been described in the literature include Ac-Leu-Leu-Leu-H, Ac-Leu-Leu-Met-OR, Ac-Leu-Leu-Nle-OR, Ac-Leu-Leu-Leu-OR, Ac-Leu-Leu-Arg-H, Z-Leu-Leu-Leu-H, Z-Arg-Leu-Phe-H, and Z-Arg-Ile-Phe-H, where OR, along with the carbonyl of the preceding amino acid residue, represents an ester group.

Goldberg, in U.S. patent application Ser. No. 07/699,184, filed May 13, 1991, discloses that the ATP-ubiquitin-dependent process has been shown to be responsible for the excessive protein degradation that occurs in conditions or disease states in which there is severe loss of body mass and negative nitrogen balance. A method of inhibiting the accelerated or enhanced proteolysis, a method of identifying inhibitors of the process, multipain and proteasome inhibitors are also disclosed.

Goldberg et al., in U.S. patent application Ser. No. 08/016, 066, filed Feb. 10, 1993, disclose methods and drugs that inhibit the processing of antigens for presentation by major histocompatibility complex class I molecules. Specifically, inhibitors of the ATP-ubiquitin-dependent proteolytic pathway are described, which can inhibit MHC-I antigen presentation. These methods and drugs may be useful for the treatment of autoimmune diseases and for reducing rejection of organs and graft transplants. See, also, Michalek et al., *Nature* 363:552–554 (1993).

Tsubuki et al., *Biochem. and Biophys. Res. Commun.* 196(3):1195–1201 (1993) reported that a tripeptide aldehyde protease inhibitor, benzyloxycarbonyl(Z)-Leu-Leu-Leu-H, initiates neurite outgrowth in PC12 cells at an optimal concentration of 30 nM. The following synthetic peptides are also mentioned: Z-Leu-Leu-Gly-H, Z-Leu-Leu-Ala-H, Z-Leu-Leu-Ile-H, Z-Leu-Leu-Val-H, Z-Leu-Leu-Nva-H, Z-Leu-Leu-Phe-H, Z-Leu-Leu-Leu-H, Bz-Leu-Leu-Leu-H, Ac-Leu-Leu-Leu-H, Z-Leu-Leu-Leu.sc, Z-Leu-Leu-Leu.ol, Z-Leu-Leu-Leu, Dns-Leu-Leu-Leu-H, Dns-Leu-Leu-Leu-$CH_2Cl$, and Leupeptin.

Siman et al. (WO 91/13904) disclose chymotrypsin-like proteases and their inhibitors. The inhibitors have the formula R-A4-A3-A2-Y, wherein R is hydrogen, or a N-terminal blocking group;

A4 is a covalent bond, an amino acid or a peptide;

A3 is a covalent bond, a D-amino acid, Phe, Tyr, Val, or a conservative amino acid substituent of Val;

A2 is a hydrophobic amino acid or lysine or a conservative amino acid substituent thereof, or when A4 includes at least two amino acids, A2 is any amino acid; and Y is a group reactive with the active site of said protease.

Powers (WO 92/12140) discloses peptide ketoamides, ketoacids, and ketoesters and their use in inhibiting serine proteases and cysteine proteases.

Bartus et al. (WO 92/1850) disclose uses for Calpain inhibitor compounds and pharmaceutical compositions containing them. One use of these compounds is in the treatment of a neuredegenerative pathology in a human patient. The disclosure also provides additional uses and pharmaceutical compositions containing Calpain inhibitor compounds, such as peptide ketoamides, peptide ketoacids, and peptide ketoesters.

SUMMARY OF THE INVENTION

The present invention is based, inter alia, on the identification of the pathway responsible for the excessive protein degradation that occurs in conditions or disease states in which there is severe loss of body mass (e.g., cachexia) and negative nitrogen balance and the discovery of constituents of this pathway that make it possible to inhibit the pathway and the negative nitrogen balance in these catabolic states.

The present invention relates to a method for reducing the rate of intracellular protein breakdown. In a preferred embodiment, the present invention relates to a method of inhibiting (reducing or preventing) the accelerated breakdown of muscle proteins that accompanies various physiological and pathological states and is responsible to a large extent for the loss of muscle mass (atrophy) that follows nerve injury, fasting, fever, acidosis, and certain endocrinopathies.

An inhibitor of the 26S proteasome can be administered to an individual in whom loss of muscle mass occurs. Muscle mass losses are due in turn to accelerated breakdown of muscle proteins, which has been shown to be due largely to activation of the non-lysosomal ATP-ubiquitin-dependent pathway, in which an inhibitor of the ATP-dependent proteolytic complex will interfere with or reduce enhanced protein breakdown, which normally occurs in such conditions. As a result of the presence of the inhibitor, proteolysis is reduced and muscle protein loss occurs to a lesser extent than normally occurs in such conditions. This method of inhibiting the 26S proteasome, and thereby inhibiting destruction of muscle protein, can be used in a wide variety of conditions, such as cancer, chronic infectious diseases, fever, and muscle disuse and denervation, in which such muscle protein destruction occurs and which is often extremely debilitating.

More particularly, the present invention is directed to a method for reducing the rate of loss of muscle mass in an animal comprising contacting cells of the muscle with a proteasome inhibitor of the structure (1):

$$P-N-\left[B^1-X^1\right]_A-CH-X^2-CH-X \quad (1)$$
$$\phantom{P-N-}\vert\phantom{\left[B^1\right.}\vert\phantom{\left.\right]_A}\vert\phantom{-X^2-}\vert$$
$$\phantom{P-N-}R\phantom{\left[\right.}R^1\phantom{\left.\right]_A}R^2\phantom{-X^2-}R^3$$

where

P is an amino-group-protecting moiety;

$B^1$ at each occurrence is independently selected from the group consisting of

X is selected from the group consisting of

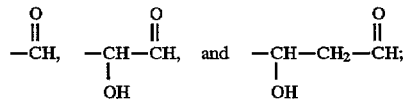

$X^1$ at each occurrence and $X^2$ are independently selected from the group consisting of

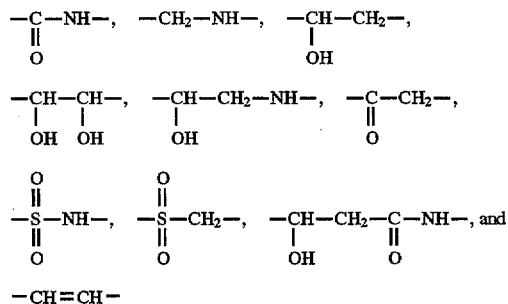

except that if $B^1$ is

then $X^1$, must be

R is hydrogen or together with the adjacent $R^1$, or $R^2$ if A=0, forms a nitrogen-containing heterocyclic ring;

$R^1$ at each occurrence, $R^2$, and $R^3$ are independently selected from the group consisting of hydrogen, alkyl, cycloalkyl, alkenyl, alkynyl, aryl, and —$CH_2$—$R^4$, where $R^4$ is aryl, aralkyl, alkaryl, cycloalkyl or —Y—$R^5$, where Y is a chalcogen, and $R^5$ is alkyl; and A is 0, 1, or 2; and wherein, stereochemically, $B^1$—$R^1$ is D, L, or a mixture thereof and CH—$R^2$ and CH—$R^3$ are independently L or a mixture of D and L.

The "animals" referred to herein are preferably mammals. Both terms are intended to include humans.

In other embodiments, the present invention is directed to compounds useful as proteasome inhibitors, to a method for reducing the rate of intracellular protein breakdown in an animal comprising contacting cells with such compounds, and to a method of reducing the rate of degradation of p53 protein in an animal subjected to DNA damaging drugs or radiation comprising administering to said animal a proteasome inhibitor of the structure (1 ) above.

Cyclins are proteins that are involved in cell cycle control in eukaryotes. Cyclins presumably act by regulating the activity of protein kinases, and their programmed degradation at specific stages of the cell cycle is required for the transition from one stage to the next. Experiments utilizing modified ubiquitin (Glotzer et al., Nature 349:132–138 (1991); Hershko et al., J. Biol Chem. 266:376 (1991)) have extablished that the ubiquitination/proteolysis pathway is involved in cyclin degradation. Accordingly, compounds that inhibit this pathway would cause cell cycle arrest and would be useful in the treatment of cancer, psoriasis, restinosis, and other cell proliferative diseases.

Inhibitors, such as those disclosed herein, provide an approach for inhibiting cytolytic immune responses. The proteasome inhibitors of structure (1) can be used to inhibit the processing of internalized cellular or viral antigens into antigenic peptides that bind to MHC-I molecules in an animal. The methods and drugs of this approach are useful for treating autoimmune diseases and preventing rejection of foreign tissues, such as transplanted organs or grafts. The strategy is to inhibit antigen presentation by major histocompatibility complex (MHC) class I molecules rather than suppress T cell activity. This approach has the advantage of selectively affecting only class I MHC-restricted immune responses and not antibody or other CD4+ T cell-mediated responses. Consequently, there should be less generalized immunosuppression and susceptibility to infection in the patient.

Specifically, the inhibitors described herein inhibit the processing of internalized cellular or viral antigens into the kind of peptides, referred to as antigenic peptides, that bind to the MHC-I molecules. MHC-I binding peptides have strict sequence and size requirements. In the absence of the antigenic peptides, the antigens are not presented at the cell surface and CD8+ T cells are not stimulated. Thus, the inhibitors of the present invention can block both the initiation of immune response and stop ongoing immune responses.

As described herein, the inventors have demonstrated that the proteasome inhibitor designated herein as MG 101 inhibits the MHC-I presentation of ovalbumin (Examples 7 and 8). Antigen presentation of an OVA peptide introduced into the cytosol was not inhibited, indicating that MG 101 is affecting the processing of the OVA protein into the peptide. This and other inhibitors are further described hereinafter.

DESCRIPTION OF THE PREFERRED EMBODIMENTS

Figure 1A:
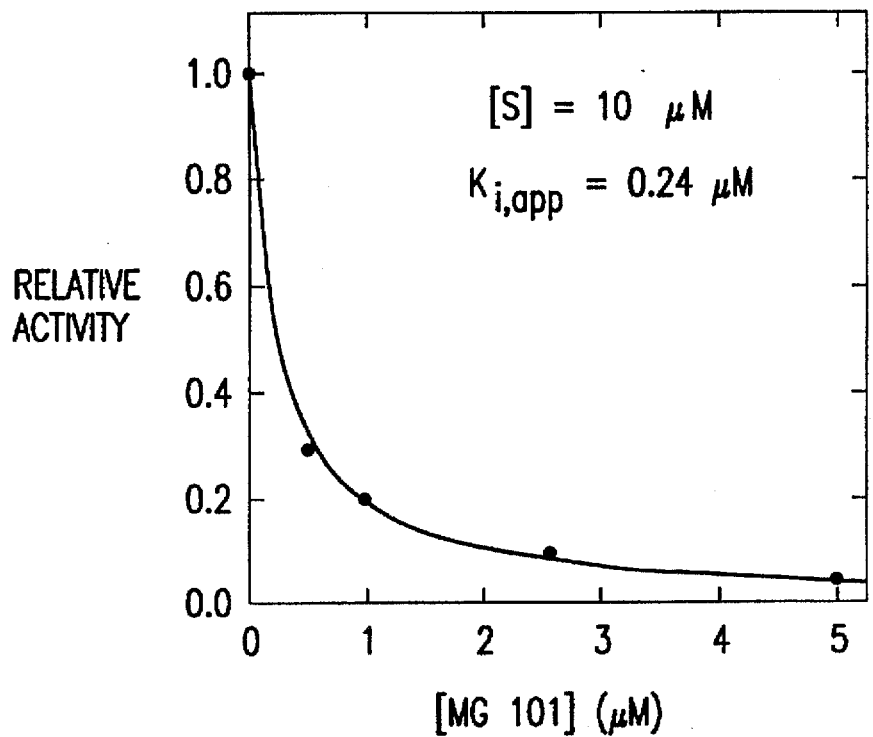
FIG. 1 is a pair of graphs showing that MG 101 is a competitive inhibitor of the peptidase activity of muscle 20S proteasome.

The present invention relates to proteasome inhibitors of the structure (1):

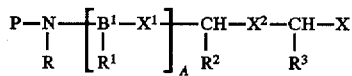

where

P is an amino-group-protecting moiety;

$B^1$ at each occurrence is independently selected from the group consisting of

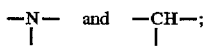

X is selected from the group consisting of

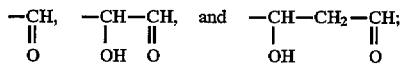

$X^1$ at each occurrence and $X^2$ are independently selected from the group consisting of

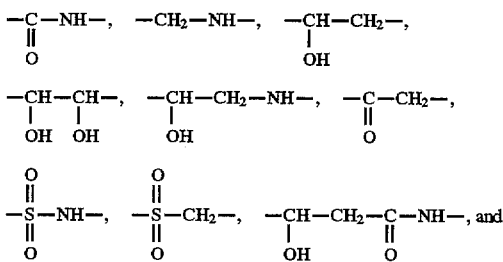

$-CH=CH-$ except that if $B^1$ is

then $X^1$ must be

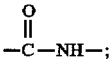

R is hydrogen or together with the adjacent $R^1$, or $R^2$ if A=0, forms a nitrogen-containing heterocyclic ring;

$R^1$ at each occurrence, $R^2$, and $R^3$ are independently selected from the group consisting of hydrogen, alkyl, cycloalkyl, alkenyl, alkynyl, aryl, and $-CH_2-R^4$, where $R^4$ is aryl, aralkyl, alkaryl, cycloalkyl or $-Y-R^5$, where Y is a chalcogen, and $R^5$ is alkyl; and A is 0, 1, or 2; and wherein, stereochemically, $B^1-R^1$ is D, L, or a mixture thereof and $CH-R^2$ and $CH-R^3$ are independently L or a mixture of D and L.

As noted above, P is an amino-group-protecting moiety, also known in the an as an "N-terminal blocking group." Included are such moieties as D-amino acids, arylcarbonyls, alkylcarbonyls, alkoxycarbonyls, aryloxycarbonyls, aralkyloxycarbonyls, aralkylsulfonyls, alkylsulfonyls, or arylsulfonyls, or other equivalents known by those skilled in the art of peptide synthesis to protect molecules from degradation by aminopeptidases (Gross and Meienhofer, eds., The Peptides, vol. 3, Academic Press, New York, 1981 pp. 3–81, describes numerous suitable amine protecting groups). As used herein, either individually or as part of a larger group, "alkyl" means a linear, cyclic, or branched-chain aliphatic moiety of 1 to 20 carbon atoms; "aryl" means an aromatic ring, e.g., phenyl, of 6 to 18 members, unsubstituted or substituted with one or more alkyl, substituted alkyl, nitro, alkoxy, or halo groups; "substituted alkyl" means an alkyl group having a substituent containing a heteroatom or heteroatoms such as N, O or S; "halo" means F, Cl, or Br, and "alkaryl" means an aryl ring of 7 to 19 members having an aliphatic substituent, and, optionally, other substituents such as one or more alkyl, substituted alkyl, alkoxy, or amino groups. "Aralkyl" means a linear or branched chain aliphatic moiety of 7 to 18 carbon atoms including an aryl group or groups.

In a preferred embodiment of the present invention, the P moiety of the proteasome inhibitor is (2)

$$R^7-R^6 \tag{2}$$

where $R^6$ is

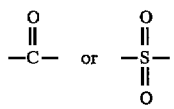

and $R^7$ is alkyl, aryl, alkaryl, aralkyl, alkoxy, aryloxy, alkaryloxy, aralkoxy, or a heterocyclic moiety.

Where $R^7$ is alkyl, it is preferably alkyl of from 1 to 4 carbon atoms, e.g., methyl, ethyl, propyl, butyl, or isomers thereof. Additionally, where $R^7$ is alkaryl, aralkyl, alkoxy, alkaryloxy, or aralkoxy, the alkyl moiety thereof is also preferably one having from 1 to 4 carbon atoms.

Where $R^7$ is aryl, it is preferably aryl of from 6 to 10 carbon atoms, e.g., phenyl or naphthyl, which may, if desired, be ring substituted. Additionally, where $R^7$ is alkaryl, aralkyl, aryloxy, alkaryloxy, or aralkoxy, the aryl moiety thereof is also preferably one having from 6 to 10 carbon atoms.

Where $R^7$ is heterocyclic, it can, for example, be a radical of furan, thiophene, pyrrole, 2H-pyrrole, 3H-pyrrole, pyrazole, 2H-imidazole, triazole, dithiole, oxathiole, isoxazole, oxazole, thiazole, isothiazole, oxadiazole, oxatriazole, 3H-dioxazole, dioxazole, 5H-oxathiazole, oxathiole, 2H-pyran, 4H-pyran, pyrone, dioxin, pyridine, pyridazine, pyrimidine, pyrazine, piperazine, triazine, oxazine, oxathiazine, isoxazine, oxathiazine, oxadiazine, morpholine, azepine, oxepin, thiepin, diazapine, benzofuran, isobenzofuran, benzo[b]thiophene, benzo[c]thiophene, indole, isoindole, cyclopenta[b]pyridine, pyrano[3,4-b]-pyrrole, indazole, indoxazine, benzoxazole, anthranil, 2H-chromene, coumarin, chroman-4-one, isocoumarin, isochromen-3-one, quinoline, isoquinoline, cinnoline, quinazoline, naphthyridine, pyridopyridine, benzoxazine, carbazole, acridine, purine, and the like.

Examples of suitable amino-group-protecting moieties include formyl, acetyl, trifluoroacetyl, benzyloxycarbonyl (carbobenzyloxy), substituted benzyloxycarbonyl, tertiary butyloxycarbonyl, isopropyloxycarbonyl, allyloxycarbonyl, phthaloyl, benzoyl, acetoacetyl, chloroacetyl, phenoxycarbonyl, methoxysuccinyl, succinyl, adipyl, suberyl, 2,4-dinitrophenyl, dansyl, p-methoxybenzenesulfonyl, p-toluenesulfonyl, methanesulfonyl, D-serine, D-glutamic acid, and the like.

It is most preferred that $R^7$ be

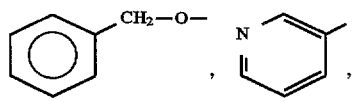
,
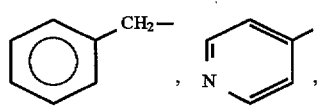
,

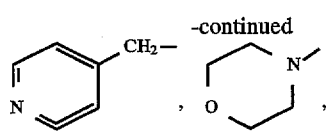
,

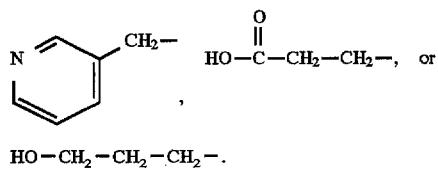
,

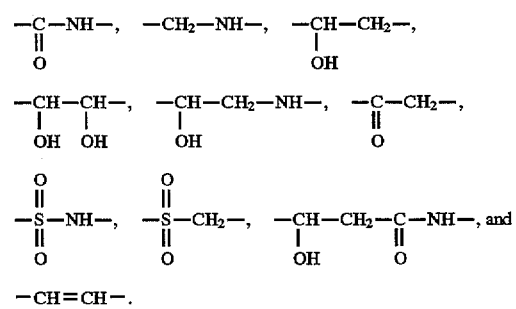

$HO-CH_2-CH_2-CH_2-$.

In structure (1), $X^1$ at each occurrence and $X^2$ represent peptide bonds or isosteres that can be used as peptide bond replacements in the proteasome inhibitors to increase bioavailability and reduce hydrolytic metabolism. As noted above, $X^1$ at each occurrence and $X^2$ are independently selected from the group consisting of

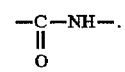

Preferably, $X^1$ at each occurrence and $X^2$ are

Furthermore, where $B^1$ is

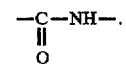

the $X^1$ adjacent thereto must be

—C—NH—.
‖
O

Introduction of these moieties into the proteasome inhibitors results in the following:

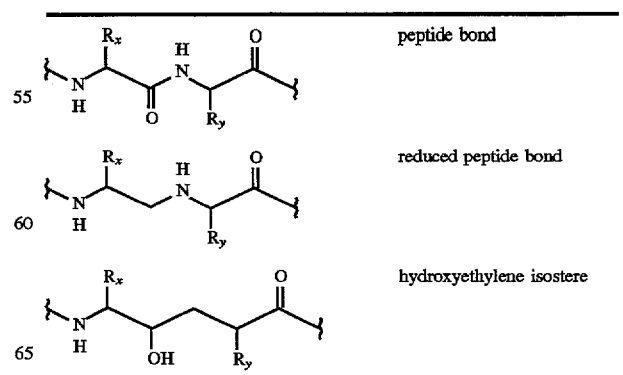

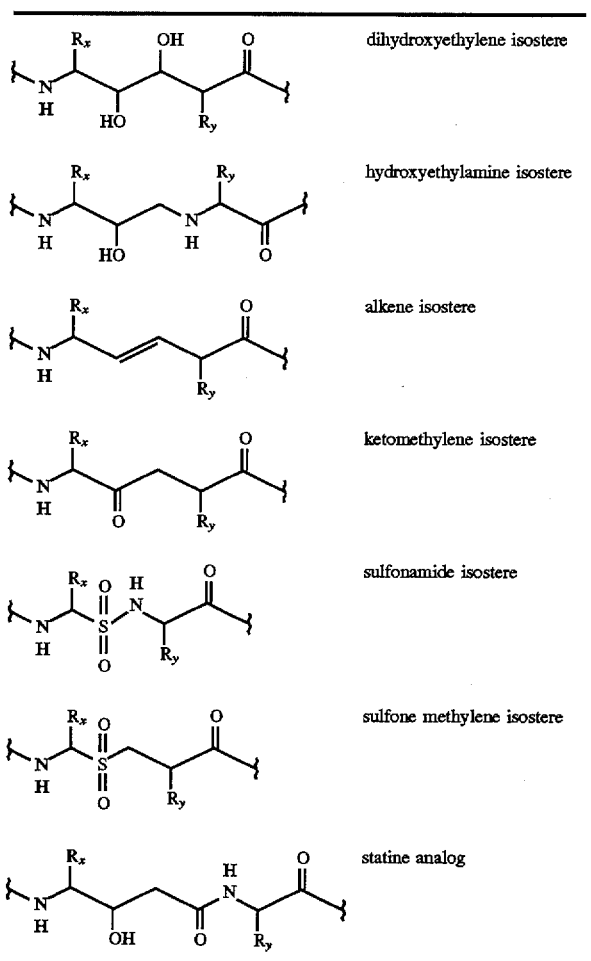

For example, if Z-Leu-Leu-Leu-H is found to undergo rapid hydrolytic metabolism to produce Z-Leu-OH and H₂N-Leu-Leu-H, the hydroxyethylene isostere can be prepared to eliminate this reaction:

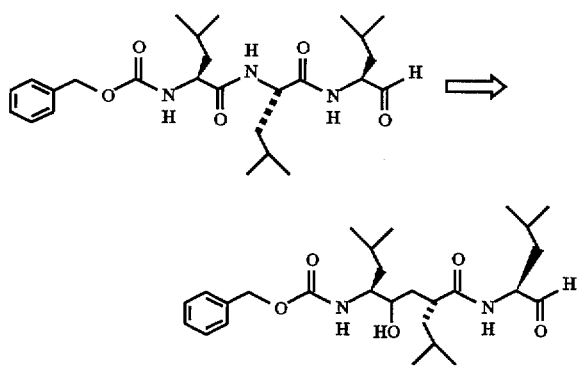

Another isostere within the scope of the present invention is the azapeptide isostere. This is the result of the replacement of the α-carbon atom of an amino acid with a nitrogen atom, e.g.,

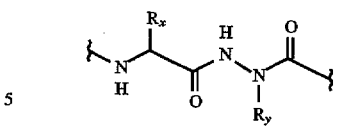

As noted above, A in structure (1) can be either 0, 1, or 2. Thus, when A is 0, no amino acid residue is present within the square brackets and the inhibitor is a dipeptide. Similarly, where A is 1, one amino acid residue is present within the brackets and the inhibitor is a tripeptide and, where A is 2, two amino acid residues are present within the brackets and the inhibitor is a tetrapeptide. It is preferred that A be 0 or 1, more preferred that it be 1.

It is preferred that $R^1$ at each occurrence and $R^2$ in structure (1) be independently selected from the group consisting of alkyl and —CH₂—$R^4$. More preferably, $R^1$ at each occurrence and $R^2$ are independently selected from the group consisting of alkyl groups of from 1 to 4 carbon atoms; e.g., methyl, ethyl, propyl, butyl, or isomers thereof, e.g., isopropyl, isobutyl, secbutyl, t-butyl; or —CH₂—$R^4$, where $R^4$ is cycloalkyl or naphthyl. It is more preferred that at least one of $R^1$ and $R^2$ be isobutyl,

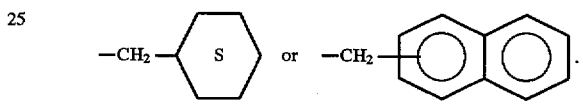

$B^1$—$R^1$ can be present in either the (D) or (L) configuration or as a mixture of both. CH—$R^2$ and CH—$R^3$ must be present in either the L configuration or a mixture of L and D. It is preferred that $R^1$, $R^2$, and $R^3$ all be of the L configuration.

Where $R^3$ is alkyl, it is preferably alkyl of from 1 to 4 carbon atoms, e.g., methyl, ethyl, propyl, butyl, or isomers thereof, which groups may be substituted or unsubstituted.

Where $R^3$ is aryl, it is preferably aryl of from 6 to 10 carbon atoms, e.g., phenyl or naphthyl, which groups may be substituted or unsubstituted.

Where $R^3$ is a substituted alkyl, it is preferably an alkyl of from 1 to 4 carbon atoms substituted with at least one aryl group of from 6 to 10 carbon atoms or at least one cycloalkyl group, preferably a cycloalkyl group having 5 or 6 carbon atoms, which groups may be substituted or unsubstituted.

Where $R^3$ is substituted aryl, it is preferably substituted with at least one alkyl group of from 1 to 4 carbon atoms, which groups may be substituted or unsubstituted.

Where $R^3$ is cycloalkyl, it is preferably cycloalkyl of from 5 to 6 carbon atoms, e.g., cyclopentyl or cyclohexyl, which groups may be substituted or unsubstituted.

Where $R^3$ is substituted cycloalkyl, it is preferably substituted with at least one aryl group of from 6 to 10 carbon atoms or at least one alkyl group, preferably an alkyl group having 1 to 4 carbon atoms, which groups may be substituted or unsubstituted.

Where $R^4$ is —Y—$R^5$, Y is a chalcogen, preferably oxygen or sulfur, more preferably sulfur; and $R^5$ is alkyl, preferably alkyl of from 1 to 4 carbon atoms, e.g., methyl, ethyl, propyl, butyl, or isomers thereof.

R in the structure shown above is hydrogen or together with the adjacent $R^1$, or $R^2$ if A=0, forms a nitrogen-containing heterocyclic ring. This ring can, optionally, be fused to another 5- to 7-membered saturated or aromatic ring, e.g., tetrahydroisoquinolinyl. Either ring can additionally be substituted by hydroxy, alkoxy, alkyl, aryl, arylalkyl, alkylaryl, or, if the ring is saturated, oxo.

Where such a ring system is present, it is preferred that it be one of the following:

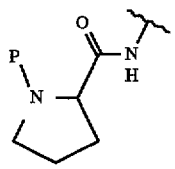

or

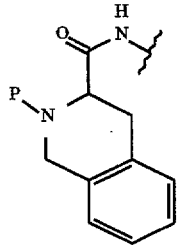

Examples of suitable proteasome inhibitors include, without limitation, the following compounds:

| | |
|---|---|
| Ac—Leu—Leu—Nle—H | (3) |
| Z—Leu—Leu—Val—H | (4) |
| Z—Leu—Leu—Nle—H | (5) |
| Z—Leu—Leu—Phe—H | (6) |
| Z—Leu—Leu-2-Nal—H | (7) |
| Z—Leu—Leu—Gly—H | (8) |
| Z—Leu—Leu—Ala—H | (9) |
| Z—Leu—Leu—Abu—H | (10) |
| Z—Leu—Leu—Nva—H | (11) |
| Z—Leu—Leu—Tyr—H | (12) |
| Z—Leu—Leu—Leu—H | (13) |
| Z—Leu—Leu—Ile—H | (14) |

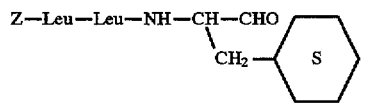 (15)

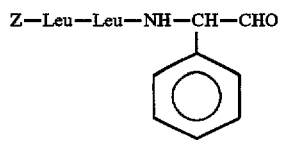 (16)

Z—Leu—Leu—Trp—H (17)

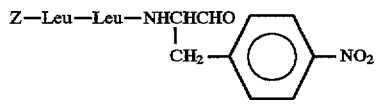 (18)

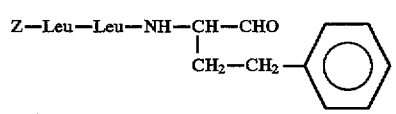 (19)

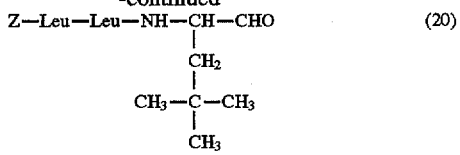 (20)

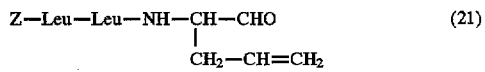 (21)

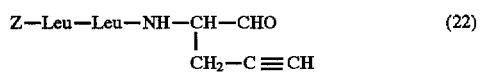 (22)

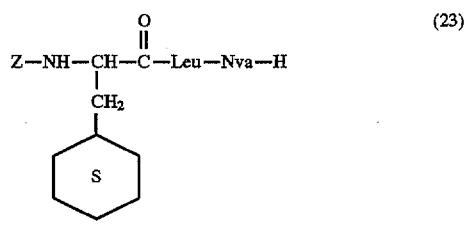 (23)

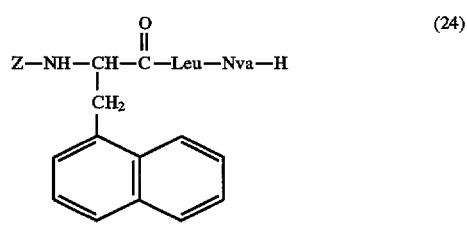 (24)

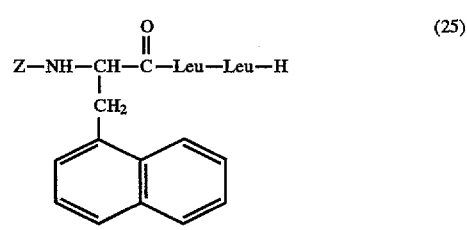 (25)

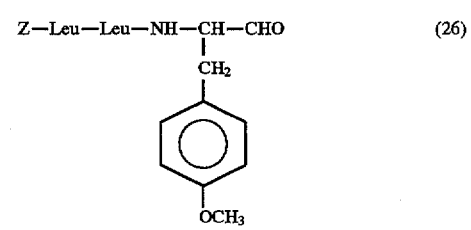 (26)

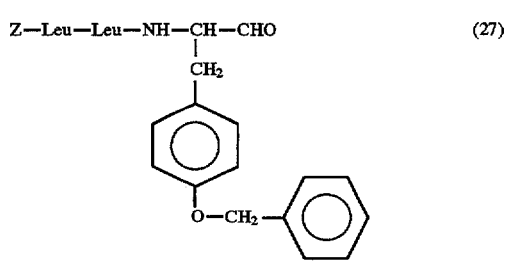 (27)

Ac—Leu—Leu—Leu—H (28)

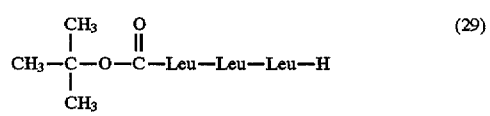 (29)

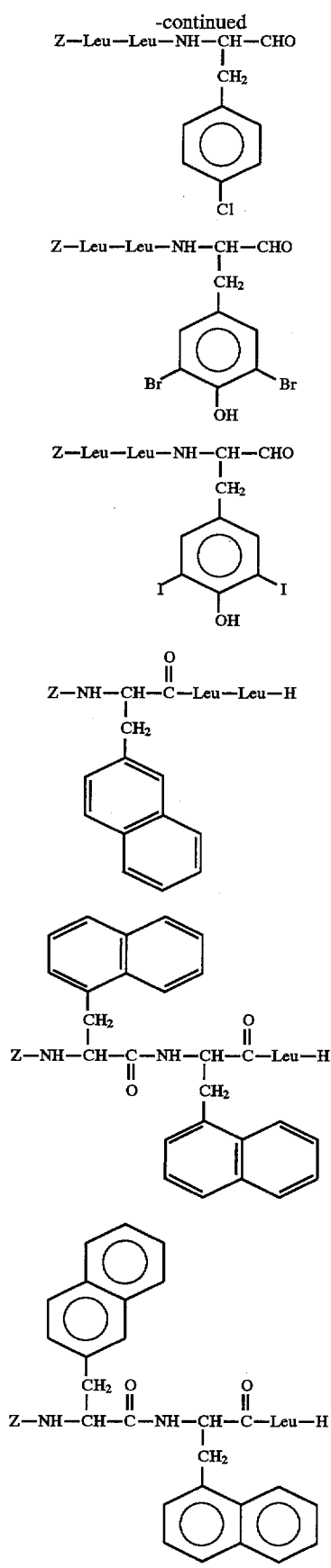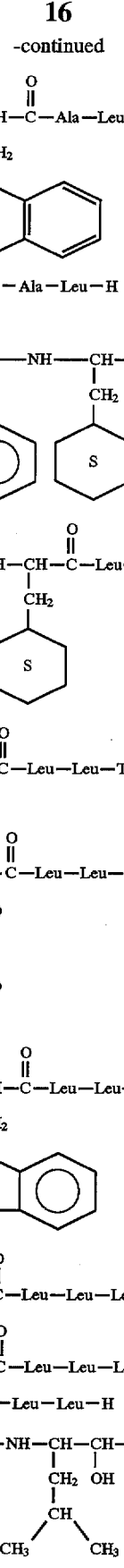

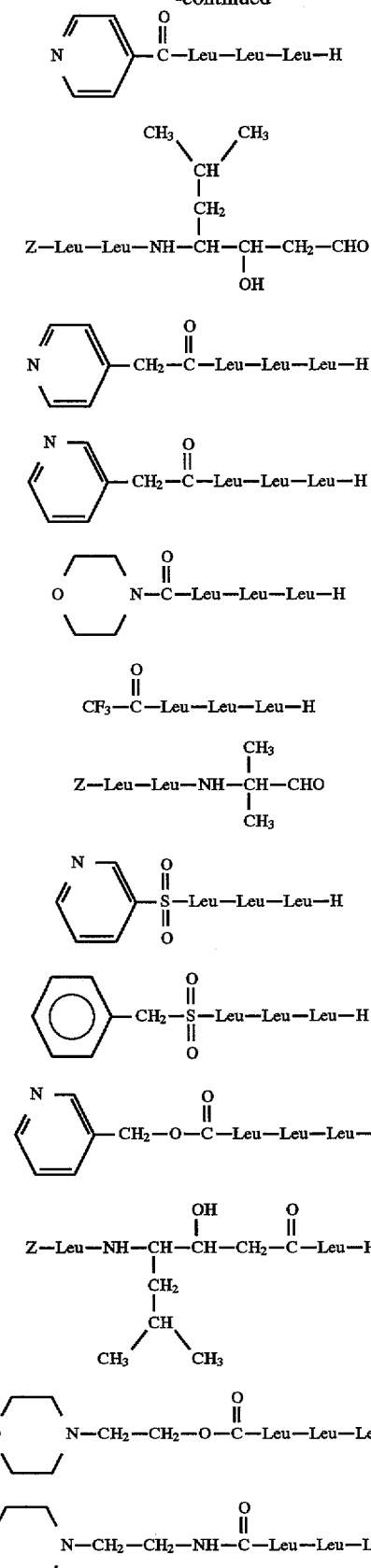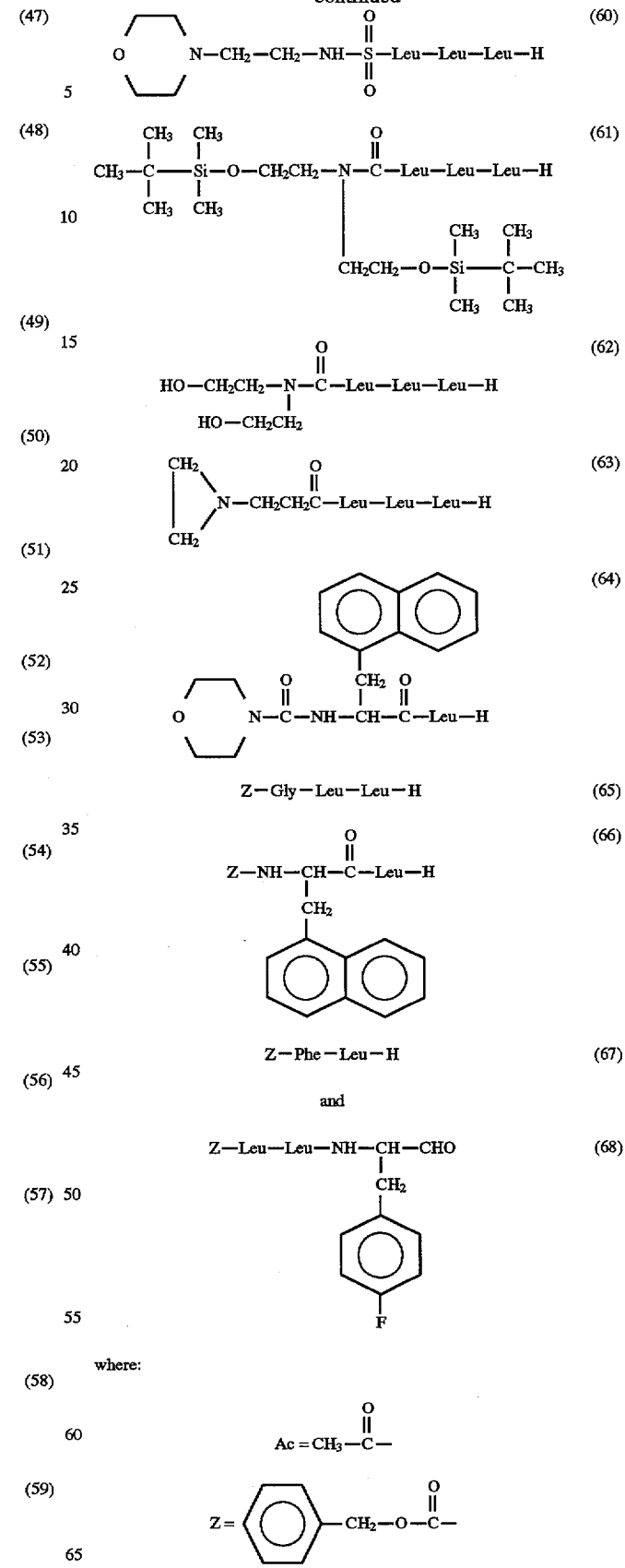

2-Nal = 2-Naphthylalanine 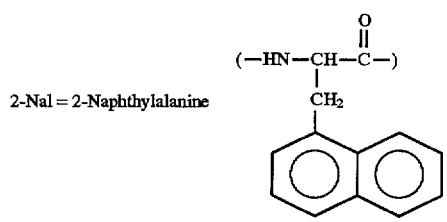
Most preferably, the proteasome inhibitors are:
(69) 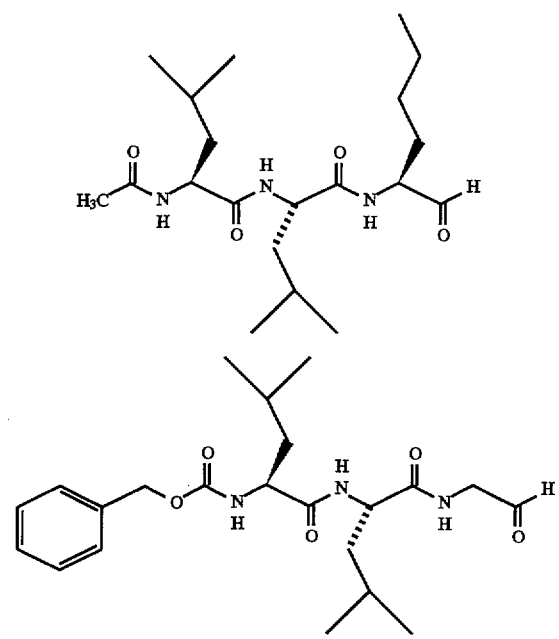
(70)
(71)
(72)
(73) 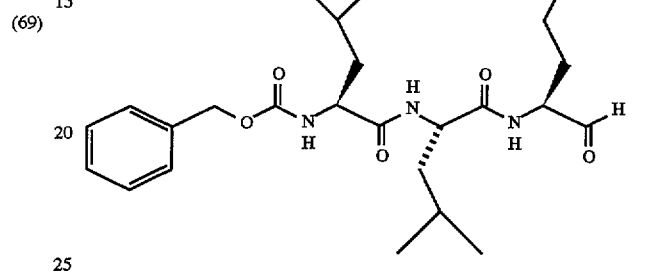
(74) 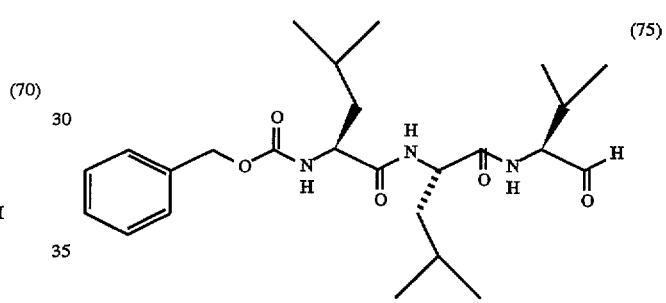
(75)
(76) 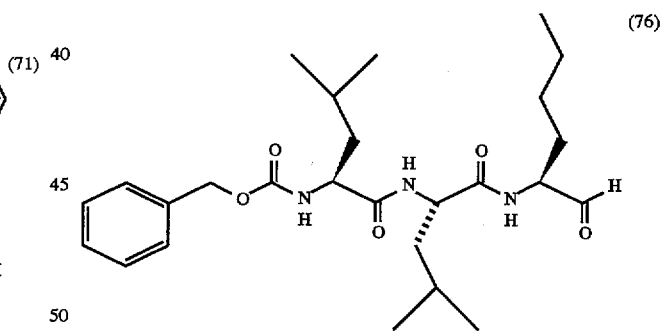
(77) 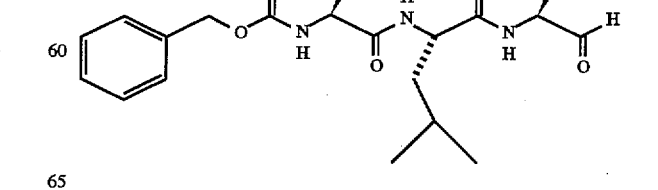

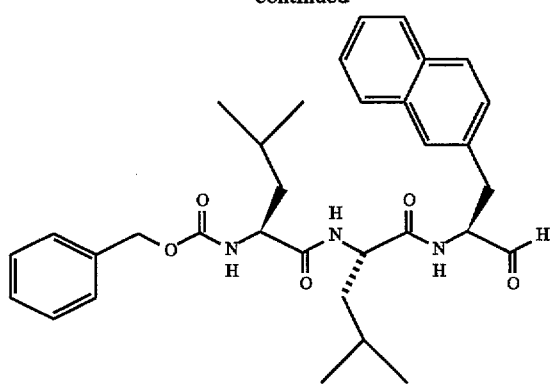
(78)
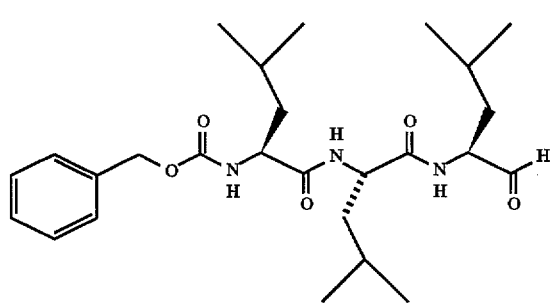
(79)
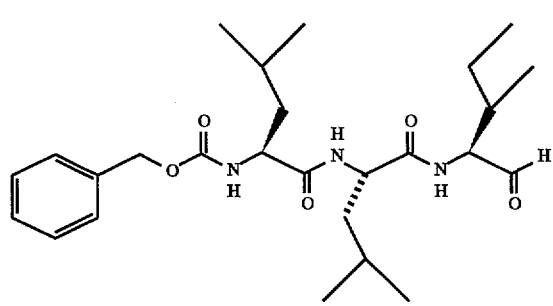
(80)
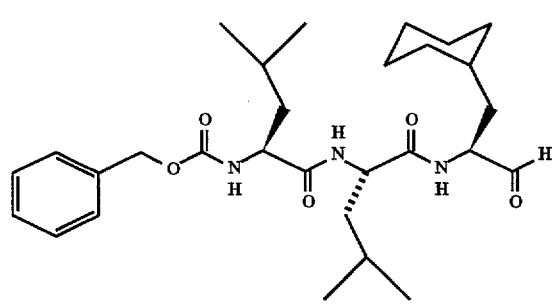
(81)
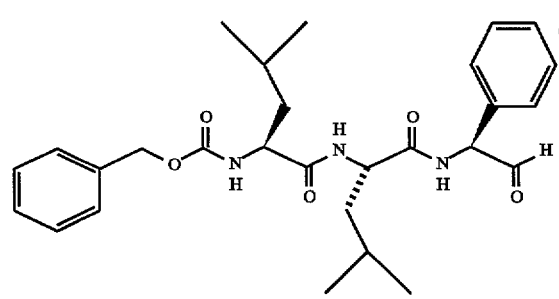
(82)
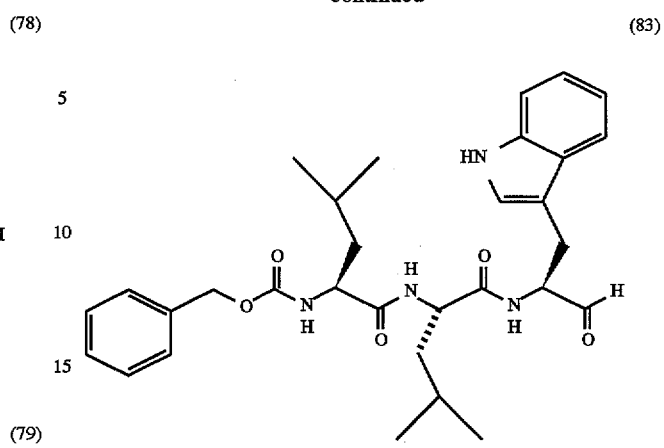
(83)
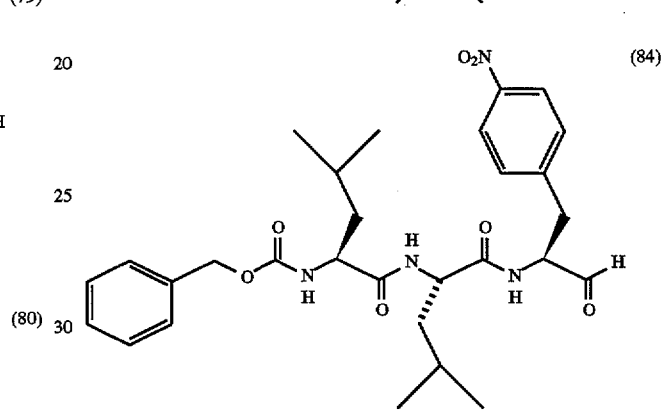
(84)
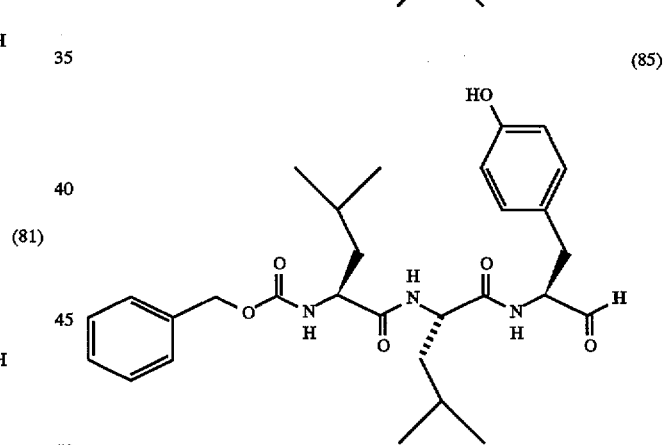
(85)
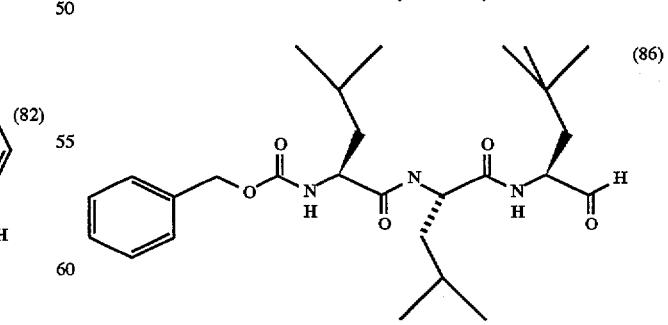
(86)

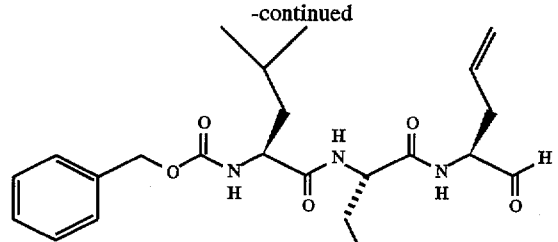
(87)
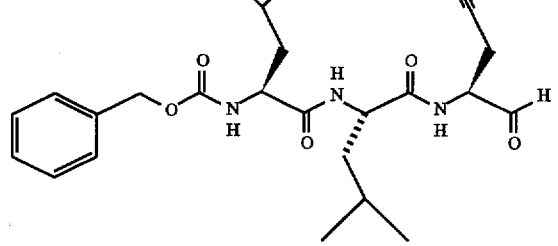
(88)
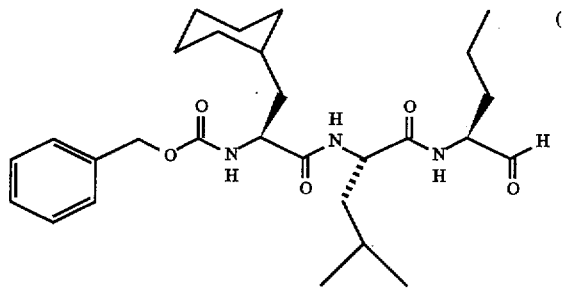
(89)
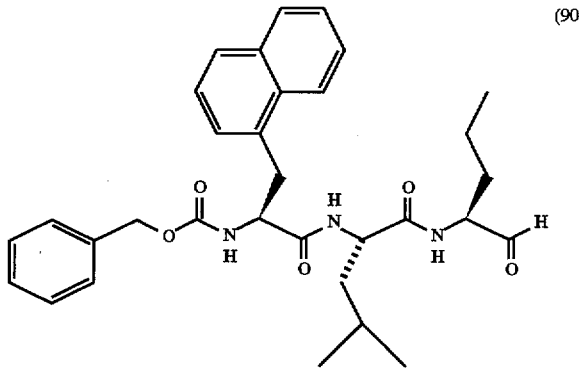
(90)
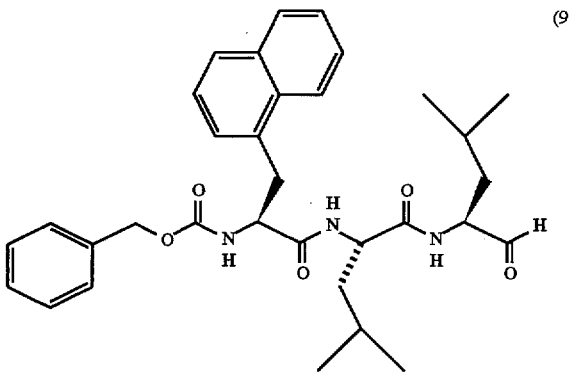
(91)
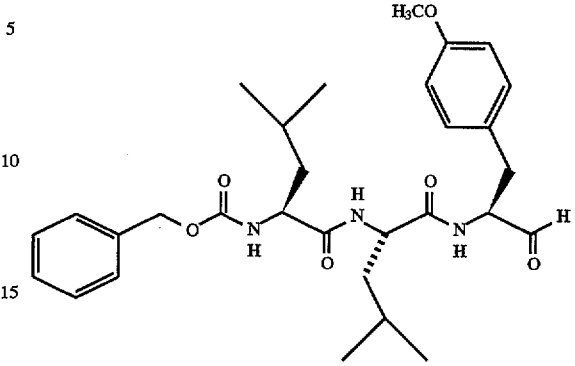
(92)
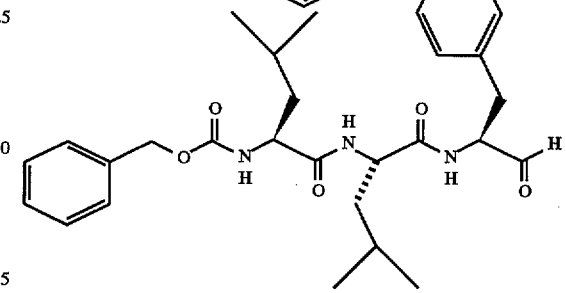
(93)
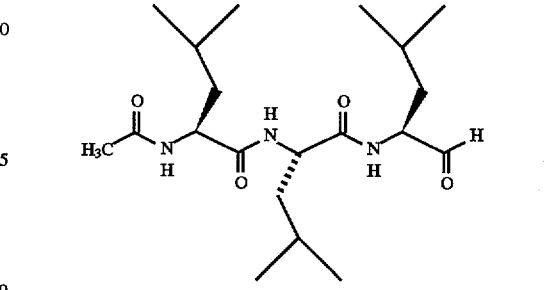
(94)
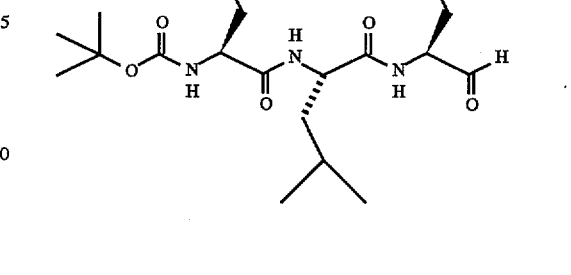
(95)

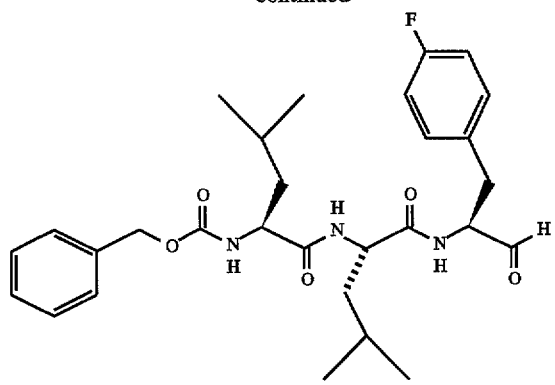
(96)
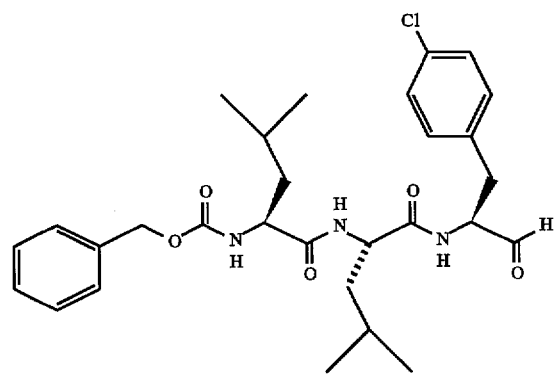
(97)
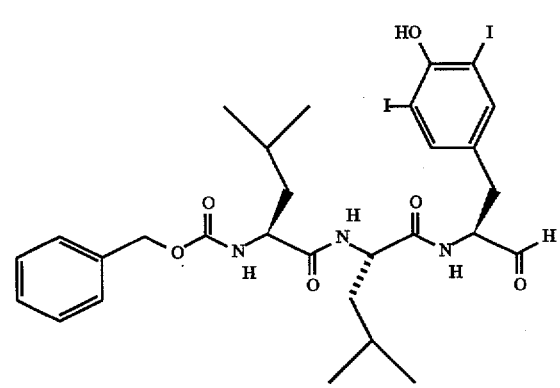
(98)
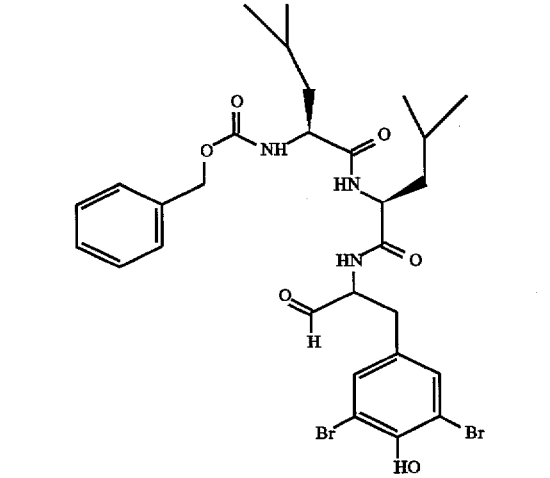
(99)
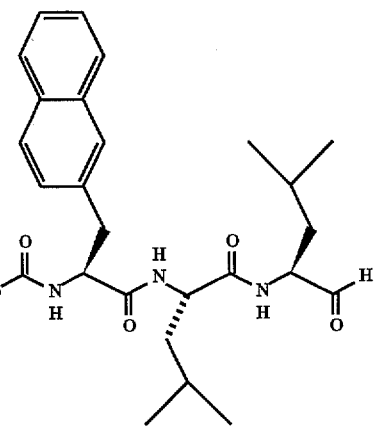
(100)
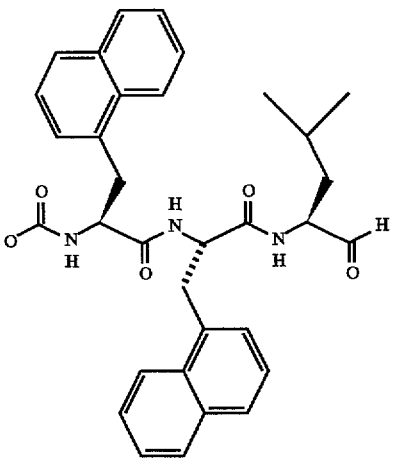
(101)
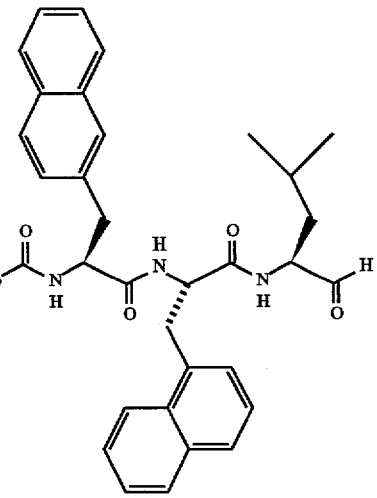
(102)

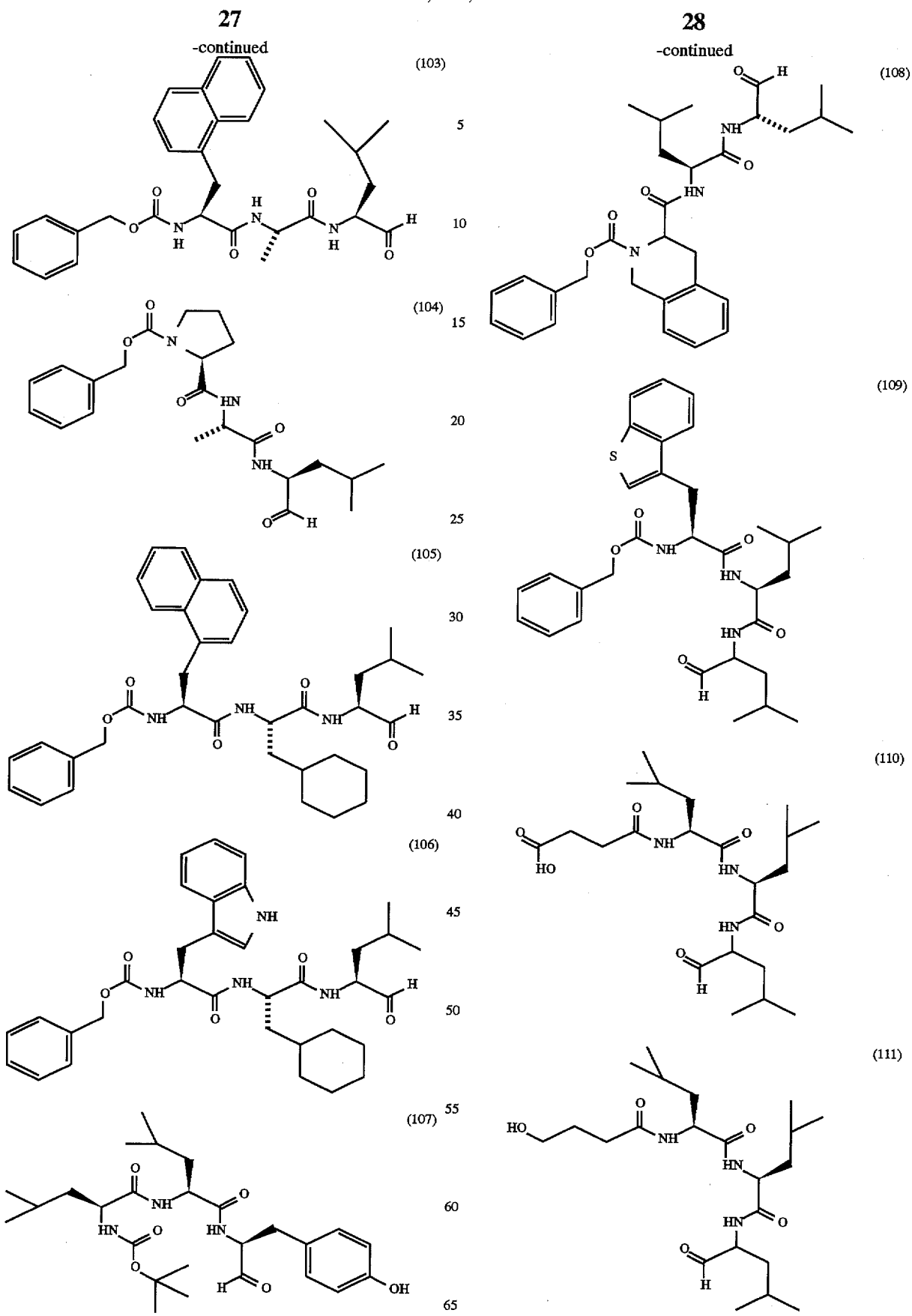

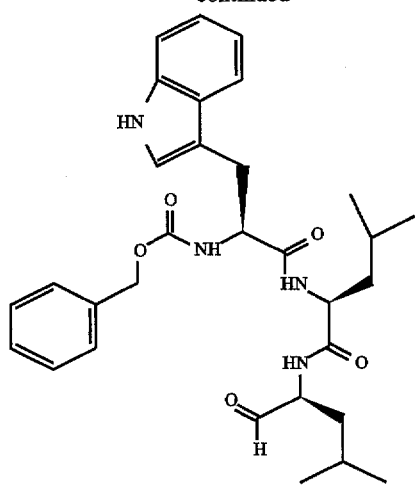
(112)
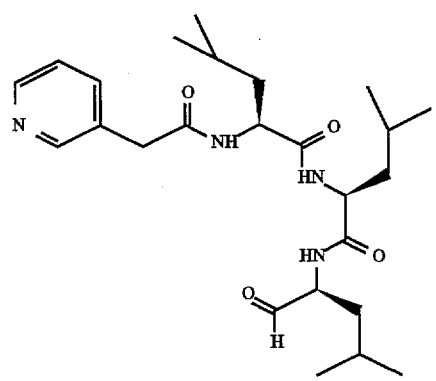
(116)
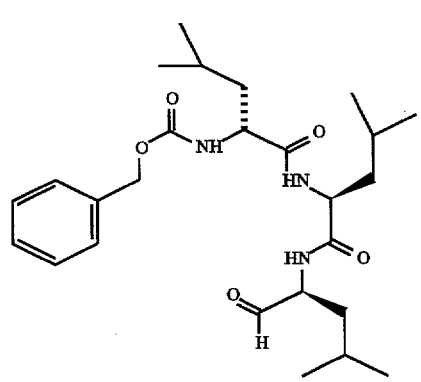
(113)
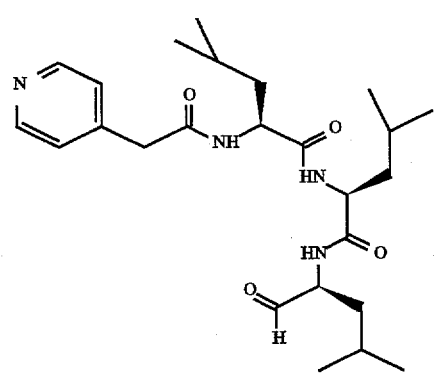
(117)
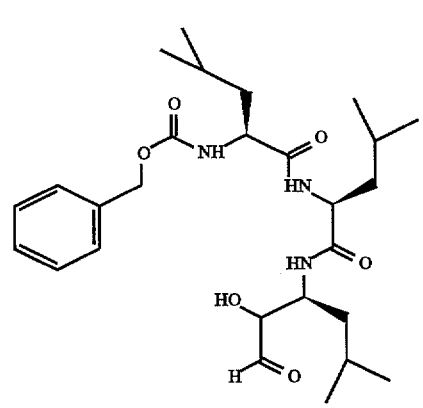
(114)
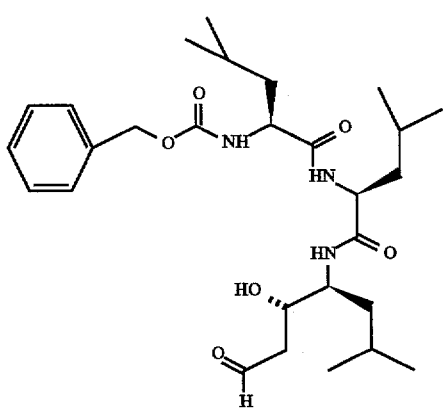
(118)
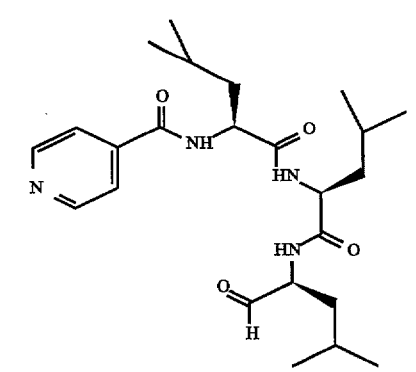
(115)
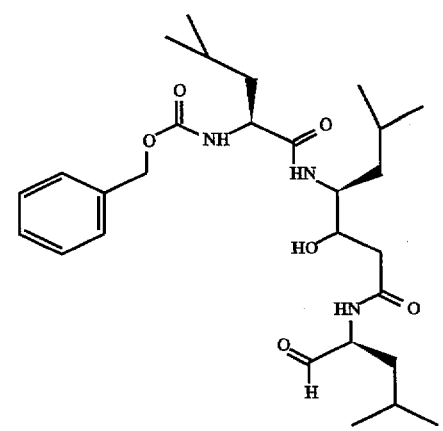
(119)

31
-continued
(120)
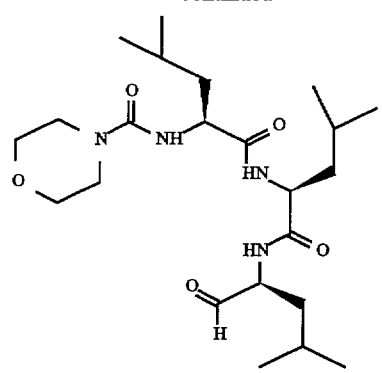
(121)
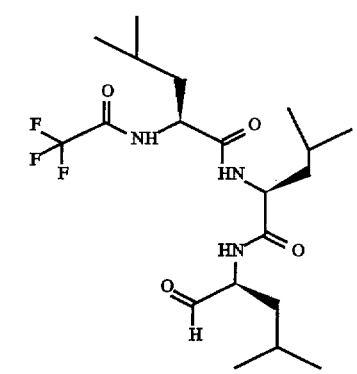
(122)
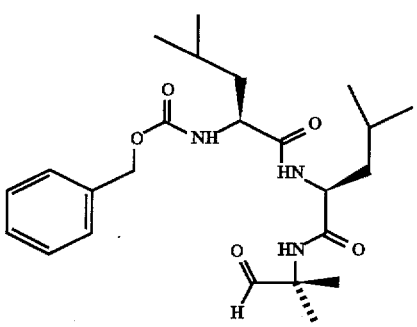
(123)
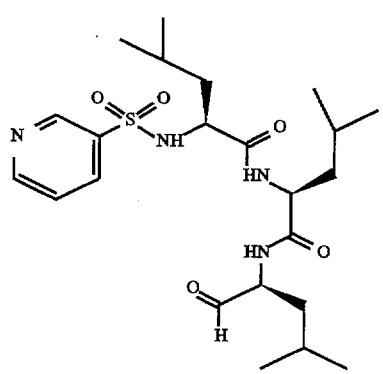
32
-continued
(124)
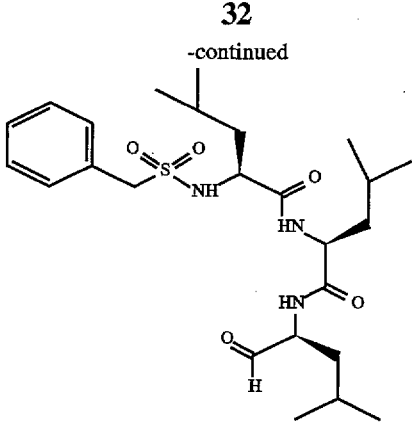
(125)
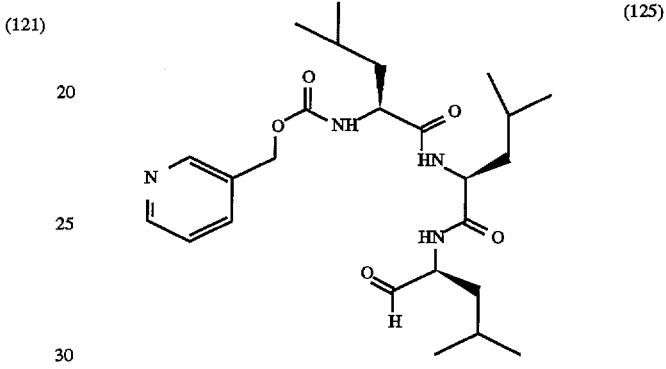
(126)
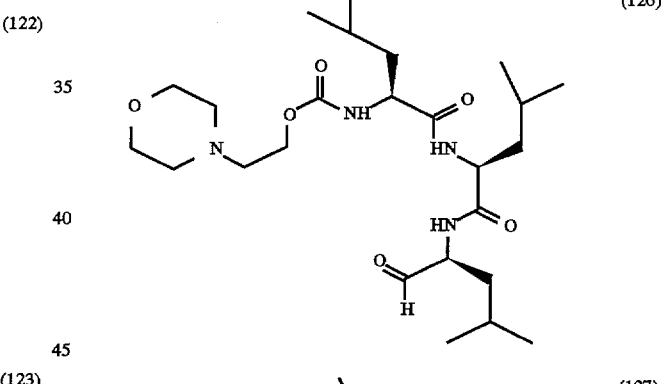
(127)
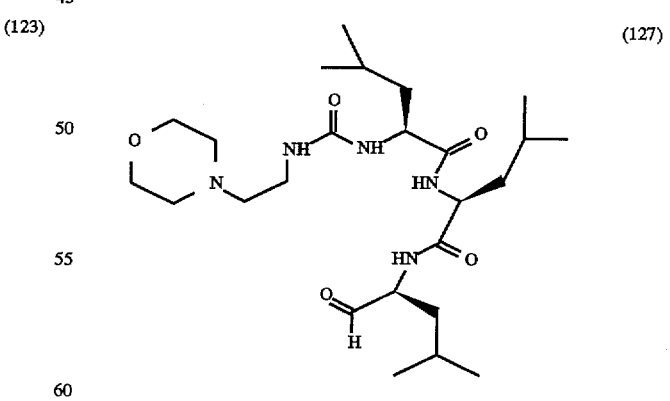

(128) 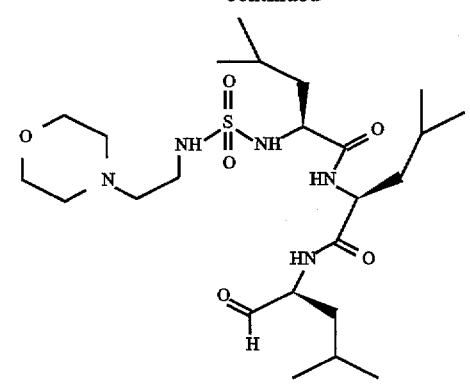

(129) 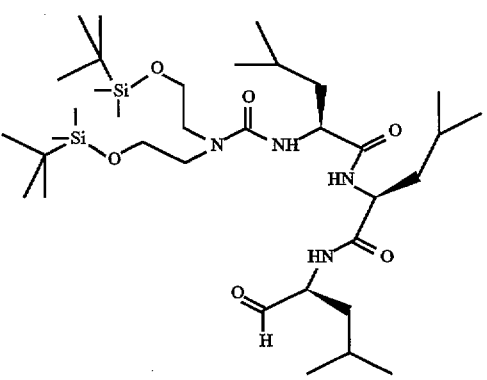

(130) 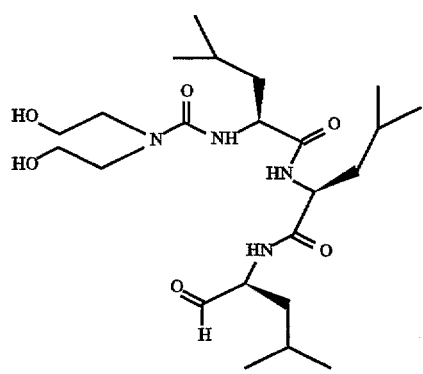

(131) 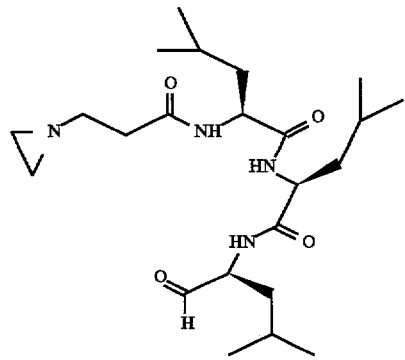

(132) 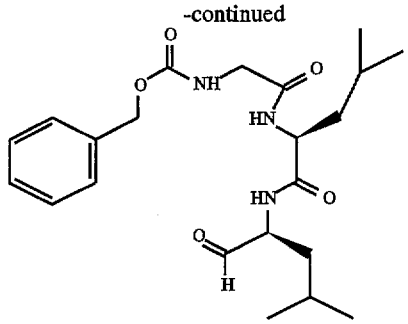

(133) 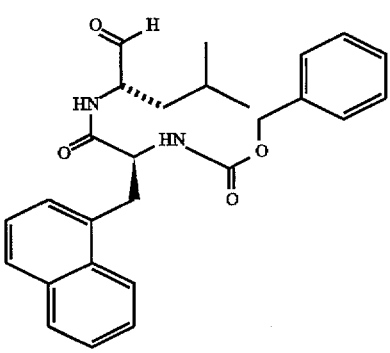

(134) 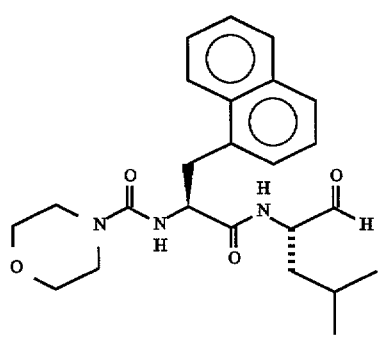

(135) 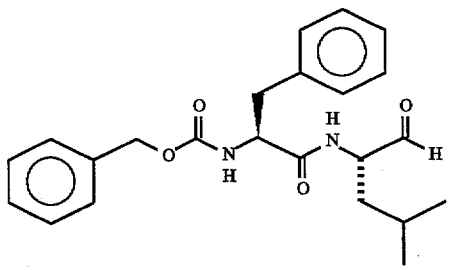

The present invention relates to a method of inhibiting (reducing or preventing) the accelerated or enhanced proteolysis that occurs in atrophying muscles and is known to be due to activation of a nonlysosomal ATP-requiring process in which ubiquitin plays a critical role. In the present method, the accelerated proteolysis is inhibited by interfering with the ATP-Ub-dependent pathway at one or more possible steps (e.g., by interfering with activity of the 26S proteasome or by interfering with activity of one of its components).

Thus, inhibition of the ATP-ubiquitin-dependent pathway is a new approach for treating the negative nitrogen balance in catabolic states. This can be effected through use of an inhibitor of the present invention, resulting in reduction of loss of muscle mass in conditions in which it occurs. Such an inhibitor can also be used in reducing the activity of the cytosolic ATP-ubiquitin-dependent proteolytic system in cell types other than muscle cells. Excessive protein loss is common in many types of patients, including individuals with sepsis, burns, trauma, many cancers, chronic or systemic infections, neuromotor degenerative disease, such as muscular dystrophy, acidosis, or spinal or nerve injuries. It also occurs in individuals receiving corticosteroids, and those in whom food intake is reduced and/or absorption is compromised. Moreover, inhibitors of the protein breakdown pathway could possibly be valuable in animals, e.g., for combating "shipping fever", which often leads to a major weight loss in cattle or pigs.

An assessment of whether the accelerated proteolysis evident in atrophy of skeletal muscles upon denervation or fasting is catalyzed by the nonlysosomal ATP-dependent or energy-independent degradative systems has been carried out. This work clearly demonstrated a link between the nonlysosomal ATP-dependent pathway and muscle wasting. It has been shown that in a variety of catabolic states (e.g., denervation, fasting, fever, certain endocrinopathies or metabolic acidosis) muscle wasting is due primarily to accelerated protein breakdown and, in addition, that the increased proteolysis results from activation of the cytosolic ATP-ubiquitin-dependent proteolytic system, which previously had been believed to serve only in the rapid elimination of abnormal proteins and certain short-lived enzymes. The discovery that this pathway is responsible for the accelerated proteolysis in these catabolic states is based on studies in which different proteolytic pathways were blocked or measured selectively in incubated muscles, and the finding of increased mRNA for components of this pathway (e.g., for ubiquitin and proteasome subunits) and increased levels of ubiquitin-protein conjugates in the atrophying muscles. The nonlysosomal ATP-ubiquitin-dependent proteolytic process increases in muscle in these conditions and is responsible for most of the accelerated proteolysis that occurs in atrophying muscles. There is a specific increase in ubiquitin mRNA, induction of mRNA for proteasome and increased ubiquitinated protein content in atrophying muscles that is not seen in non-muscle tissue under the same conditions.

The inhibitors of the present invention can be used to reduce (totally or partially) the nonlysosomal ATP-dependent protein degradation shown to be responsible for most of the increased protein degradation that occurs during fasting, denervation, or disuse (inactivity), steroid therapy, febrile infection, and other conditions.

It will be necessary to determine whether any inhibitors found to be effective against the 26S proteasome complex can selectively inhibit protein breakdown in intact cells. This can be done as follows: first, crude extracts of muscle are used to test the inhibitor's ability to block the entire ATP-ubiquitin-dependent pathway. Such studies can use model radioactive substrates as well as endogenous cell proteins, whose degradation can be easily followed by measuring the appearance of free tyrosine (Kettelhut et al., Diabetes/Metab. Rev. 4:1613–1621 (1982)). Promising agents are then tested on intact rat muscles and cultured cells, in order to evaluate their efficacy against the intracellular proteolysis, their ability to permeate mammalian cells, and their effects on cell viability.

A particularly useful approach to testing drug candidates for their ability to inhibit the ATP-ubiquitin-dependent degradative process is to do so in cultured cells in which a short-lived protein whose degradation is ubiquitin-dependent is produced. Inhibition of the process leads to accumulation of the protein in the cytosol. The extent to which the protein accumulates in the cytosol can be determined, using known methods. For example, a potential inhibitor of the process can be introduced into cultured cells producing a short-lived enzyme and the extent to which the enzyme is present in the cytosol in the presence of the potential inhibitor can be compared with the extent to which it occurs in its absence. Accumulation of the enzyme in the presence of the potential inhibitor is indicative of inhibition of the ATP-ubiquitin-dependent processes by the potential inhibitor being tested. Cultured cells, such as COS cells, which are stably transformed with a gene encoding a short-lived protein whose degradation is ubiquitin-dependent (e.g., a short-lived enzyme, such as a mutant β-galactosidase from E. coli, whose half-life is about 15 minutes and whose degradation is ubiquitin-dependent) can be used (Bachmair, A. et al., Science 234:179–186 (1986); Gonda, D. K. et at., J. Biol. Chem. 264:16700–16712 (1989)). Other mutant forms of enzymes that are rapidly degraded can also be used. Accumulation of the mutant β-galactosidase in COS cytosol in the presence of a substance being assessed for its ability to inhibit the process (a potential inhibitor) is indicative of inhibition of the process. An appropriate control is COS cells maintained under the same conditions, but in the absence of the potential inhibitor. This approach can be used to screen for effective inhibitors from microbial broths or chemical libraries.

Inhibitors thus found to be effective are then tested in vitro in incubated muscles from rats. In such experiments, the soleus or extensor digitorum longus muscles from one leg can be incubated with an inhibitor, while the contralateral, identical muscle serves as a control. The advantage of such approaches is that they are highly sensitive, inexpensive, and do not require isotopic labeling of animals (Kettelhut et al., Diabetes/Metab. Rev. 4:75 1–772 (1988); Furuno et al., J. Biol. Chem. 265:8550–8557 (1990)). With experience, it is easy with six animals to demonstrate statistically significant changes in overall protein breakdown or synthesis as small as 10–15%. It can be calculated from the average turnover time of muscle proteins that even changes of this magnitude in proteolysis could be of therapeutic benefit; if maintained for 2 weeks, a 15% reduction in proteolysis by itself should lead to at least a doubling of mass of a denervated muscle. It is also of interest to follow the effects of the inhibitor on breakdown of myofibrillar proteins, which constitute 60% of the muscle mass and represent the major protein reserve in the organism. These proteins are lost differentially upon denervation or fasting (Furuno et al., J. Biol. Chem. 265:8550–8557 (1990)). The degradation of myofibrillar components can be followed specifically by measuring 3-methylhistidine release from muscle proteins, which is a specific assay for breakdown of actin (Furuno et al., J. Biol. Chem. 265:8550–8557 (1990); Lowell et al., Biochem. J. 234:237–240 (1986)). It is of particular importance to carry out such studies with muscles undergoing denervation (disuse) atrophy or from fasted or endotoxin-treated (febrile) animals. In such tissues, overall protein breakdown is enhanced, and thus they closely mimic the human disease, but can be studied under well-defined in vitro conditions.

Inhibitors can also be administered to counter weight loss that occurs in animals or to act as growth promoters. Since they act to inhibit protein breakdown they should promote net protein accumulation and make protein synthesis more efficient in growth promotion.

Tables I–III summarize results from kinetic experiments that measured the inhibition of the 20S and 26S proteasomes, as well as cathepsin B and calpain, enzymes that may also be involved in muscle protein turnover. In these tables, $K_i$ values are reported, which are dissociation constants for the equilibrium that is established when enzyme and inhibitor interact to form the enzyme:inhibitor complex.

The substances and assay conditions are briefly summarized in the footnotes to Table I. MG 101 and MG 102, also known as Calpain Inhibitor I and II, were purchased from Calbiochem as catalogue products.

TABLE I

PROTEASE SELECTIVITY OF N-ACETYL TRIPEPTIDE ALDEHYDES

| Inhibitor | | $K_i$ (nM) | | |
|---|---|---|---|---|
| | 20 S[a] | 26 S[b] | Cat B[c] | Calpain[d] |
| MG 101 | 140 | 1,000 | 6 | 5 |

[a] Rabbit muscle. SDS-activated. Substrate: Suc—LLVY—AMC.
[b] Rabbit muscle. Substrate: Suc—Suc—LLVY—AMC—AMC. [Mg:ATP] = 2 mM.
[c] Bovine spleen. Substrate: Z—RR—AMC. [DTT] = 2 mM, [EDTA] = 5 mM, pH 5.5, T = 37° C.
[d] Rabbit muscle, 80 kD catalytic subunit. Substrate: Suc—LLVY—AMC. [CaCl$_2$] = 1 mM, [DTT] = 2 mM, pH = 7.8, T = 20° C.

TABLE II

PROTEASE SELECTIVITY OF N-CARBOBENZOXY TRIPEPTIDE ALDEHYDES[a]

| Inhibitor | | $K_i$ (nM) | | |
|---|---|---|---|---|
| | 20 S | 26 S | Cat B | Calpain |
| MG 118 | 3,800 | 28,000 | 94 | 120 |
| MG 111 | 210 | 690 | 6 | 11 |

TABLE II-continued

PROTEASE SELECTIVITY OF N-CARBOBENZOXY TRIPEPTIDE ALDEHYDES[a]

| Inhibitor | $K_i$ (nM) | | | |
|---|---|---|---|---|
| | 20 S | 26 S | Cat B | Calpain |
| MG 119 | 50 | 280 | 18 | 15 |
| MG 115 | 21 | 78 | 10 | 10 |
| MG 120 | 94 | 560 | 36 | 14 |
| MG 114 | 47 | 120 | 7 | 12 |

TABLE II-continued

PROTEASE SELECTIVITY OF N-CARBOBENZOXY TRIPEPTIDE ALDEHYDES[a]

| Inhibitor | $K_i$ (nM) 20 S | 26 S | Cat B | Calpain |
|---|---|---|---|---|
| MG 110 | 48 | 180 | 100 | 62 |
| MG 121 | 25 | 70 | 73 | 62 |

[a]Same reaction conditions as listed in footnotes of Table I.

Key points to note from Tables I–II
(1) Peptide chain length is important for inhibitory potency against the 20S proteasome: compare the $K_i$ of 47 nM for Z-Leu-Leu-Nle-H (MG 114) with the $K_i$ of 15,000 nM for Z-Leu-Nle-H (MG 105; prepared by Calbiochem as catalogue product, not shown in tables). However, with appropriate substitution, good potency can be achieved with a dipeptide aldehyde, e.g., Z-Nal-Leu-H, MG 279, $K_i$=24 nM.
(2) Potency against the 20S proteasome is also increased with increasing hydrophobicity of the N-terminal blocking group: compare the $K_i$ of 47 nM for Z-Leu-Leu-Nle-H (MG 114) with the $K_i$ of 140 nM for Ac-Leu-Leu-Nle-H (MG 101).
(3) In the series of compounds in Table II in which unbranched alkyl chain length is increased monotonically at the $P_1$ position (MG 118 (hydrogen), MG 111 (methyl), MG 119 (ethyl), MG 115 (n-propyl), and MG 114 (n-butyl)), there is a maximum of potency with Z-Leu-Leu-Nva-H (MG 115).
(4) Inhibitory potency against the 26S proteasome is always less than potency against the 20S proteasome. The difference is smallest for Z-Leu-Leu-Nva-H (MG 115; $K_{i,20S}$=21 nM and $K_{i,26S}$=78 nM), and Z-Leu-Leu-Nal-H (MG 121; $K_{i,20S}$=25 nM and $K_{i,26S}$=70 nM).
(5) The peptide aldehydes that were examined more potently inhibit cathepsin B and calpain than they inhibit the 20S and 26S proteasome, except for the two inhibitors with large, hydrophobic P, residues, Z-Leu-Leu-Phe-H and Z-Leu-Leu-Nal-H (MG 110 and MG 121, respectively).

Figure 1B:
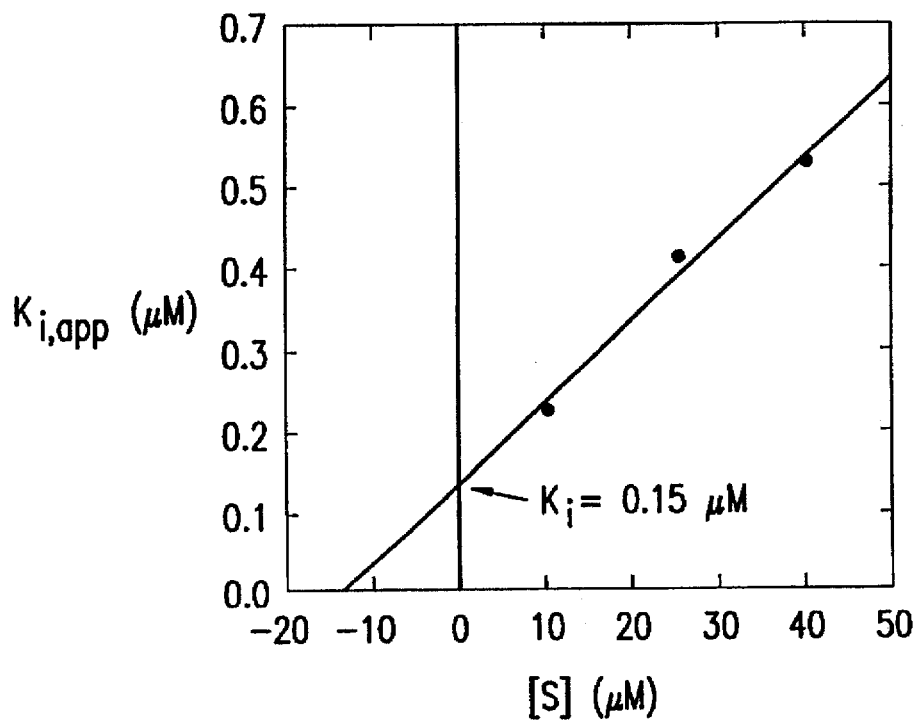
Figure 3:
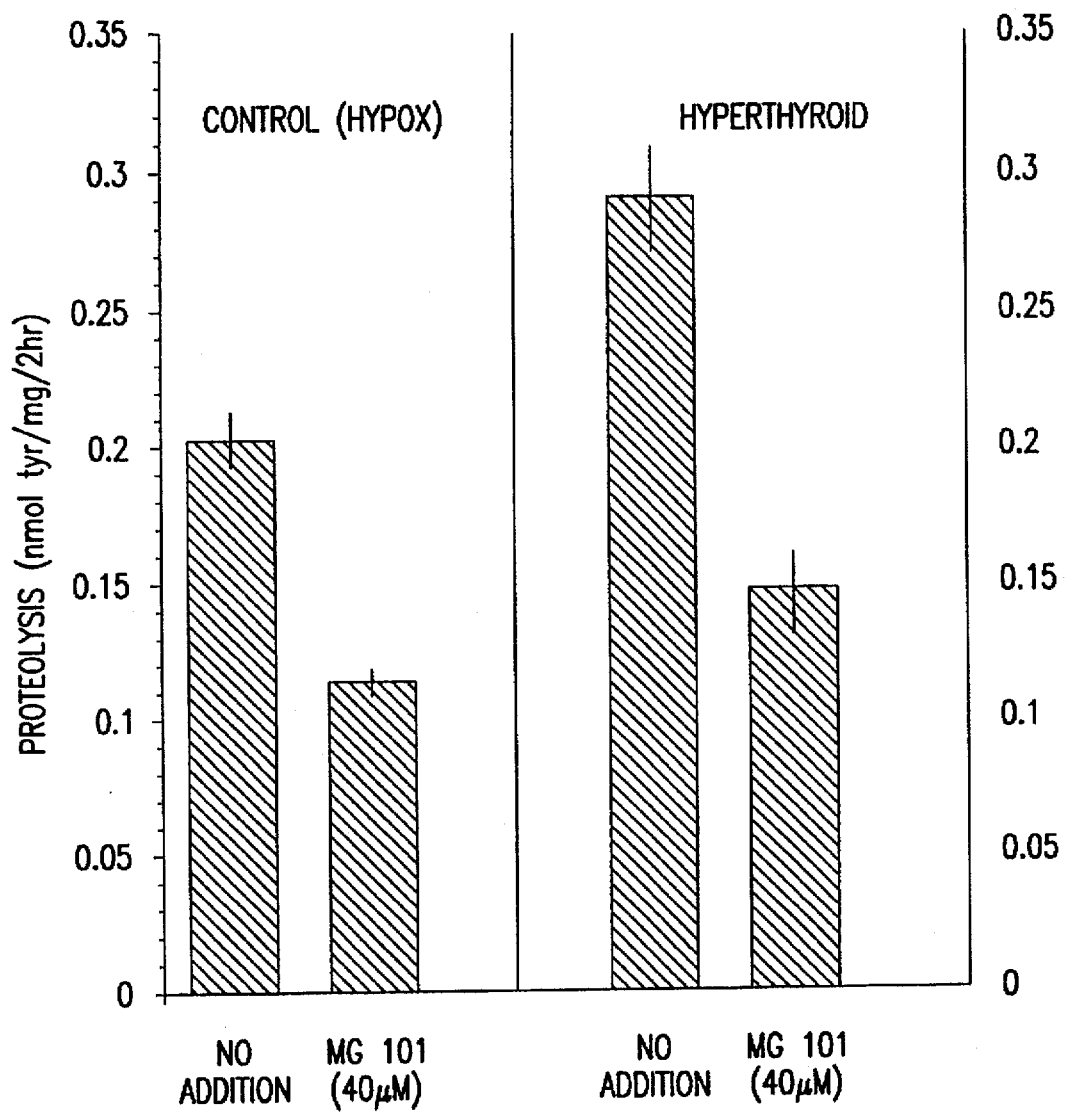
FIG. 3 is a graph depicting MG 101 inhibition of protein degradation induced by 3,5,3'-triiodothyronine (T3) in incubated rat diaphragm.
Figure 4:
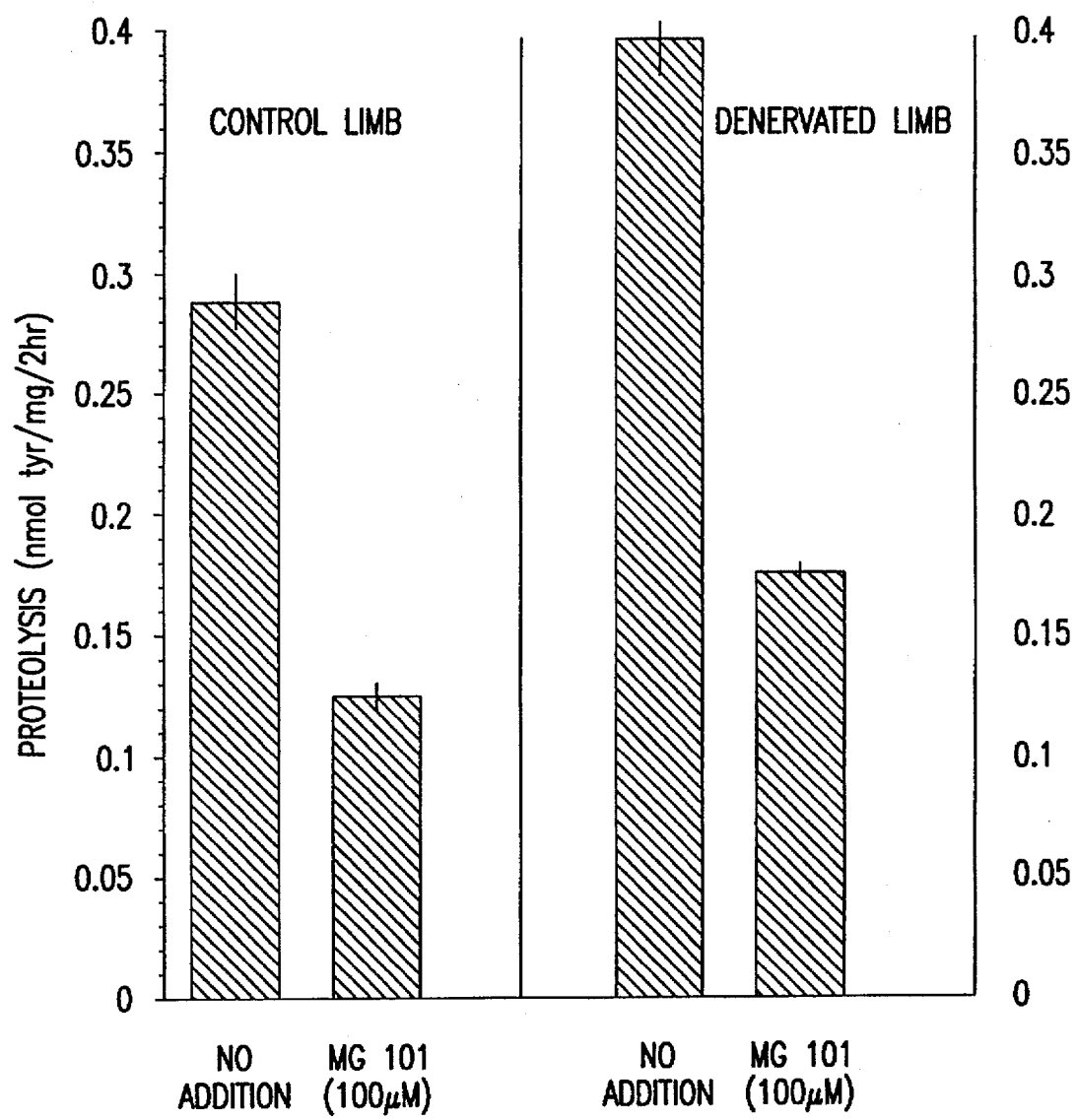
FIG. 4 is a graph depicting MG 101 inhibition of protein degradation induced by denervation in incubated rat soleus muscle.

Data show that under conditions where lysosomal proteolysis and calcium dependent proteolysis are inhibited, MG 101 inhibits the breakdown of muscle protein (FIG. 1). This is not due to generalized cell death, since this compound does not inhibit protein synthesis, nor does it significantly alter amino acid pools. Data in FIGS. 3 and 4 show that MG 101 inhibits the accelerated proteolysis in muscle caused by the administration of high levels of T3 (triiodothyronine) and by denervation of the leg muscles.

Figure 5A:
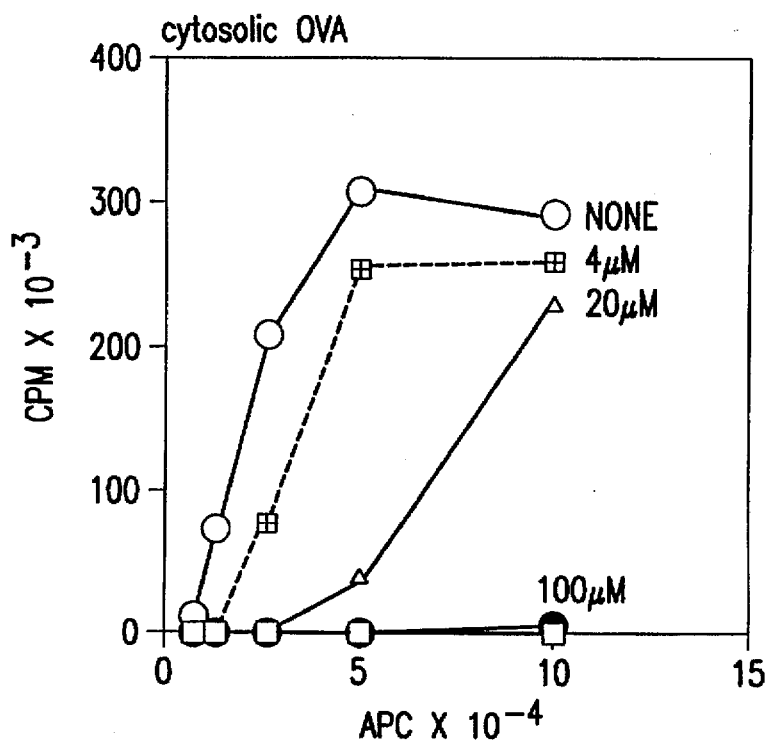
FIG. 5 is a graph showing that MG 101 inhibits presentation of antigen from ovalbumin, but not from ovalbumin peptide.
Figure 5B:
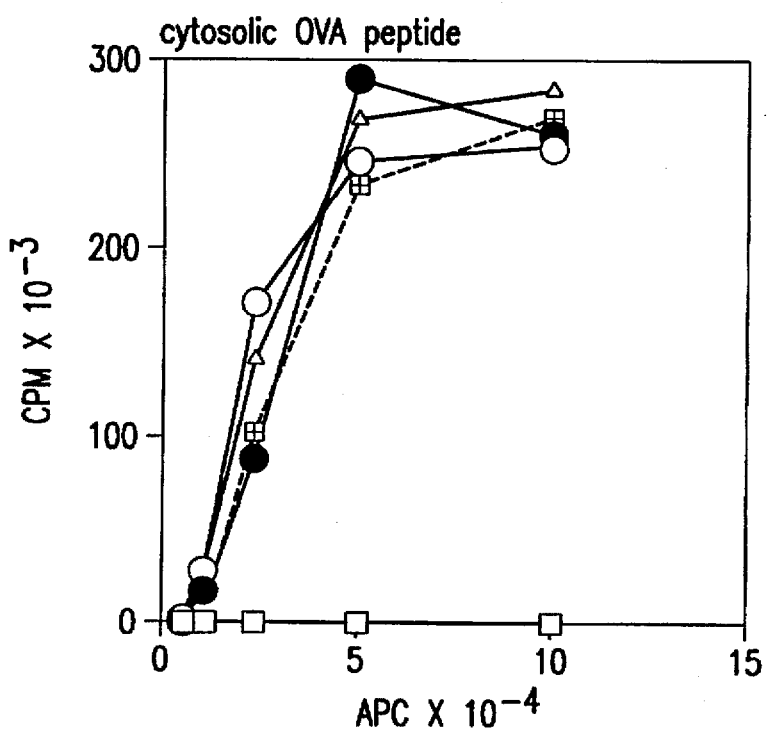
Figure 6:
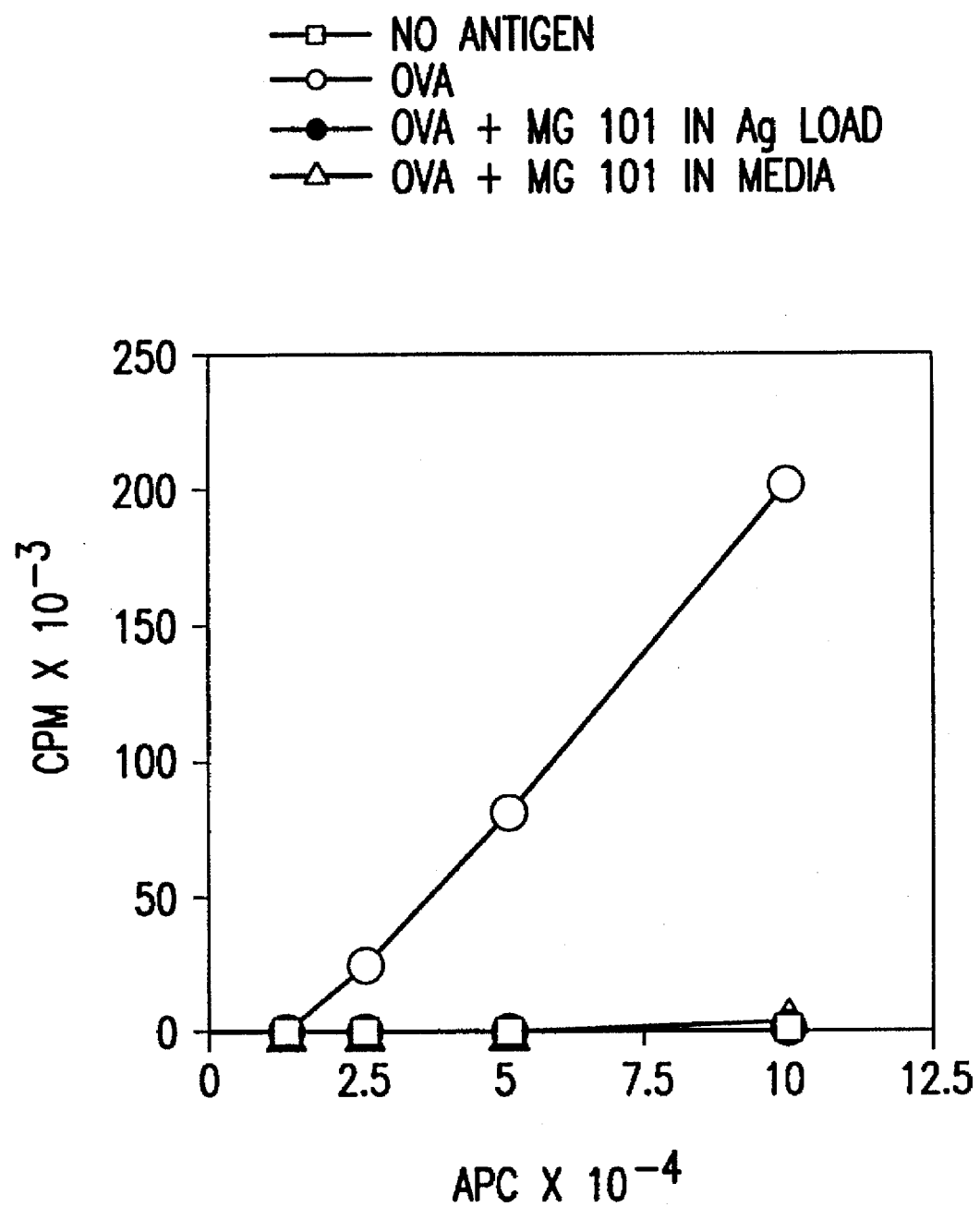
FIG. 6 is a graph showing that MG 101 inhibits presentation of antigen from ovalbumin, but not from ovalbumin peptide when incubated with intact cells.
Figure 7:
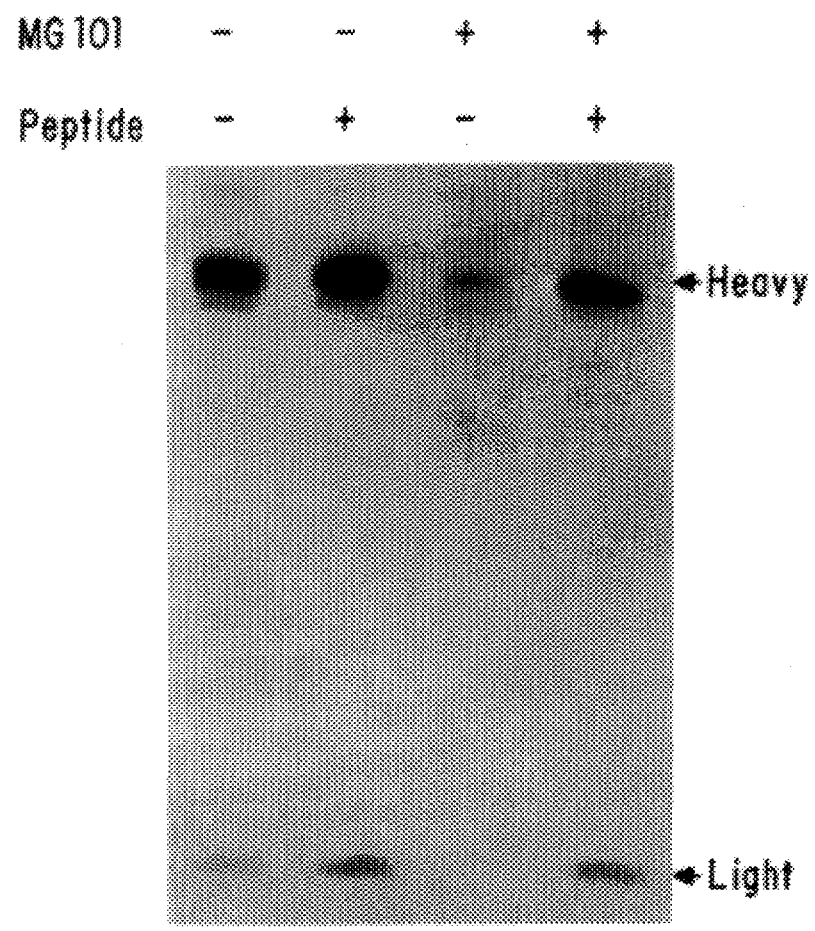
FIG. 7 shows that MG 101 blocks the appearance of MHC-I molecules on the cell surface by preventing the generation of intracellular antigens.
Figure 8:
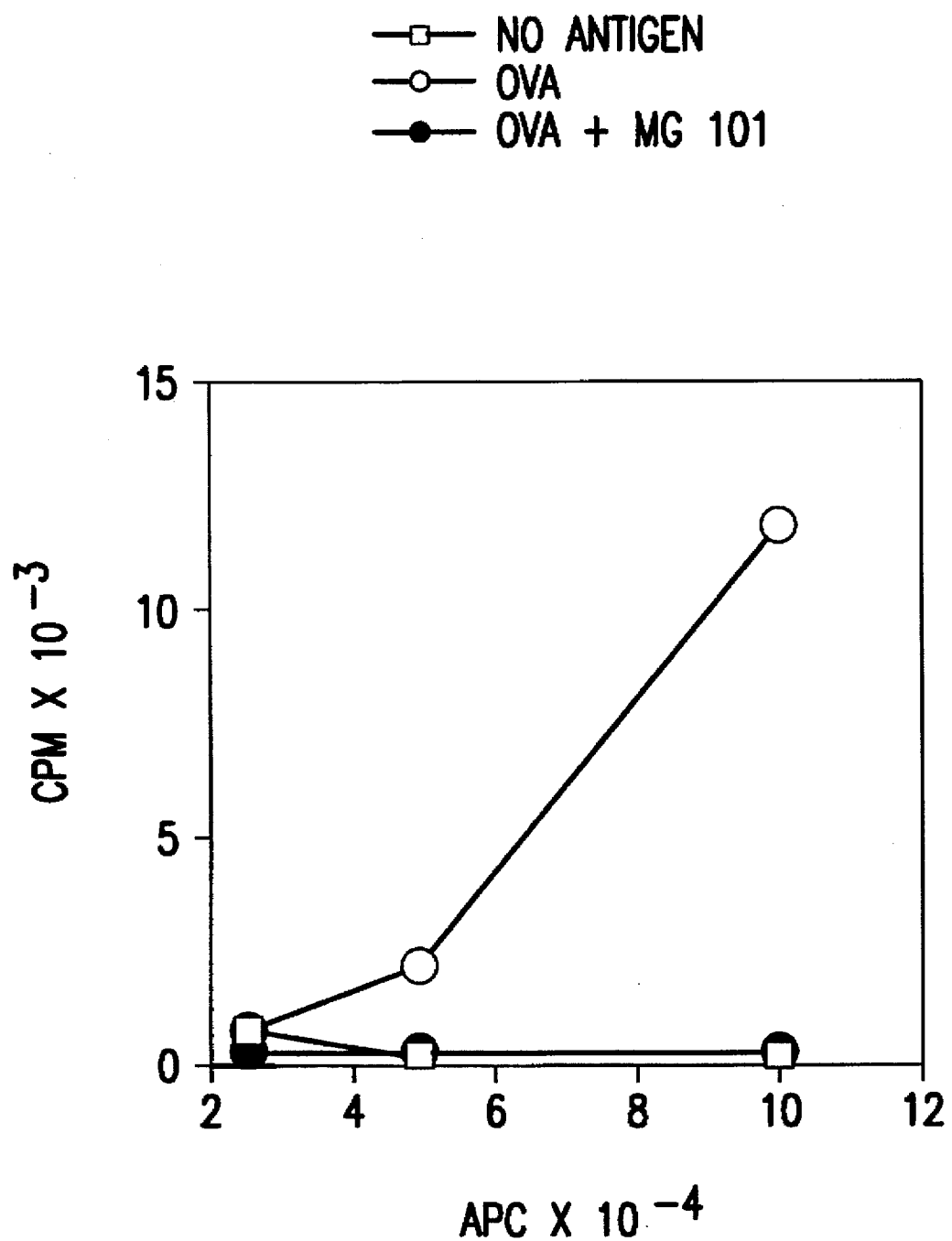
FIG. 8 is a graph showing that MG 101 inhibits presentation of antigen from ovalbumin in human cells.

Data showing that MG 101, a tripepride aldehyde, can block presentation of MHC-I restricted antigens are presented in FIGS. 5–8. Presentation of a specific peptide of ovalbumin introduced into a cell can be blocked with MG 101 (FIG. 5). MG 101 is specific for blocking the cleavage of the protein to peptides since MG 101 fails to block the presentation of the specific peptide introduced in the antigen presenting cell (FIG. 5) and can work in intact cells (FIG. 6). MG 101 has been shown to block the cleavage of peptides after both hydrophobic and basic residues. The data in FIG. 7 show that MG 101 specifically blocks the movement of functional MHC-I complexes to the cell surface. Cells lacking the MHC-I complexes on the cell surface do not participate in the cytolytic immune response. MG 101 also prevents antigen presentation in human cells (FIG. 8).

The inhibitors can be used in vitro or in vivo. They can be administered by any number of known routes, including orally, intravenously, intramuscularly, topically, and by infusion (Platt et al., U.S. Pat. No. 4,510,130; Badalamente et al., *Proc. Natl. Acad. Sci. U.S.A.* 86:5983–5987 (1989); Staubli et al., *Brain Research* 444:153–158 (1988)) and will generally be administered in combination with a physiologically acceptable carrier (e.g., physiological saline). The effective quantity of inhibitor given will be determined empirically and will be based on such considerations as the particular inhibitor used, the condition of the individual, and the size and weight of the individual. They can be administered alone or in combination with another inhibitor or an inhibitor of another pathway (e.g., a lysosomal or $Ca^{++}$-dependent pathway) responsible for loss of muscle mass.

Table III summarizes data for the inhibition of the 20S proteasome by various tripeptide aldehyde inhibitors.

Table III summarizes data for the inhibition of the 20S proteasome by various tripeptide aldehyde inhibitors.

TABLE III

Inhibition of the 20S Proteasome by Miscellaneous Peptide Aldehydes

| Compound | $K_i$ (nM) |
|---|---|
| MG 129 | 74 |
| MG 131 | 7 |
| MG 132 | 4 |
| MG 133 | 470 |

TABLE III-continued

Inhibition of the 20S Proteasome by Miscellaneous Peptide Aldehydes

| Compound | $K_i$ (nM) |
|---|---|
| MG 134 | 104 |
| MG 135 | 290 |
| MG 136 | 1,000 |
| MG 139 | 20 |
| MG 140 | 28 |

TABLE III-continued
Inhibition of the 20S Proteasome by Miscellaneous Peptide Aldehydes
| Compound | | $K_i$ (nM) |
|---|---|---|
| MG 141 | 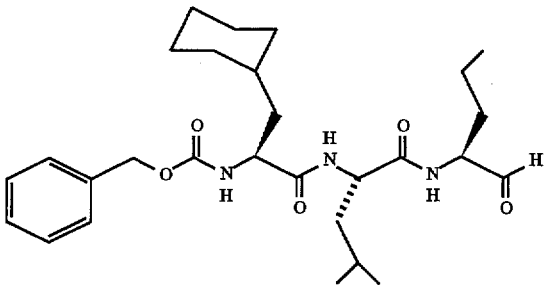 | 50 |
| MG 142 | 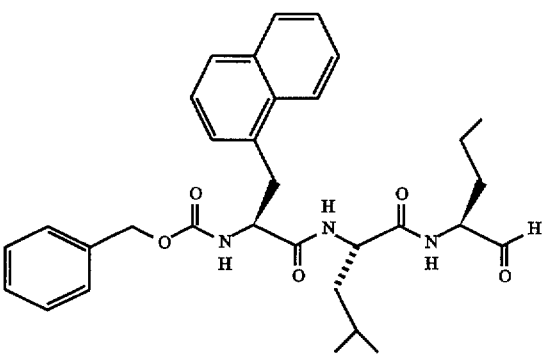 | 0.2 |
| MG 150 | 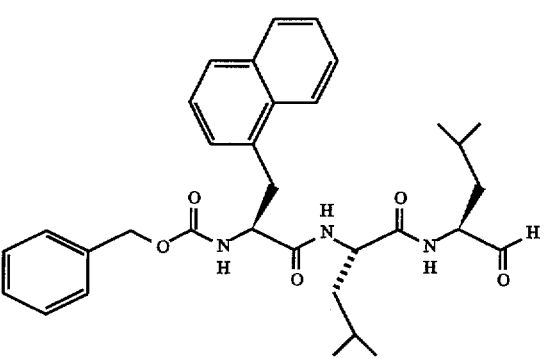 | 0.4 |
| MG 151 | 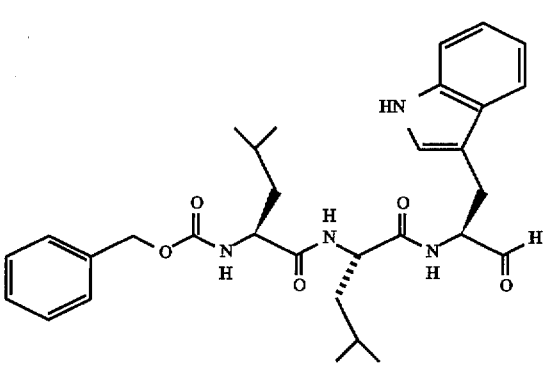 | 10 |

TABLE III-continued

Inhibition of the 20S Proteasome by Miscellaneous Peptide Aldehydes

| Compound | $K_i$ (nM) |
|---|---|
| MG 152 | 6 |
| MG 153 | 285 |
| MG 154 | 66 |
| MG 155 | 47 |

TABLE III-continued

Inhibition of the 20S Proteasome by Miscellaneous Peptide Aldehydes

| Compound | $K_i$ (nM) |
|---|---|
| MG 157 | 14 |
| MG 158 | 7 |
| MG 160 | 51 |
| MG 161 | 64 |

TABLE III-continued

Inhibition of the 20S Proteasome by Miscellaneous Peptide Aldehydes

| Compound | $K_i$ (nM) |
|---|---|
| MG 165 | 0.24 |
| MG 166 | 0.035 |
| MG 167 | 0.015 |

TABLE III-continued
Inhibition of the 20S Proteasome by Miscellaneous Peptide Aldehydes
| Compound | $K_i$ (nM) |
|---|---|
| MG 168 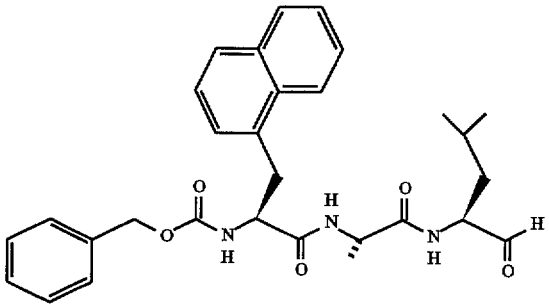 | 0.49 |
| MG 169 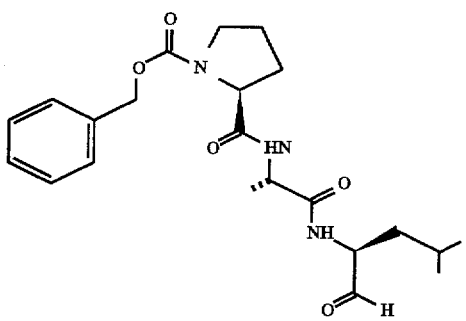 | 700 |
| MG 170 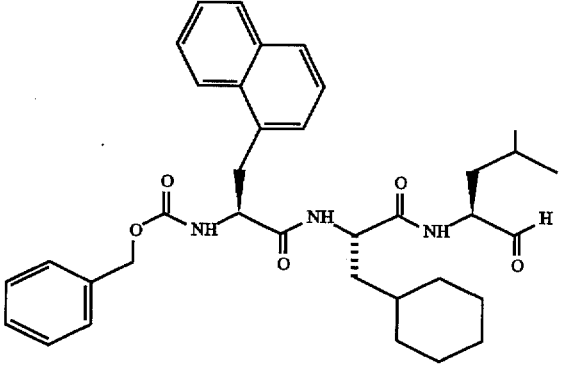 | 0.1 |
| MG 171 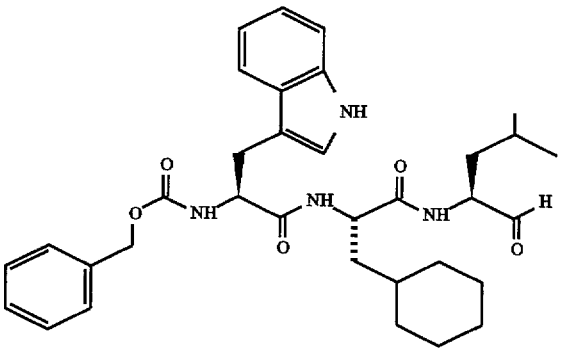 | 0.08 |

TABLE III-continued

Inhibition of the 20S Proteasome by Miscellaneous Peptide Aldehydes

| Compound | $K_i$ (nM) |
|---|---|
| MG 173 | 77 |
| MG 176 | 71 |
| MG 178 | 0.190 |
| MG 183 | 39 |

TABLE III-continued

Inhibition of the 20S Proteasome by Miscellaneous Peptide Aldehydes

| Compound | $K_i$ (nM) |
| --- | --- |
| MG 184 | 8 |
| MG 191 | 0.38 |
| MG 192 | 96 |
| MG 208 | 270 |

TABLE III-continued

Inhibition of the 20S Proteasome by Miscellaneous Peptide Aldehydes

| Compound | $K_i$ (nM) |
| --- | --- |
| MG 209 | 9.2 |
| MG 210 | 5.5 |
| MG 216 | 154 |
| MG 217 | 57 |

TABLE III-continued

Inhibition of the 20S Proteasome by Miscellaneous Peptide Aldehydes

| Compound | $K_i$ (nM) |
|---|---|
| MG 224 | 20 |
| MG 229 | 34 |
| MG 232 | 4900 |
| MG 234 | 11 |

TABLE III-continued
Inhibition of the 20S Proteasome by Miscellaneous Peptide Aldehydes
| Compound | | $K_i$ (nM) |
|---|---|---|
| MG 235 | 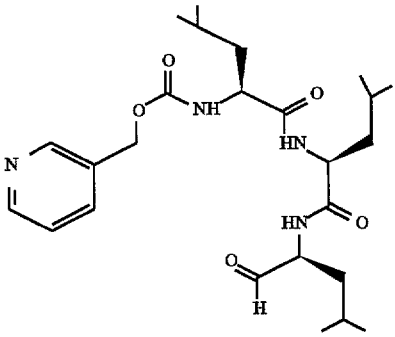 | 5.5 |
| MG 271 | 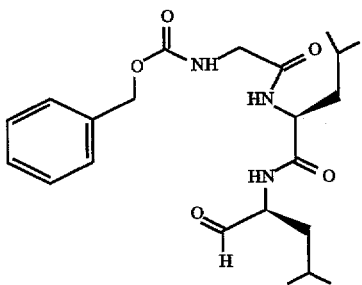 | 557 |
| MG 279 | 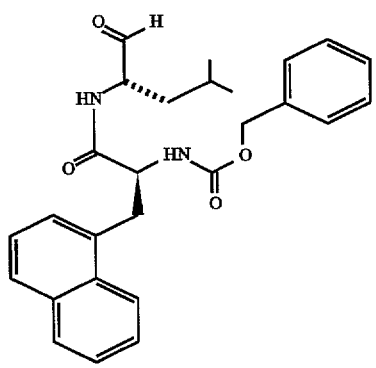 | 24 |
| MG 320 | 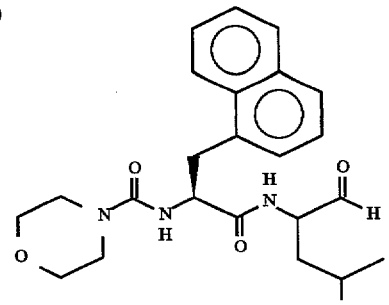 | 97 |

TABLE III-continued

Inhibition of the 20S Proteasome by Miscellaneous Peptide Aldehydes

| Compound | | $K_i$ (nM) |
|---|---|---|
| MG 355 | [structure: Cbz-Phe-Leu-al, benzyloxycarbonyl-phenylalanine-leucinal aldehyde] | 1,000 |

All of the foregoing peptides are within the scope of the present invention. The use, however, of peptides having $K_i$ values of less than about 500 nM for the 20S proteasome is preferred. It is more preferred that peptides having such $K_i$ values less than about 100 be employed in the practice of the present invention.

Use of proteasome inhibitors as agents that selectively protect normal cells from DNA damage during radiation and chemotherapy treatment of tumors The inhibitors of the present invention will block the degradation of the tumor suppressor protein p53. This protein is degraded by the ATP ubiquitin dependent proteolysis by the proteasome (see Scheffner et al., Cell 75:495–505 (1993)).

Studies of p53 knockout mice indicate an important role for p53 in reducing incidence of tumors (Donehower et al., Nature 356:215–221 (1992)). In normal cells expressing wild type, unmutated p53, the basal levels of p53 are very low owing to very rapid degradation of p53 protein. However, expression of p53 protein in normal cells is stimulated in response to radiation and drugs that induce DNA damage (Kastan et al., Cancer Res. 51:6304–63 11 (1991)). These induced high levels of wild type, unmutated p53 induce arrest of normal cell proliferation at the G1 stage of the cell cycle (Kastan et al, supra; Kuerbitz, PNAS 89:7491–7495 (1992)). This arrest of cell proliferation permits repair of damaged DNA. By contrast, in tumor cells expressing mutant forms of p53, DNA damaging drugs or radiation do not induce cell cycle arrest (Kastan et al., supra; Kastan et al., Cell 71:587–597 (1992)). Consequently, tumor cells are selectively damaged by radiation and cytotoxic drugs.

The selective arrest response of normal cells by inducing p53 suggests that enhancing the p53 response may allow the treatment of the tumor with higher/more prolonged tumorocidal doses of radiation or antineoplastic drugs. The idea that induction of p53 by a nontoxic agent as an adjunct to radiotherapy has been reported previously (Lane, Nature 358:15–16 (1992)), but a method for reducing it to practice was not described.

The use of proteasome inhibitors provides a method for augmenting the expression of p53 in normal cells by preventing its degradation by the proteasome. An example of this would be the systemic administration of proteasome inhibitor at a sufficient dose to inhibit p53 degradation by the proteasome during the treatment of the tumor with cytotoxic drugs or radiation. This will prolong and increase the levels of p53 expression in normal cells and will enhance the arrest of normal cell proliferation, reducing their sensitivity to higher doses of radiation or cytotoxic drugs. Administration of proteasome inhibitors would therefore permit exposing the tumor to higher doses of radiation, enhancing the killing of tumor cells. Thus, proteasome inhibitors can be used as adjuvants to therapy with tumorocidal agents, such as radiation and cytotoxic drugs.

Topical application of proteasome inhibitors to enhance p53 expression in skin The expression of p53 in normal skin is induced by exposure of the skin to UV irradiation, which inhibits DNA replication that is needed for cell division (Maltzman et al., Mol. Cell. Biol. 4:1689 (1984); Hall et al., Oncogene 8:203–207 (1993)). This protects normal skin from chromosomal DNA damage by allowing time for DNA repair before DNA replication.

Defects in the p53 response pathway, such as seen with Ataxia Telangiectasia, result in increased susceptibility to ionizing radiation-induced skin tumors (Kastan et al., Cell 71:587–597 (1992)). It is well established that exposure of normal individuals increases the risk for many kinds of skin cancers. This risk can be diminished by UV filtering chemicals in skin creams. Another approach would be to promote the resistance of the DNA in skin cells to UV damage by the topical application of agents that enhance the skin's expression of p53 in response to UV light. Inhibiting p53 degradation by the topical application of proteasome inhibitors provides a method to enhance the p53 response.

One preferred embodiment of the present invention is the topical application of proteasome inhibitors to reduce the acknowledged risk of skin cancers that results from the treatment of psoriasis using UV light, which is often combined with psoralens or coal tar. Each of these agents can induce DNA damage.

The present invention will now be illustrated by the following examples, which are not intended to be limiting in any way.

EXAMPLES 1–3

Preparation of Peptidyl Aldehydes

All peptidyl N,O-dimethylhydroxylamides were prepared by solution phase method using 1-ethhyl-3-(3-dimethylaminopropyl)carbodiimide hydrochloride as coupling reagent (Sheehan et al., J. Am. Chem. Soc. 87:2492–2493 (1965)). Reduction of the hydroxylamide with lithium aluminum hydride provided peptidyl aldehyde (Fehrentz et al., *Synthesis*:676–678 (1983)); Fehrentz et al., *Int. J. Peptide Protein Res.* 26:236–241 (1985)). All compounds are characterized by Proton nuclei magnetic resonance (NMR) spectroscopy. The purity of the products was verified by thin layer chromatography and, in some cases, by high performance liquid chromatography (HPLC).

EXAMPLE 1

Preparation of Z-L-leucine-L-leucine-L-norvalinal a) Boc-L-norvaline N,O-dimethylhydroxylamide 1-Ethyl-3-(3-dimethylaminopropyl)carbodiimide hydrochloride (443 mg) in one portion was added to a mixture of N-Boc-L-norvaline dicyclohexylammonium salt (838 mg), N,O-dimethylhydroxylamine hydrochloride (215 mg), 1-hydroxybenzotriazole monohydrate (340 mg), and N-methylmorpholine (0.28 ml) in dimethyl formamide (DMF, 20 ml) at 0° C. The mixture was stirred at 0° C. for 2 hours, then at room temperature for 40 hours. The reaction was quenched with water (80 mL) and the mixture was extracted with ethyl acetate (EtOAc, 3×100 mL). The combined organic layers were washed with aqueous 10% hydrogen chloride (HCl), saturated sodium bicarbonate (NaHCO$_3$), and brine, then dried over anhydrous magnesium sulfate (MgSO$_4$), filtered, and evaporated to afford the product (546 mg) as an oil.

b) Z-L-leucine-L-leucine-L-norvaline N,O-dimethylhydroxylamide

A solution of N-Boc-L-norvaline N,O-dimethylhydroxylamide (546 mg) and trifluoroacetic acid (8 mL) in methylene chloride (20 mL) was stirred at 0° C. for 3 hours. The solvent was evaporated under reduced pressure and the residue was dried under vacuum. To this flask was added Z-L-leucine-L-leucine (794 mg), 1-hydroxybenzotriazole monohydrate (340 mg), N-methylmorpholine (0.28 mL), and DMF (20mL). 1-Ethyl-3-(3-dimethylaminopropyl)carbodiimide hydrochloride (442 mg) was then added at 0° C. The mixture was stirred at 0° C. for 2 h, then at room temperature for 24 h. The reaction was quenched with water (40 mL) and the mixture was extracted with EtOAc (3×60 mL). The combined organic layers were washed with aqueous 10% HCl, saturated NaHCO$_3$, and brine, then dried over anhydrous MgSO$_4$, filtered, and evaporated to afford the product (1.09 g) as a white solid.

c) Z-L-leucine-L-leucine-L-norvalinal

A solution of Z-L-leucine-L-leucine-L-norvaline N,O-dimethylhydroxylamide (1.09 g) was dissolved in 20 mL dry tetrahydrofuran (THF) and cooled to 0° C. Lithium aluminum hydride (1M solution in THF, 3.05 mL) was added and the mixture was stirred at 0° C. for 25 minutes. Potassium bisulfate (465 mg) in 20 mL water was added and the mixture was extracted with EtOAc (3×80 mL). The combined organic layers were washed with aqueous 5% HCl, saturated NaHCO$_3$, and brine, then dried over anhydrous MgSO$_4$, filtered, and evaporated to afford the product (430 mg) as a white solid.

EXAMPLE 2

Preparation of Z-L-Leucine-L-Leucine-L-Leucinal a) Boc-L-Leucine-L-Leucine N,O-dimethylhydroxylamide A mixture of N-Boc-L-leucine-L-leucine (1 g), N,O-dimethylhydroxylamine hydrochloride (423 mg), 1-hydroxybenzotriazole monohydrate (509 mg), and N-methylmorpholine (0.42 mL) was dissolved in DMF (20 mL). 1-Ethyl-3-(3-dimethylaminopropyl)carbodiimide hydrochloride (610 mg) was added at 0° C. for 2 h, then at room temperature for 40 h. The reaction was quenched with water (80 mL) and the mixture was extracted with EtOAc (3×100 mL). The combined organic layers were washed with aqueous 10% HCl, saturated NaHCO$_3$, and brine, then dried over anhydrous MgSO$_4$, filtered, and evaporated to afford the product (923 mg) as a white solid.

b) Z-L-leucine-L-leucine-L-leucine N,O-dimethylhydroxylamide A solution of N-Boc-L-leucine-L-leucine N,O-dimethylhydroxylamide (923 mg) and trifluoroacetic acid (10 mL) in methylene chloride (20 mL) was stirred at 0° C. for 3 hours. The solvent was evaporated under reduced pressure and the residue was dried under vacuum. A portion of this product (488 mg) was transferred to another flask and was combined with Z-L-leucine (451 mg), 1-hydroxybenzotriazole monohydrate (276 mg), N-methylmorpholine (0.22 mL), and DMF (15 mL). 1-Ethyl-3-(3-dimethylaminopropyl)carbodiimide hydrochloride (357 mg) was then added at 0° C. The mixture was stirred at 0° C. for 2 h, then at room temperature for 42 h. The reaction was quenched with water (50 mL) and the mixture was extracted with EtOAc (3×60 mL). The combined organic layers were washed with aqueous 10% HCl, saturated NaHCO$_3$, and brine, then dried over anhydrous MgSO$_4$, filtered, and evaporated to afford the product as a white solid. This was further purified by silica gel chromatography (hexane/acetone 80:20, 70:30) to give the title compound (546 mg) as a white solid.

c) Z-L-leucine-L-leucine-L-leucinal

A solution of Z-L-leucine-L-leucine-L-leucine N,O-dimethylhydroxylamide (546 mg) was dissolved in 15 mL dry tetrahydrofuran (THF) and cooled to 0° C. Lithium aluminum hydride (1M solution in THF, 4.1 mL) was added and the mixture was stirred at 0° C. for 30 minutes. Potassium bisulfate (1.39 g) in 30 mL water was added and the mixture was extracted with EtOAc (3×50 mL). The combined organic layers were washed with aqueous 5% HCl, saturated NaHCO$_3$, and brine, then dried over anhydrous MgSO$_4$, filtered, and evaporated to afford the product (446 mg) as a white solid. This was further purified by reverse phase HPLC (water/acetonitrile).

EXAMPLE 3

Preparation of Z-L-(2-naphthyl)-Alanine-L-(1-naphthyl)-Alanine-L-Leucinal a) Boc-L-Leucine N,O-dimethylhydroxylamide A mixture of N-Boc-L-leucine (2.47 g), N,O-dimethylhydroxylamine hydrochloride (1.09 g), 1-hydroxybenzotriazole monohydrate (1.51 g), and N-methylmorpholine (1.21 mL) was dissolved in DMF (40 mL). 1-Ethyl-3-(3-dimethylaminopropyl)carbodiimide hydrochloride (2.14 g) was added at 0° C. and the mixture was stirred at 0° C. for 2 h, then at room temperature for 22 h. The reaction was quenched with water (100 mL) and the mixture was extracted with EtOAc (3×100 mL). The combined organic layers were washed with aqueous 10% HCl, saturated NaHCO$_3$, and brine, then dried over anhydrous MgSO$_4$, filtered, and evaporated to afford the product (2.57 g) as an oil.

b) Boc-L-(1-naphthyl)-Alanine-L-Leucine N,O-dimethylhydroxylamide

A solution of N-Boc-L-leucine N,O-dimethylhydroxylamide (983 mg) and trifluoroacetic acid (8 mL) in methylene chloride (20 mL) was stirred at 0° C. for 3 hours. The solvent was evaporated under reduced pressure and the residue was dried under vacuum. A portion of this product (208 mg) was transferred to another flask and was combined with Boc-L-(1-naphthyl)-alanine (378 mg), 1-hydroxybenzotrizole monohydrate (178 mg) N-methylmorpholine (0.15 mL), and DMF (10 mL). 1-Ethyl-3-(3-dimethylaminopropyl)carbodiimide hydrochloride (241 mg) was then added at 0° C. The mixture was stirred at 0° C. for 2 h, then at room temperature for 17 hours. The reaction was quenched with water (20 mL) and the mixture was extracted with EtOAc (3×50 mL). The combined organic layers were washed with aqueous 10% HCl, saturated NaHCO$_3$, and brine, then dried over anhydrous MgSO$_4$, filtered, and evaporated to afford the product as a white solid (459 mg).

c) Z-L-(2-naphthyl)-Alanine-L-(1-naphthyl)-Alanine-L-Leucine-N,O-dimethylhydroxylamide A solution of Boc-L-(1-naphthyl)-alanine-L-leucine N,O-dimethylhydroxylamide (459 mg), trifluoroacetic acid (5 mL), and thioanisole (2 mL) was stirred at 0° C. for 2.5 hours. The solvent was evaporated and the residue was dried under vacuum. A portion of this product (182 mg) was transferred to another flask and was combined with Z-L-(2-naphthyl)-alanine (171 mg), 1-hydroxybenzotriazole monohydrate (99 mg), N-methylmorpholine (0.08 mL), and DMF (10 mL). 1-Ethyl-3-(3-dimethylaminopropyl)carbodiimide hydrochloride (112 mg) was then added at 0° C. The mixture was stirred at 0° C. for 2 h, then at room temperature for 41 hours. The reaction was quenched with water (20 mL) and the mixture was extracted with EtOAc (3×50 mL). The combined organic layers were washed with aqueous 10% HCl, saturated NaHCO$_3$, and brine, then dried over anhydrous MgSO$_4$, filtered, and evaporated to afford the product as a white solid. This was then purified by silica gel chromatography (hexane/acetone 80:20, 70:30) to give the title compound (321 mg).

d) Z-L-(2-naphthyl)-Alanine-L-(1-naphthyl)-Alanine-L-Leucinal

Z-L-(2-naphthyl)-alanine-L-(1-naphthyl)-alanine-L-leucine-N,O-dimethylhydroxylamide (321 mg) was dissolved in 15 mL dry tetrahydrofuran (THF) and cooled to 0° C. Lithium aluminum hydride (1M, solution in THF, 1.7 mL) was added and the mixture was stirred at 0° C. for 30 minutes. Potassium bisulfate (0.59 g) in 30 mL water was added and the mixture was extracted with EtOAc (3×40 mL). The combined organic layers were washed with aqueous 5% HCl, saturated NaHCO$_3$, and brine, then dried over anhydrous MgSO$_4$, filtered, and evaporated to afford the product (274 mg) as a white solid.

EXAMPLE 4

MG 101 Inhibits Protein Degradation in Incubated Rat Diaphragm

Figure 2:
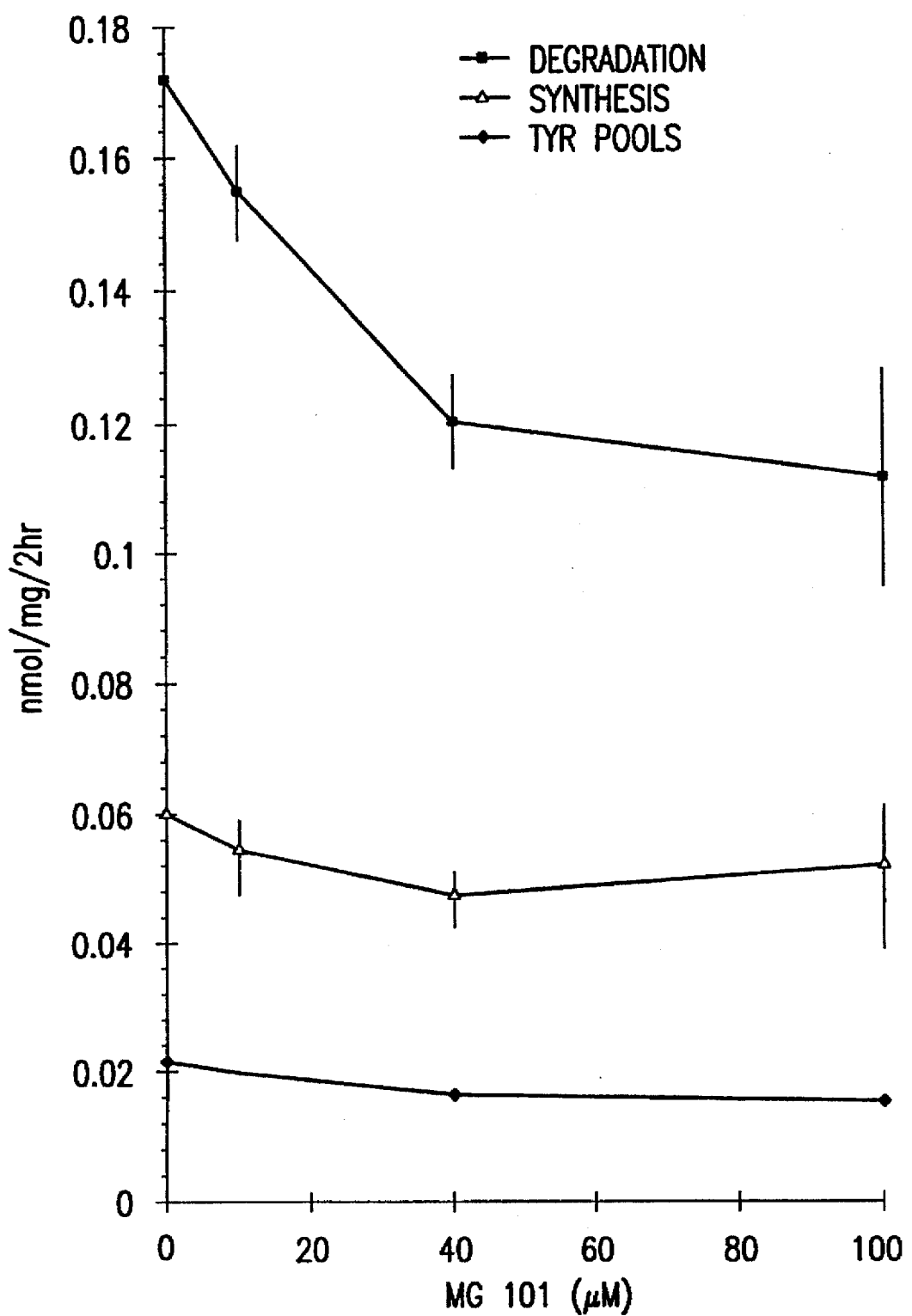
FIG. 2 is a graph depicting MG 101 inhibition of protein degradation in incubated rat diaphragm.

Rat diaphragm muscle was cut into quarters and incubated in medium containing a mixture of amino acids, insulin, inhibitors of lysosomal and calcium dependent proteolysis, and MG 101 at the concentrations shown in FIG. 2. After 1 hour, $^3$H-phenylalanine was added and the incubation continued for 2 hours. Under these conditions, the ATP-dependent ubiquitin pathway is largely responsible for muscle protein degradation. After incubation, the tissue was homogenized and free tyrosine of the homogenate and medium was assayed separately. $^3$-phenylalanine incorporation into protein was also measured. Values are the means +SE of data from 7 animals. Protein synthesis was calculated from the incorporation of $^3$H-phenylalanine, and net protein breakdown was calculated from the release of tyrosine into the incubation medium. The total rate of protein breakdown is calculated from the equation:

Total protein breakdown=Net protein breakdown+Protein synthesis

EXAMPLE 5

MG 101 Inhibits T3 Induced Protein Degradation in Incubated Rat Diaphragm

T3 was administered to hypophysectomized rats for 7 days. This treatment resulted in marked atrophy of rat skeletal muscle. Rat diaphragm muscle from treated and untreated rats was cut into quarters and incubated in medium containing a mixture of amino acids, insulin, inhibitors of lysosomal and calcium dependent proteolysis, and 40 µM MG 101. After 1 hour, $^3$-phenylalanine was added and the incubation continued for 2 hours. Under these conditions, the ATP-dependent ubiquitin pathway is largely responsible for muscle protein degradation. After incubation, the tissue was homogenized, and $^3$-phenylalanine incorporation into protein and free tyrosine of the medium was measured. Values are the means±SE of data from 7 animals. See FIG. 3. Protein synthesis was calculated from the incorporation of $^3$-phenylalanine, and net protein breakdown was calculated from the release of tyrosine into the incubation medium. The total rate of protein breakdown is calculated from the equation:

Total protein breakdown=Net protein breakdown +Protein synthesis

EXAMPLE 6

MG 101 Inhibits Denervation-Induced Protein Degradation in Incubated Rat Soleus Muscle One leg of each of seven rats was denervated by section of the sciatic nerve 3 days prior to sacrifice. This treatment resulted in marked atrophy of the muscles of the denervated leg. Rat soleus muscles were attached by the tendons to wire supports to maintain them at physiological rest length, and were incubated in medium containing a mixture of amino acids, insulin, inhibitors of lysosomal and calcium dependent proteolysis, and 100 µM MG 101. After 1 hour, $^3$-phenylalanine was added and the incubation continued for 2 hours. Under these conditions, the ATP-dependent ubiquitin pathway is largely responsible for most muscle protein degradation. After incubation, the tissue was homogenized, and $^3$-phenylalanine incorporation into protein and free tyrosine of the medium was measured. Values are the means±SE of data from 7 animals. See FIG. 4. Protein synthesis was calculated from the incorporation of $^3$-phenylalanine, and net protein breakdown was calculated from the release of tyrosine into the incubation medium. The total rate of protein breakdown is calculated from the equation Total protein breakdown=Net protein breakdown+Protein synthesis

EXAMPLE 7

MG 101 Inhibits Presentation of Antigen from Ovalbumin, But Not from Ovalbumin Peptide Antigen-presenting cells (APCs)—mouse B lymphoblastoid cell line (LB27.4)—were washed free of serum and loaded with an ovalbumin peptide (residues 257–263), which corresponds to the sequence these cells naturally generate and present. The APCs were incubated 1 hr at 37° C., electroporated with antigen, incubated 10 min on ice and washed. The antigen loaded cells were incubated 2 hrs at 37° C., fixed with paraformaldehyde, and washed. MG 101 at the concentrations indicated in FIG. 5 was present in all the steps prior to fixation. APCs were assayed for antigen presentation as described in Rock et al., *J. Immunol.* 145:804–811 (1990) and Carbone et al., *J. Exp Med.* 171:377–387 (1990). FIG. 5 shows MHC-I presentation of ovalbumin (OVA, left panel) and an ovalbumin peptide (right panel). In the left panel, APCs were treated with (open circles) or without (closed circles) MG 101 and electroporated with ovalbumin. In the right panel, APCs were treated with (open circles) or without (closed circles) MG 101 and electroporated with ovalbumin peptide.

The left panel demonstrates that MG 101 inhibits the presentation of ovalbumin with class I MHC molecules. The right panel demonstrates that MG 101 does not inhibit the presentation of electroporated peptide. This result indicates that the inhibition of antigen presentation is occurring through MG 101 inhibition of the processing of the ovalbumin protein into the ovalbumin peptide.

EXAMPLE 8

MG 101 Inhibits Presentation of Antigen from Ovalbumin, But Not from Ovalbumin Peptide When Incubated with Intact Cells Conditions were the same as in Example 7, except that (1) in one group of cells (referred to as MG 101 in media) MG 101 (50 μM) was omitted from the antigen load while in a parallel group (referred to as MG 101 in Ag load) MG 101 (50 μM) was included in the antigen load; and (2) OVA was introduced into the cytoplasm by hypotonic lysis of pinosomes (3) instead of electroporation. By not altering the integrity of the plasma membrane, the inhibition seen in the "MG 101 in media group" indicates that the agent can enter into living cells and inhibit antigen processing. See FIG. 6.

EXAMPLE 9

MG 101 Blocks the Appearance of MHC-I Molecules on the Cell Surface by Preventing the Generation of Intracellular Antigens Class I MHC molecules are peptide-binding receptors composed of a heavy and a light chain. Peptide binding to these molecules is essential for the stable association of the heavy and light chains. If cells fail to generate peptides for class I molecules, heavy and light chains are synthesized, but do not stably assemble and largely fail to get transported to the cell surface.

To test the effect of MG 101 on class I assembly, RMA cells were incubated with and without MG 101 (100 μM) for 1 hr at 37° C., electroporated with and without MG 101 (100 μM) as described in Example 7, and incubated with and without MG 101 (100 μM) for 3 hrs at 37° C. Over the last 30 min of incubation the cells were pulse labeled with $^{35}$S-methionine and were then washed and detergent lysates were prepared. Lysates were divided and class I binding peptides were added to one group. Class I molecules were immunoprecipitated with a mAb, Y3 (Townsend et al., *Cell* 62:285–295 (1990)), that only reacts with assembled class I heterodimers and analyzed as previously described (Michalek et al., *Nature* 363:552–554 (1993)). In the presence of MG 101, the assembly of class I heterodimers is markedly reduced. Control experiments show that MG 101 does not affect the level of the individual subunits. MG 101 fails to inhibit complex formation from introduced antigenic peptide (lane 4). See FIG. 7.

EXAMPLE 10

MG 101 Inhibits Presentation of Antigen from Ovalbumin in Human Cells

Example 7 was repeated except that the human cell line RAJI-K$^b$ was used. The results are shown in FIG. 8.

Summary of Enzyme Inhibition by MG 101

MG 101 inhibits peptidase activities of both latent and active forms of 20S proteasome activity ($K_i$=0.14 to 7 μM).

Inhibition by MG 101 conforms to a simple kinetic model of a competitive inhibitor.

MG 101 inhibits protein degradation by the 20S proteasome ($K_i$=7 μM).

MG 101 inhibits 26S proteasome complex activity ($K_i$= 2.9 μM).

MG 101 is a starting point for mechanism-based medicinal chemistry strategy.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A method for reducing the rate of loss of muscle mass in an animal comprising contacting cells of the muscle with a proteasome inhibitor of the structure:

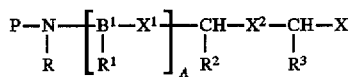

where

P is an amino-group-protecting moiety;

B$^1$ at each occurrence is independently selected from the group consisting of

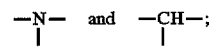

X is selected from the group consisting of

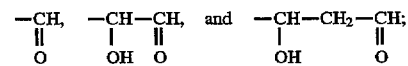

X$^1$ at each occurrence and X$^2$ are independently selected from the group consisting of

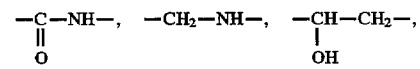

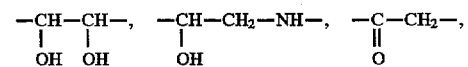

-continued $$-\underset{\underset{O}{\overset{O}{\|}}}{\overset{\|}{S}}-NH-, \quad -\underset{\underset{O}{\overset{O}{\|}}}{\overset{\|}{S}}-CH_2-, \quad -\underset{OH}{\overset{|}{C}}H-CH_2-\overset{O}{\overset{\|}{C}}-NH-, \text{ and}$$

$$-CH=CH-$$

except that if $B^1$ is $$-\overset{|}{N}-,$$

then $X^1$ must be $$-\overset{O}{\overset{\|}{C}}-NH-;$$

R is hydrogen or together with the adjacent $R^1$, or $R^2$ if A=0, forms a nitrogen-containing heterocyclic ring; $R^1$ at each occurrence, $R^2$, and $R^3$ are independently selected from the group consisting of hydrogen, alkyl, cycloalkyl, alkenyl, alkynyl, aryl, and $-CH_2-R^4$, where $R^4$ is aryl, aralkyl, alkaryl, cycloalkyl or $-Y-R^5$, where Y is a chalcogen, and $R^5$ is alkyl; and A is 0, 1, or 2; and wherein, stereochemically, $B^1-R^1$ is D, L, or a mixture thereof and $CH-R^2$ and $CH-R^3$ are independently L or a mixture of D and L.

2. The method of claim 1 wherein P is $$R^7-R^6$$

where $R^6$ is $$-\overset{O}{\overset{\|}{C}}- \quad \text{or} \quad -\underset{\underset{O}{\overset{O}{\|}}}{\overset{\|}{S}}-$$

and $R^7$ is alkyl, aryl, alkaryl, aralkyl, alkoxy, alkaryloxy, aralkoxy or a heterocyclic moiety.

3. The method of claim 2 wherein $X^1$ and $X^2$ are $$-\overset{O}{\overset{\|}{C}}-NH-$$

4. The method of claim 3 wherein A is 1 or 2 and $B^1$ is $$-\overset{|}{C}H-$$

5. The method of claim 4 wherein $R^3$ is isobutyl.

6. The method of claim 4 wherein $R^1$ at each occurrence and $R^2$ are independently selected from the group consisting of alkyl and $-CH_2-R^4$, where $R^4$ is cyclohexyl or naphthyl.

7. The method of claim 6 wherein $B^1-R^1$, $CH-R^2$, and $CH-R^3$ are all of the L configuration.

8. The method of claim 1 wherein the proteasome inhibitor is selected from the group consisting of Ac—Leu—Leu—Nle—H Z—Leu—Leu—Val—H -continued Z—Leu—Leu—Nle—H Z—Leu—Leu—Phe—H Z—Leu—Leu-2-Nal—H Z—Leu—Leu—Gly—H Z—Leu—Leu—Ala—H Z—Leu—Leu—Abu—H Z—Leu—Leu—Nva—H Z—Leu—Leu—Tyr—H Z—Leu—Leu—Leu—H Z—Leu—Leu—Ile—H Z—Leu—Leu—NH—CH—CHO
                    |
                    CH₂—⬡—S Z—Leu—Leu—NH—CH—CHO
                    |
                    ⬡ (phenyl)

Z—Leu—Leu—Trp—H

Z—Leu—Leu—NHCHCHO
              |
              CH₂—⬡—NO₂

Z—Leu—Leu—NH—CH—CHO
                    |
                    CH₂—CH₂—⬡

Z—Leu—Leu—NH—CH—CHO
                    |
                    CH₂
                    |
            CH₃—C—CH₃
                    |
                    CH₃

Z—Leu—Leu—NH—CH—CHO
                    |
                    CH₂—CH=CH₂

Z—Leu—Leu—NH—CH—CHO
                    |
                    CH₂—C≡CH $$Z-NH-\underset{\underset{\underset{S}{\overset{}{\bigcirc}}}{\overset{|}{CH_2}}}{\overset{|}{C}H}-\overset{O}{\overset{\|}{C}}-Leu-Nva-H$$

-continued
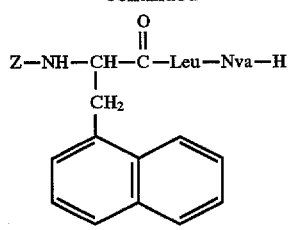
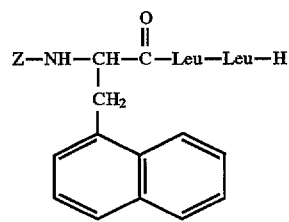
Z—Leu—Leu—NH—CH—CHO
              |
              CH₂
              |
              (4-OCH₃-phenyl)
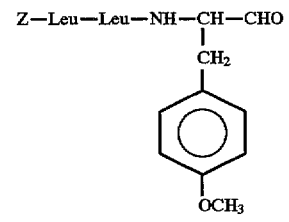
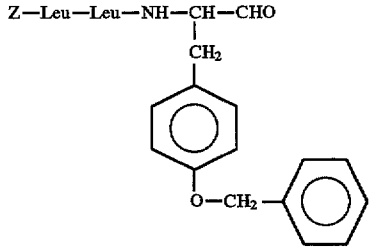
Ac—Leu—Leu—Leu—H
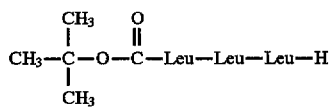
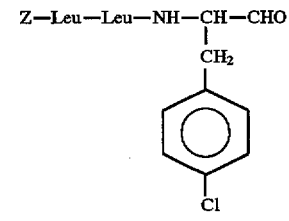
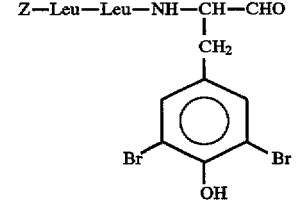
-continued
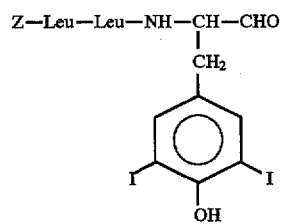
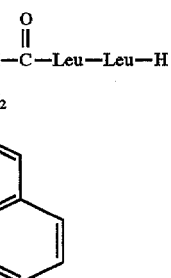
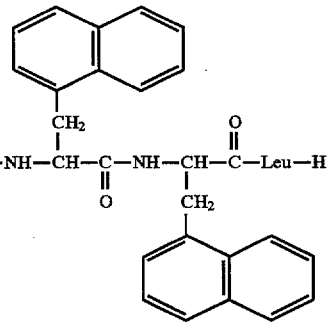
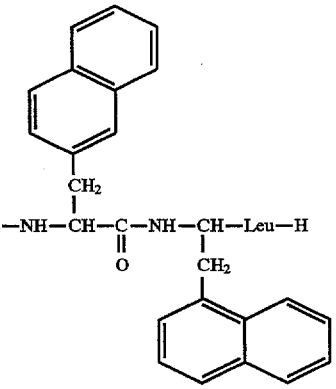
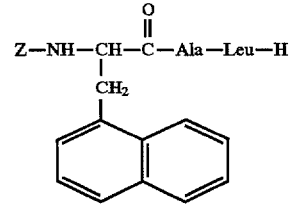
Z—Pro—Ala—Leu—H

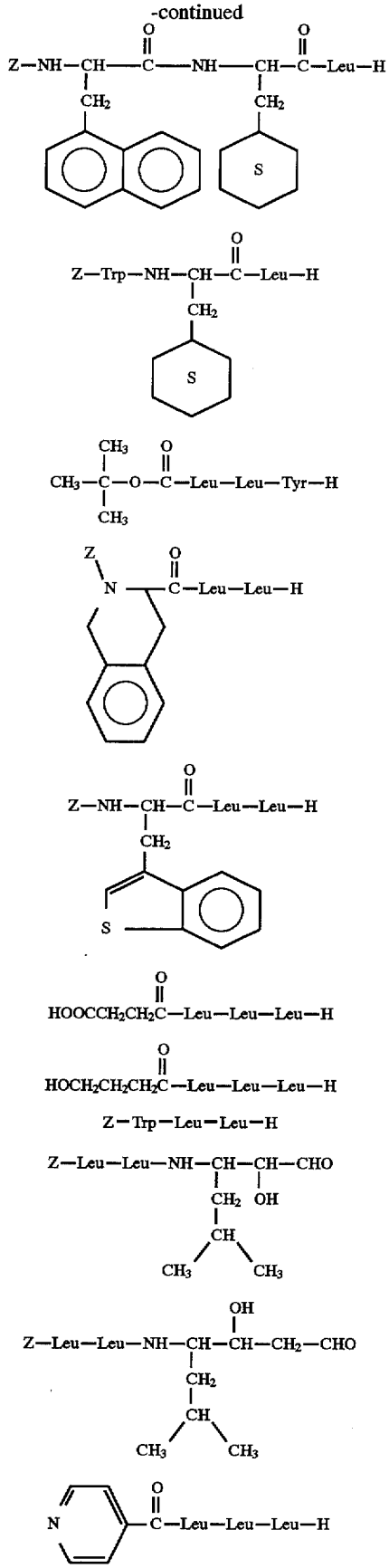
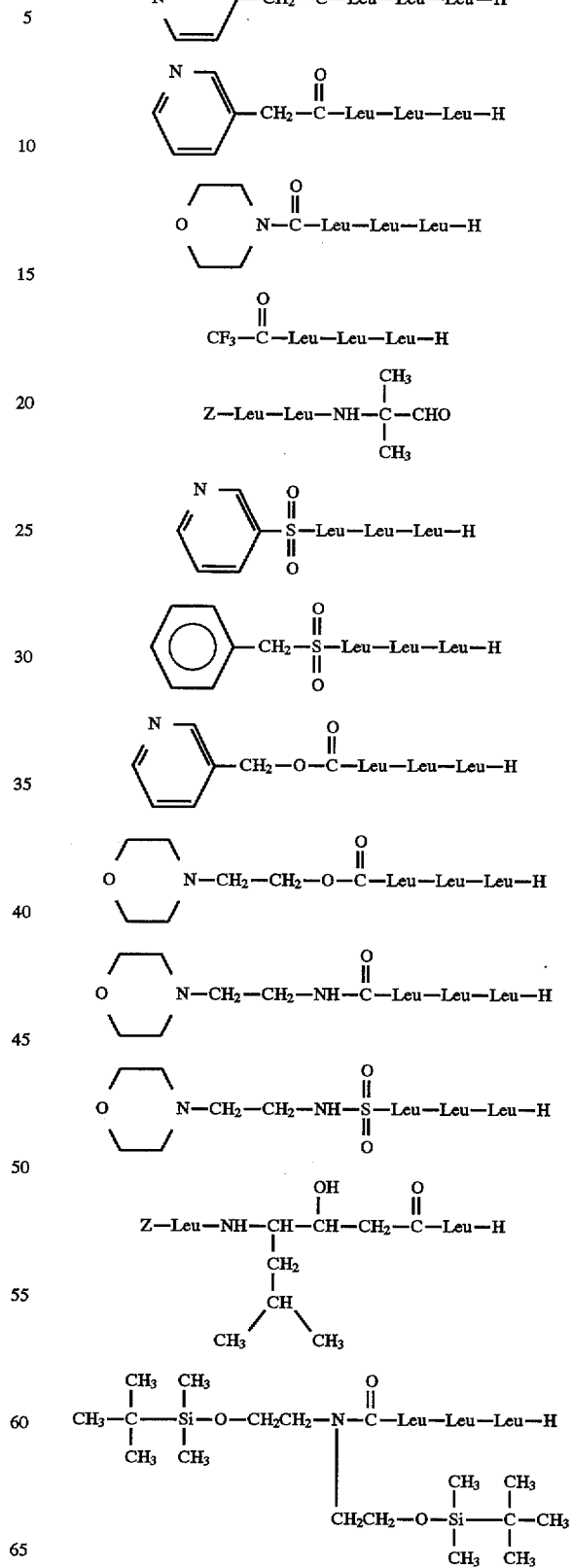

-continued
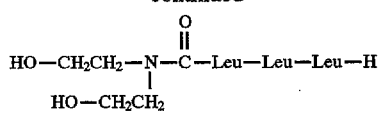
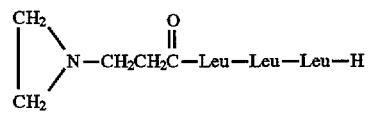
Z—Leu—Leu—Pro—H
Z—Gly—Leu—Leu—H
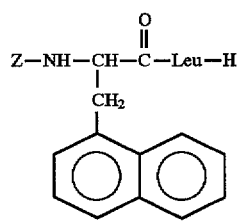
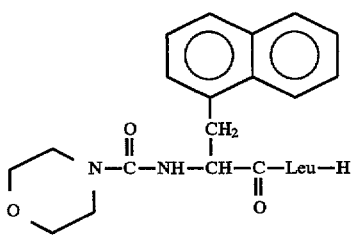
Z—Phe—Leu—H
and
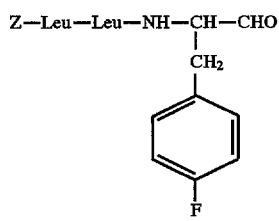
where:
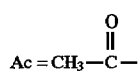
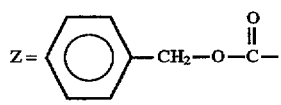
2-Nal = 2-Naphthylalanine
9. The method of claim 1 wherein the proteasome inhibitor is selected from the group consisting of
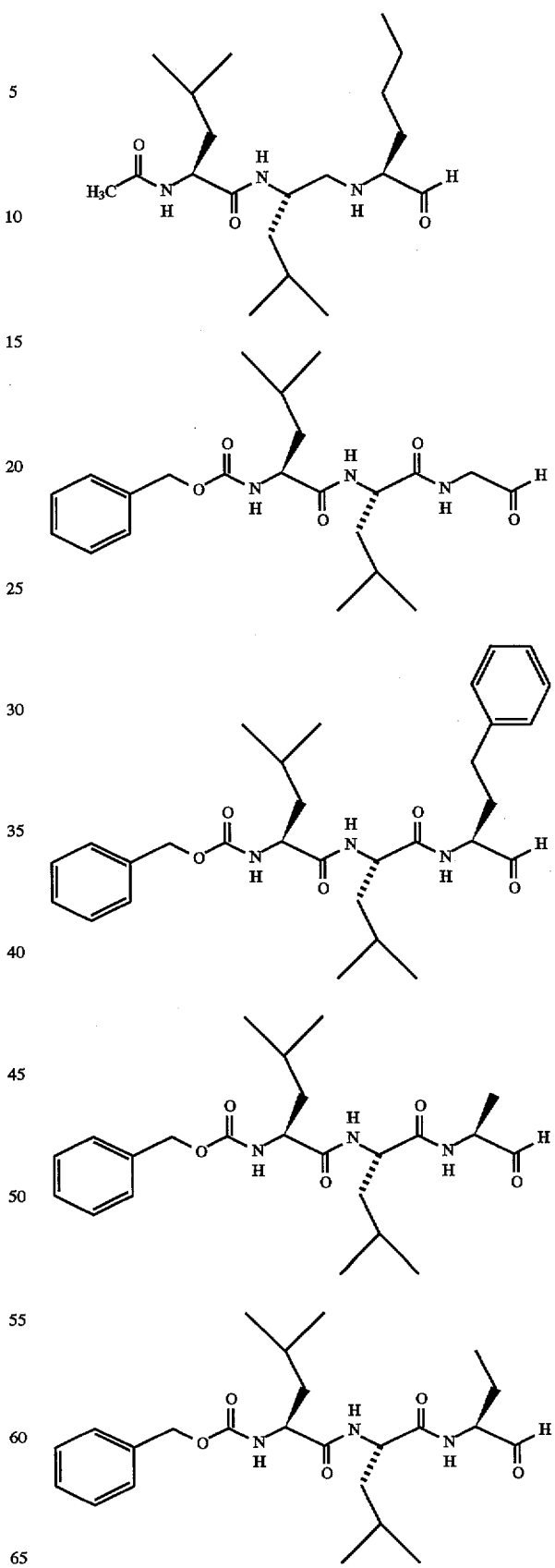

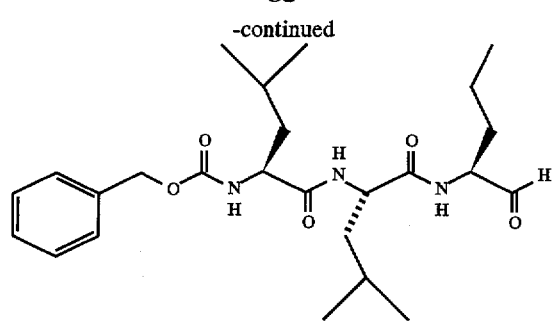
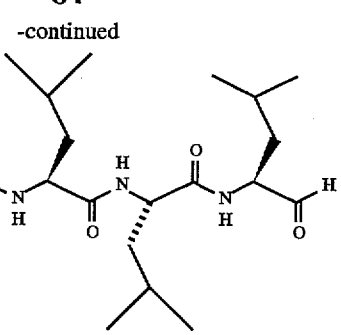
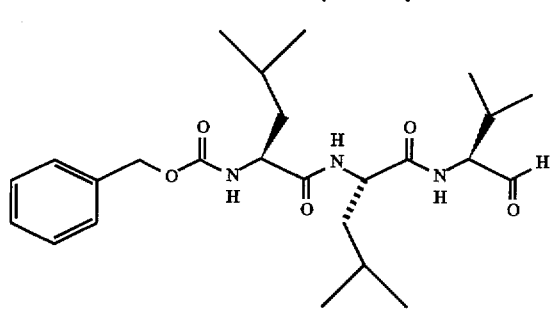
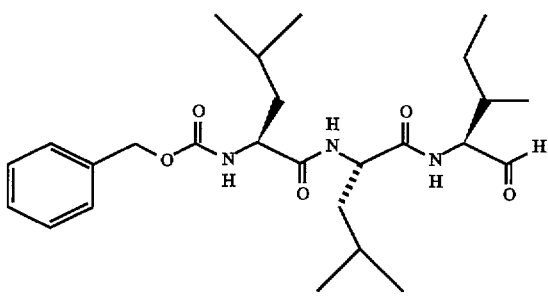
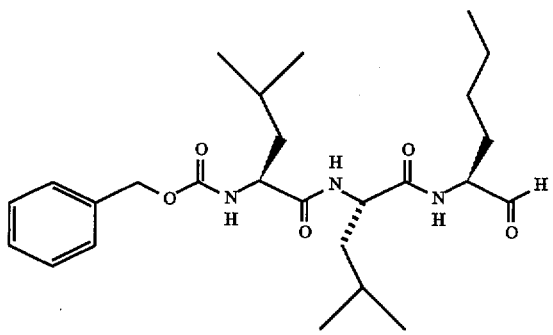
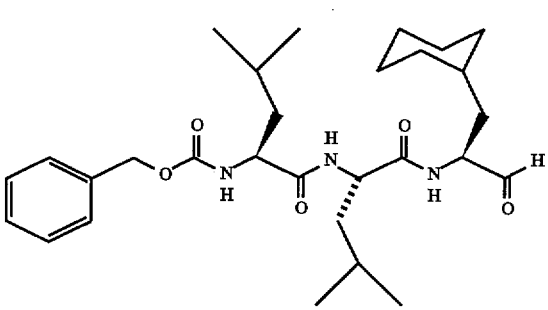
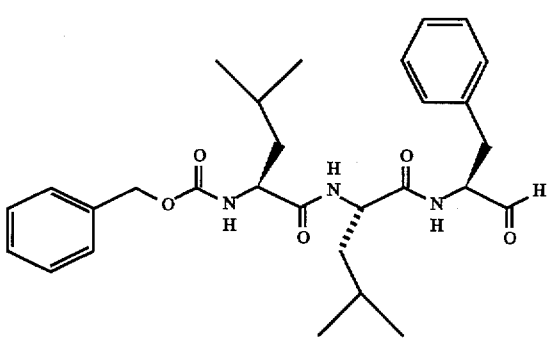
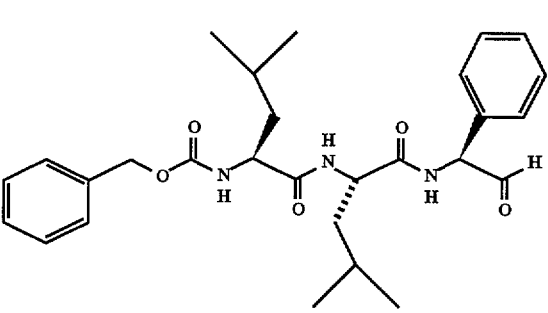
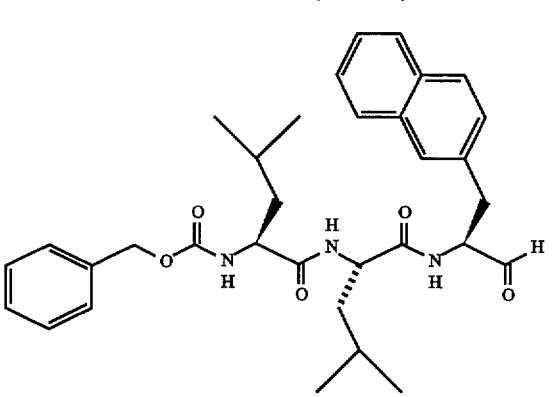
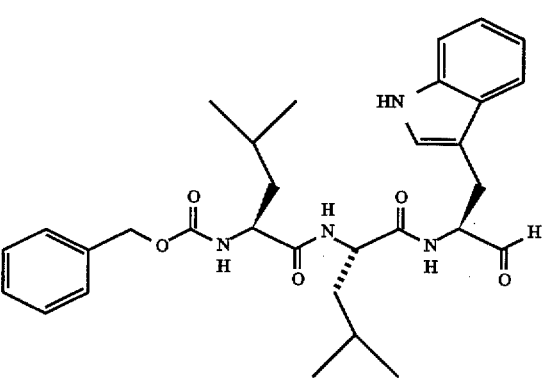

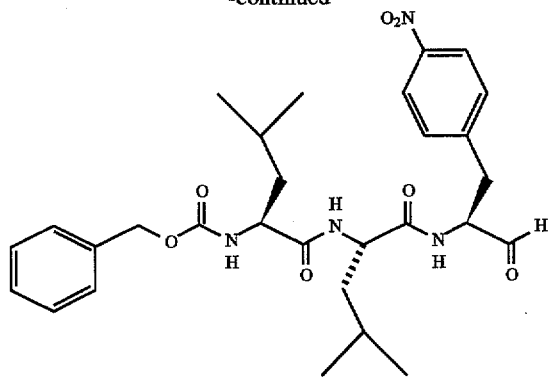
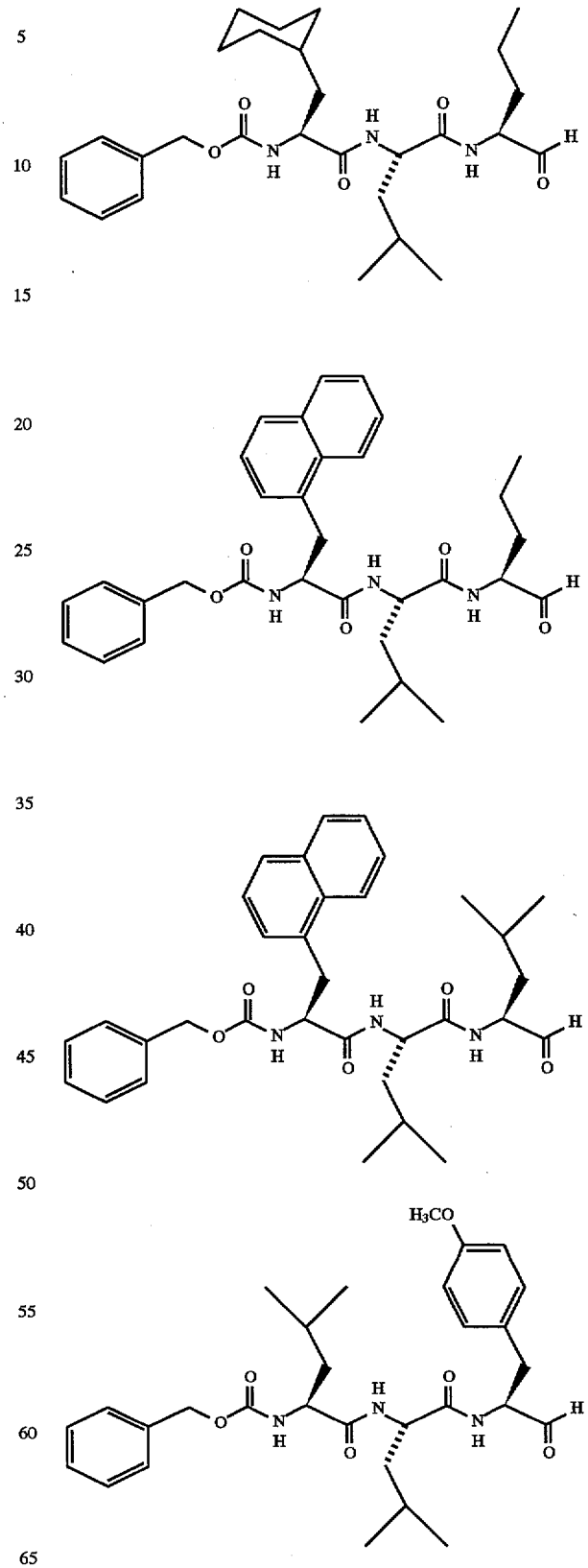

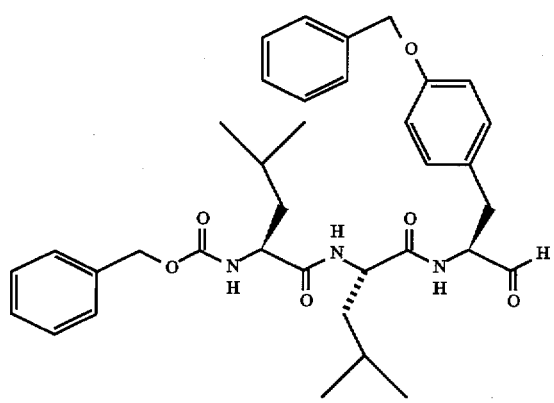
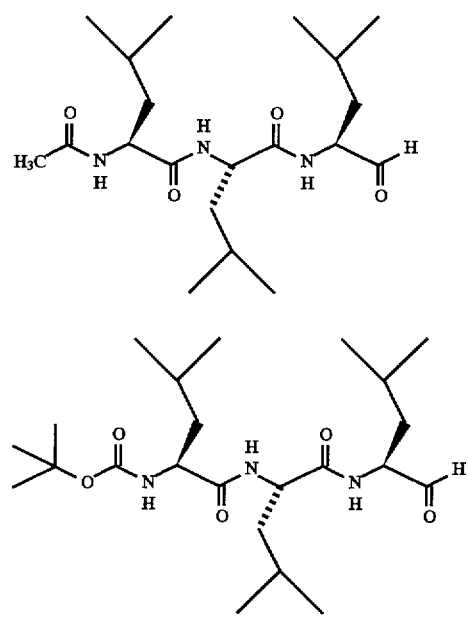
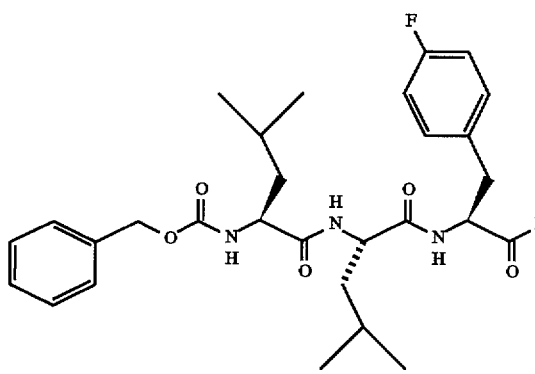
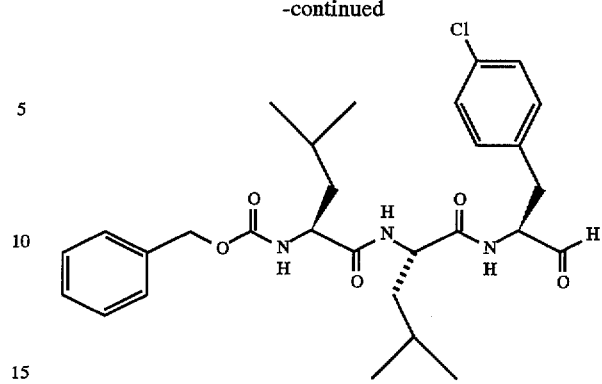
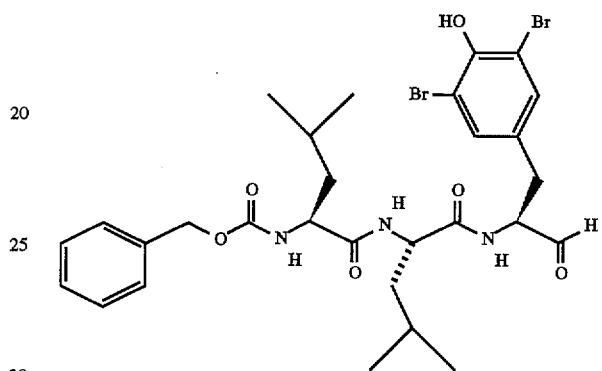
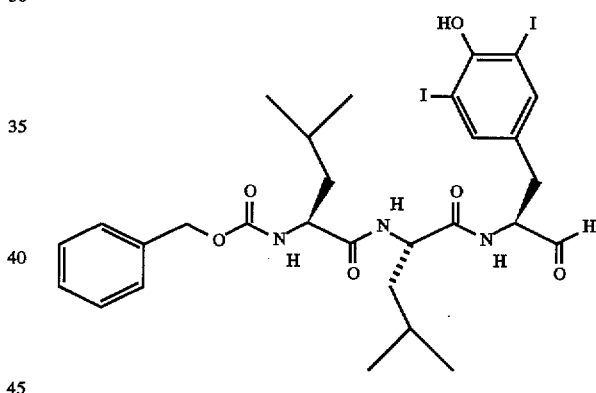
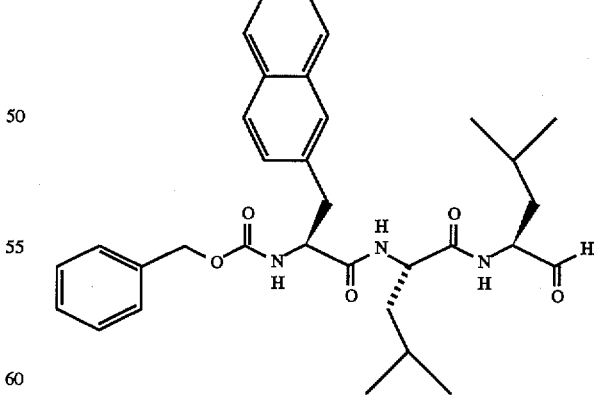

89
-continued
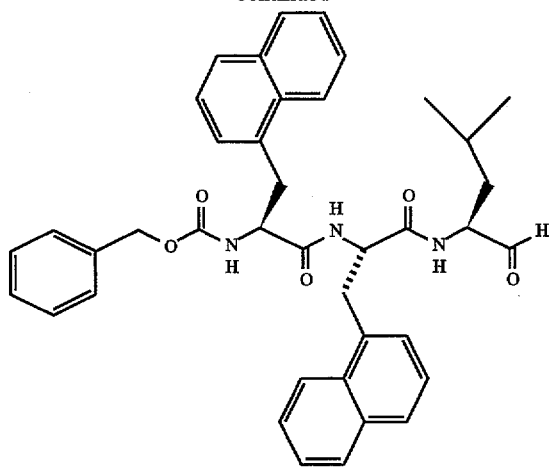
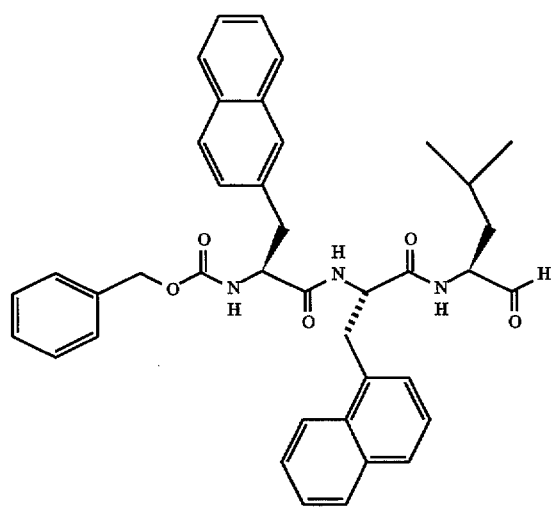
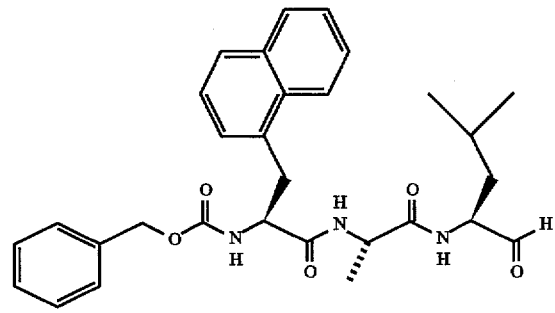
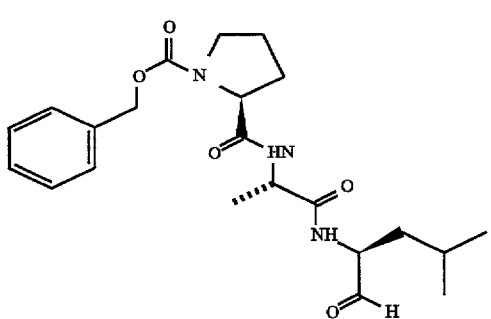
90
-continued
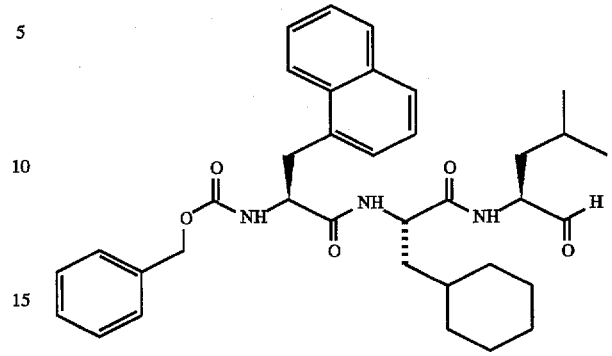
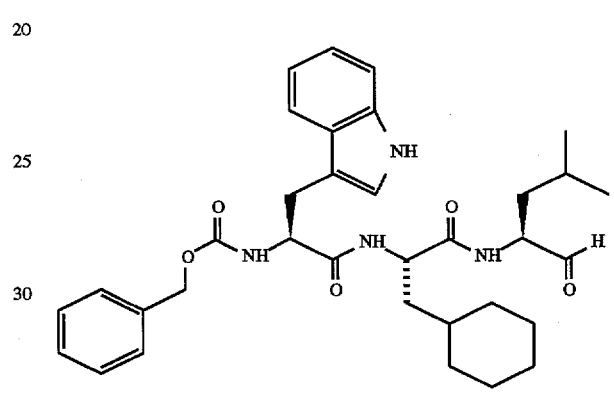
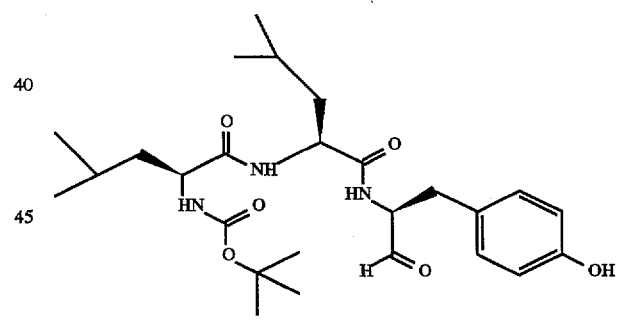
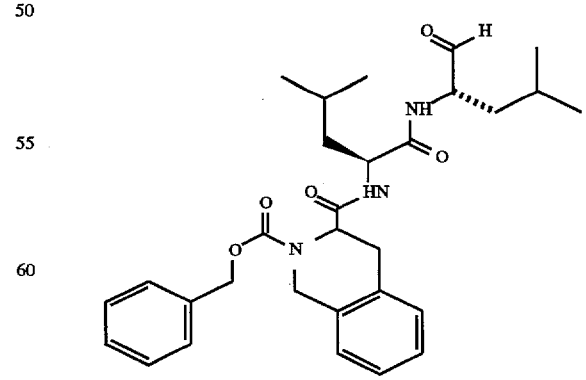

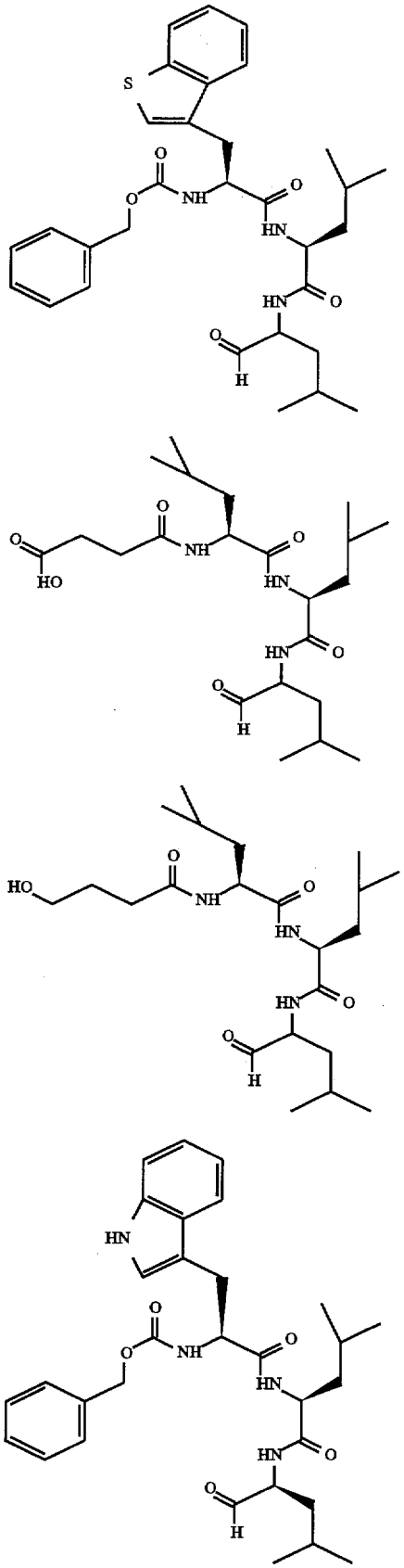
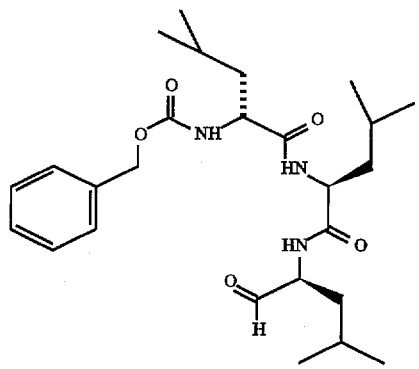
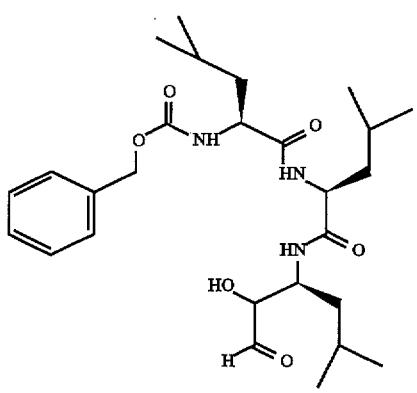
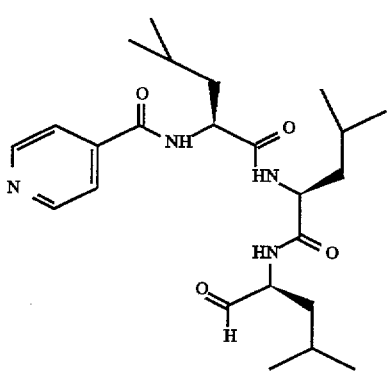
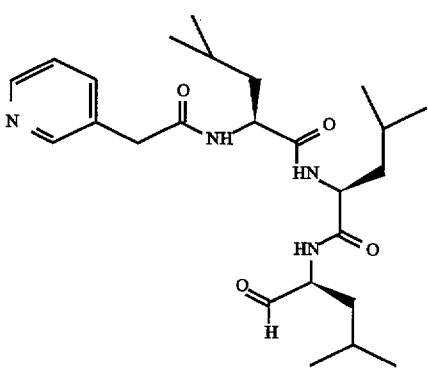

93
-continued
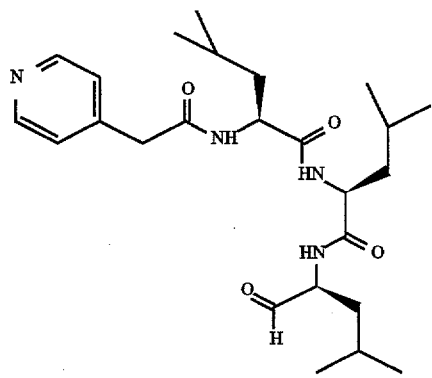
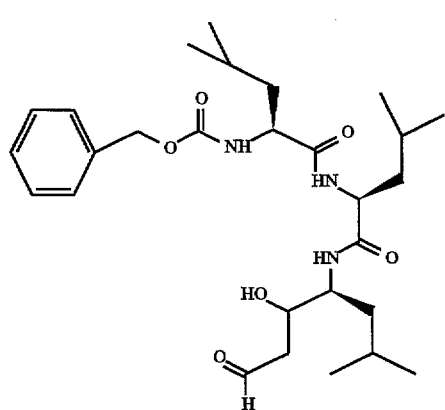
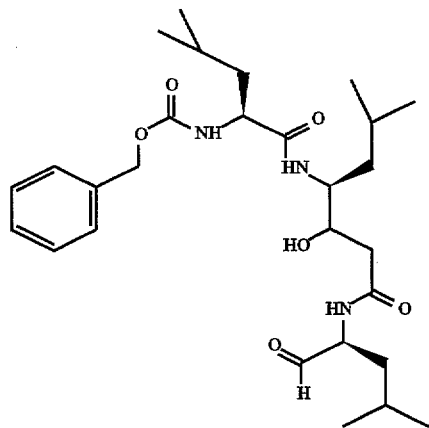
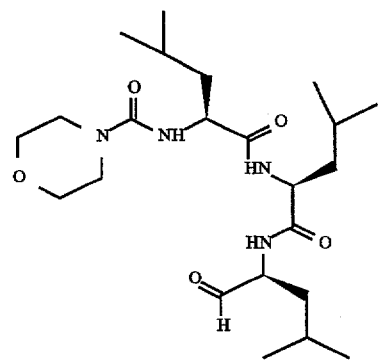
94
-continued
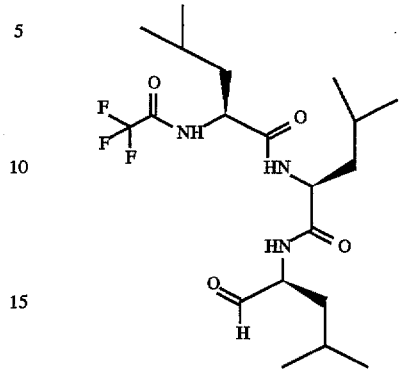
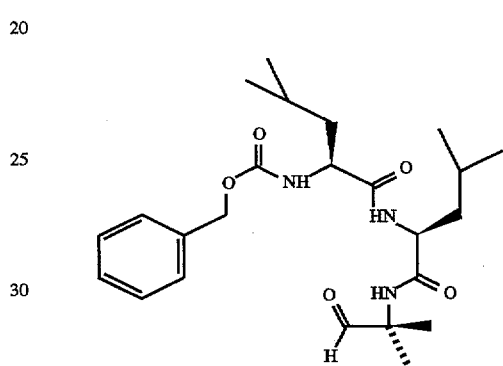
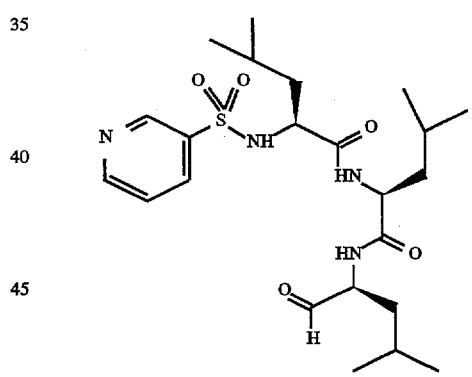
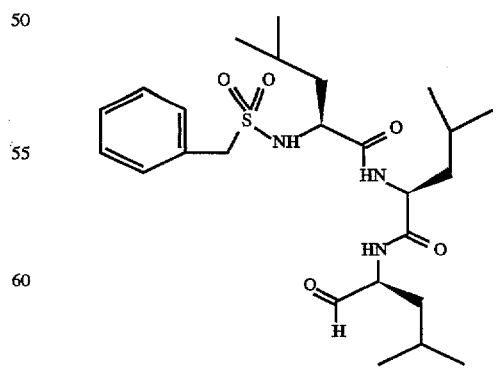

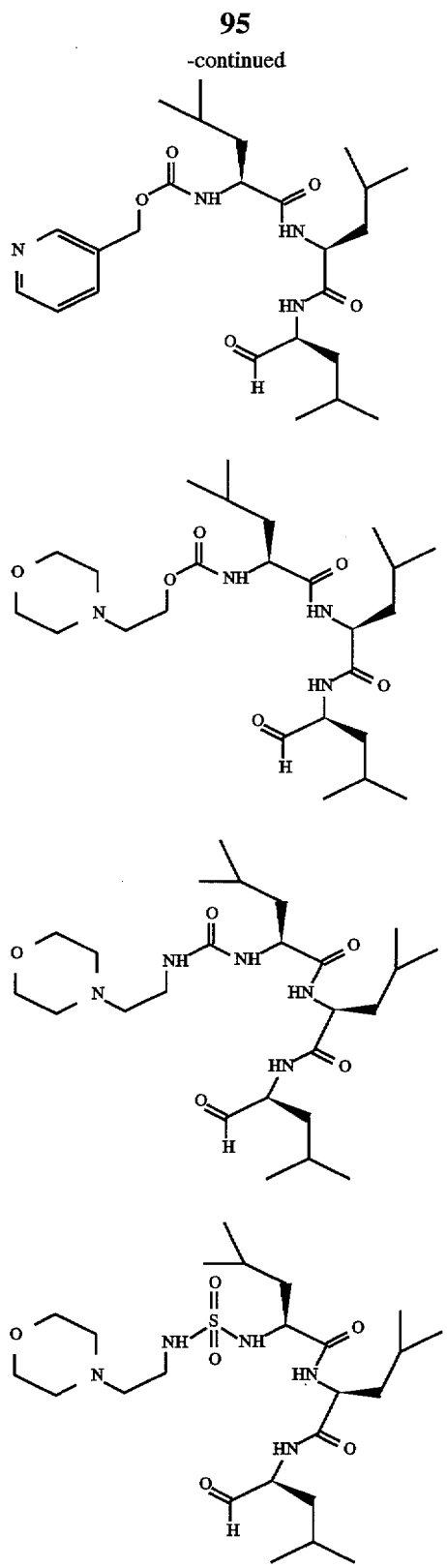
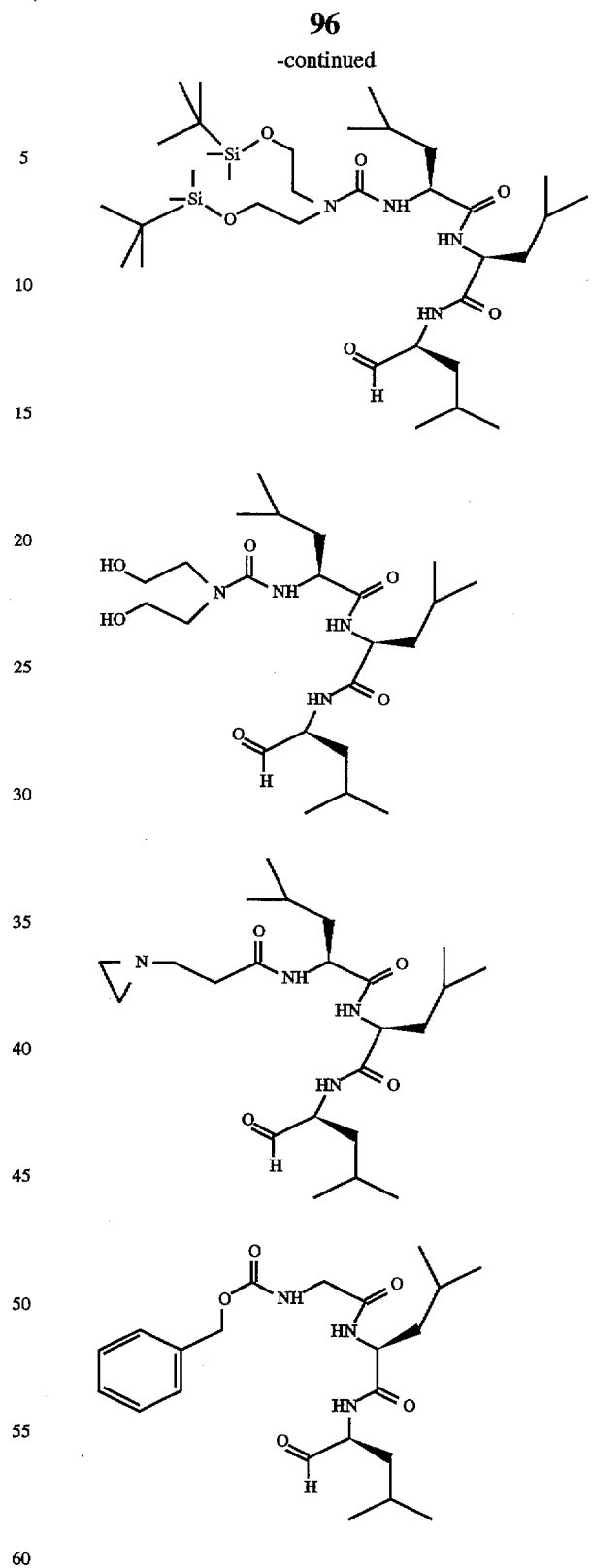

-continued
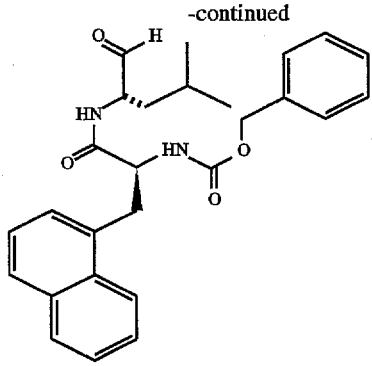
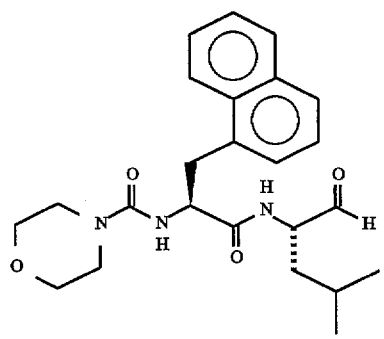
and
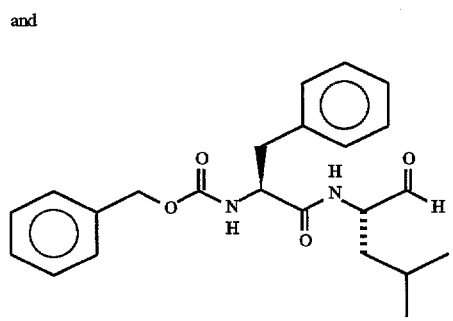
10. A compound selected from the group consisting of
Z—Leu—Leu—Abu—H
Z—Leu—Leu-2-Nal—H
Z—Leu—Leu—Tyr—H
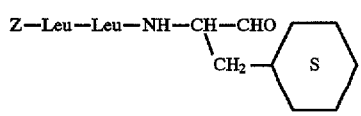
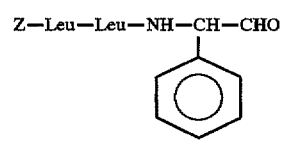
Z—Leu—Leu—Trp—H
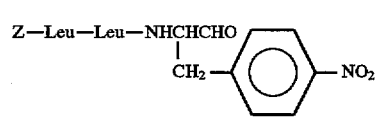
-continued
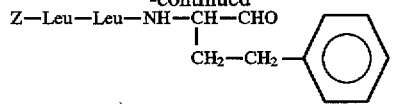
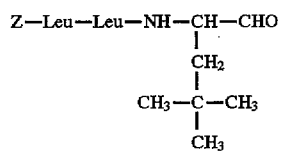
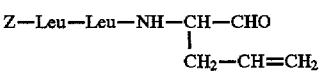
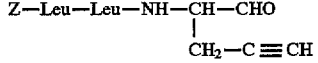
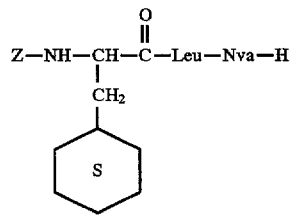
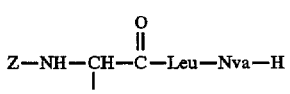
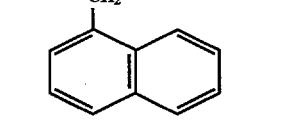
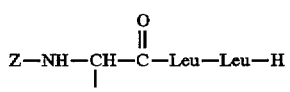
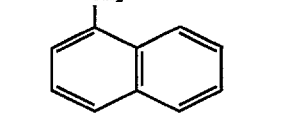
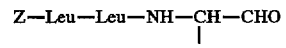
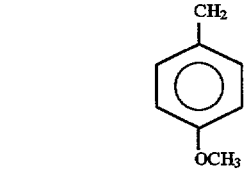
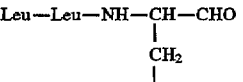
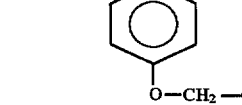
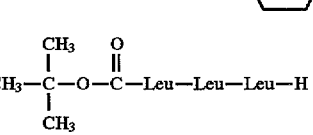

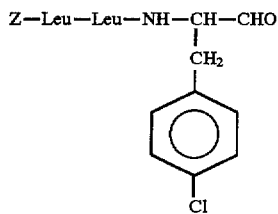
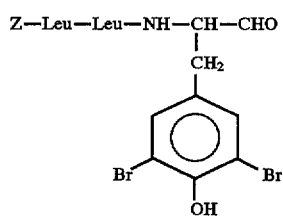
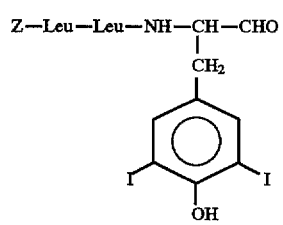
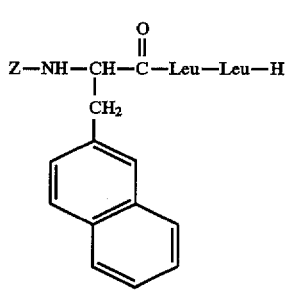
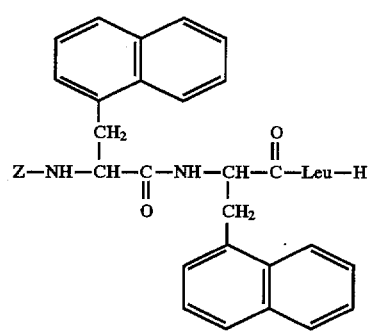
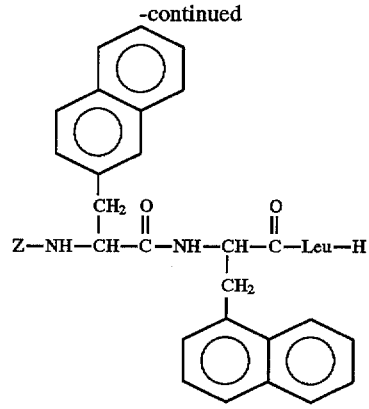
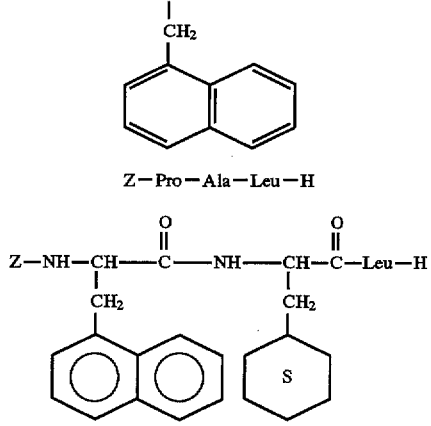
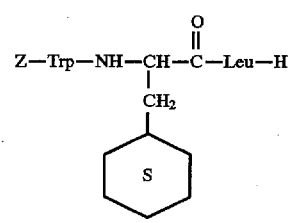
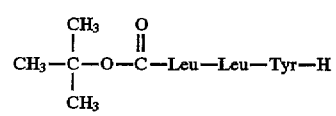
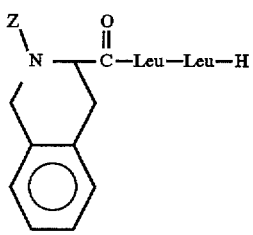
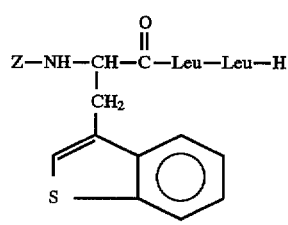

101
-continued

HOOCCH₂CH₂C(=O)—Leu—Leu—Leu—H

HOCH₂CH₂CH₂C(=O)—Leu—Leu—Leu—H

Z—Trp—Leu—Leu—H

Z—Leu—Leu—NH—CH(CH₂CH(CH₃)₂)—CH(OH)—CHO

Z—Leu—Leu—NH—CH(CH₂CH(CH₃)₂)—CH(OH)—CH₂—CHO (3-pyridyl)-C(=O)—Leu—Leu—Leu—H (4-pyridyl)-CH₂—C(=O)—Leu—Leu—Leu—H (3-pyridyl)-CH₂—C(=O)—Leu—Leu—Leu—H morpholino-C(=O)—Leu—Leu—Leu—H CF₃—C(=O)—Leu—Leu—Leu—H Z—Leu—Leu—NH—CH(CH₃)—CHO with extra CH₃

(3-pyridyl)-SO₂—Leu—Leu—Leu—H

Ph—CH₂—SO₂—Leu—Leu—Leu—H (3-pyridyl)-CH₂—O—C(=O)—Leu—Leu—Leu—H

102
-continued

Z—Leu—NH—CH(CH₂CH(CH₃)₂)—CH(OH)—CH₂—C(=O)—Leu morpholino-N—CH₂—CH₂—O—C(=O)—Leu—Leu—Leu—H morpholino-N—CH₂—CH₂—NH—C(=O)—Leu—Leu—Leu—H morpholino-N—CH₂—CH₂—NH—S(=O)₂—Leu—Leu—Leu—H (CH₃)₃C—Si(CH₃)₂—O—CH₂CH₂—N(CH₂CH₂—O—Si(CH₃)₂—C(CH₃)₃)—C(=O)—Leu—Leu—Leu—H HO—CH₂CH₂—N(CH₂CH₂—OH)—C(=O)—Leu—Leu—Leu—H aziridinyl-N—CH₂CH₂C(=O)—Leu—Leu—Leu—H Z—Phe—Leu—H Z—Gly—Leu—Leu—H Z—NH—CH(CH₂-(1-naphthyl))—C(=O)—Leu—H morpholino-N—C(=O)—NH—CH(CH₂-(1-naphthyl))—C(=O)—Leu—H and 103
-continued
Z—Leu—Leu—NH—CH—CHO
                   |
                   CH₂
                   |
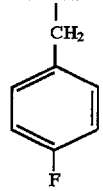
where:
Z = 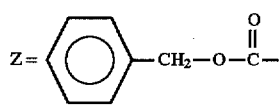
11. A compound selected from the group consisting of
104
-continued
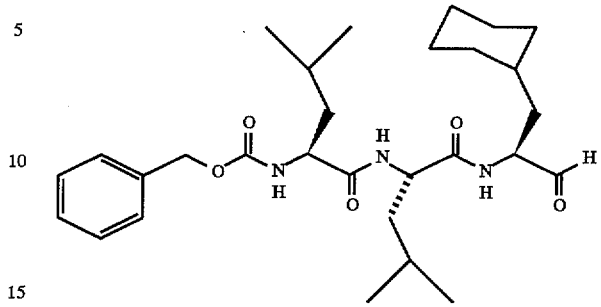
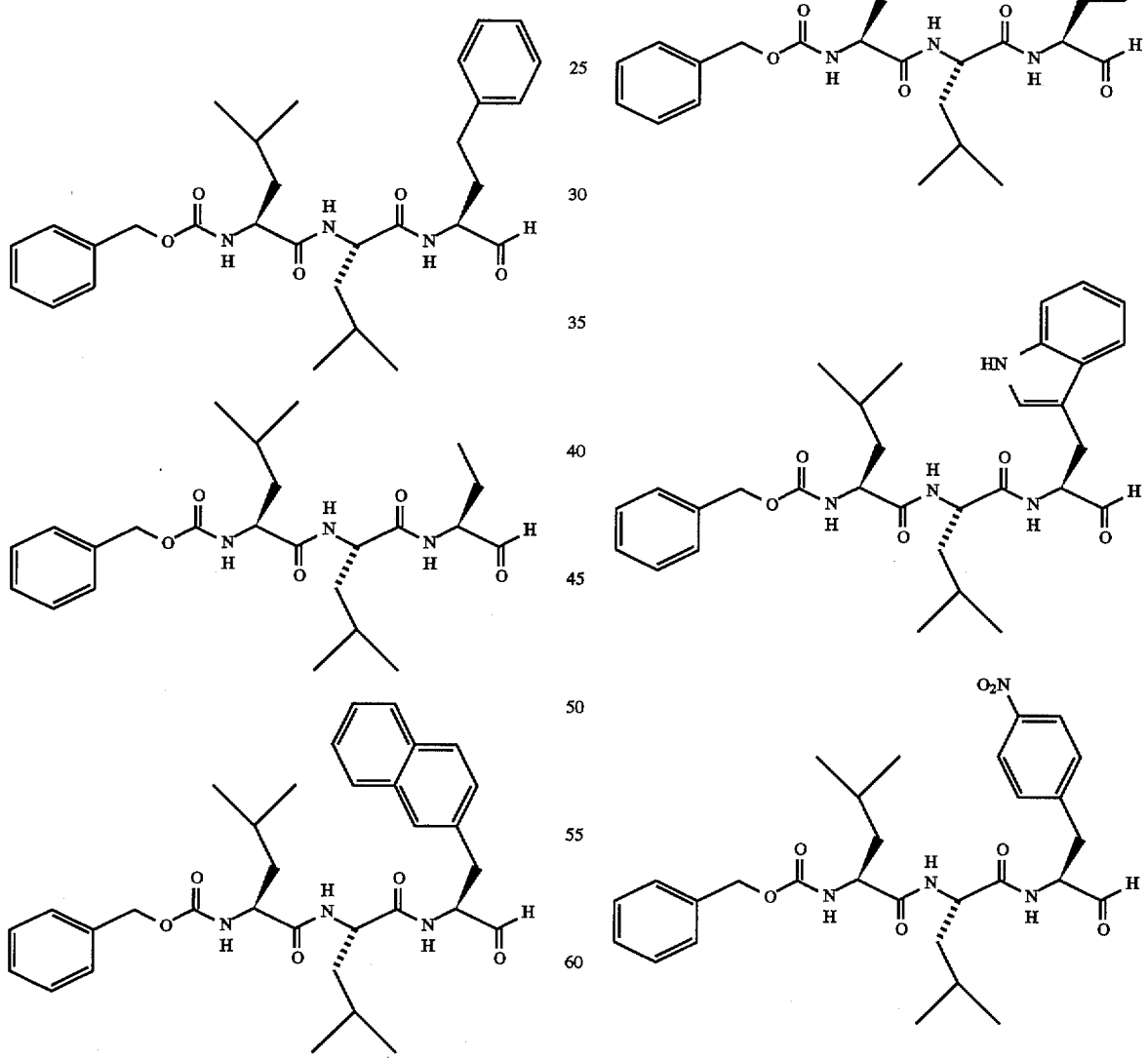

105
-continued
106
-continued
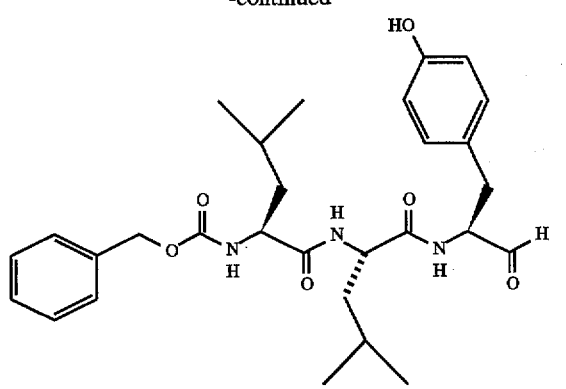
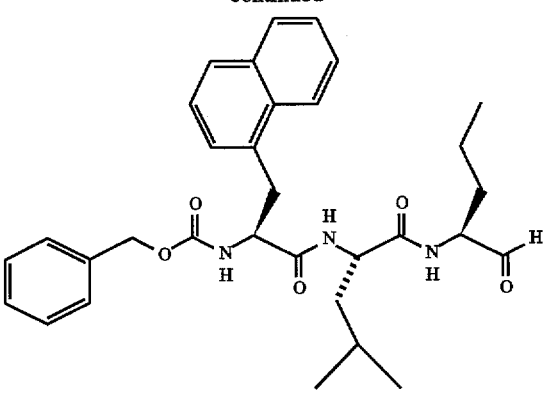

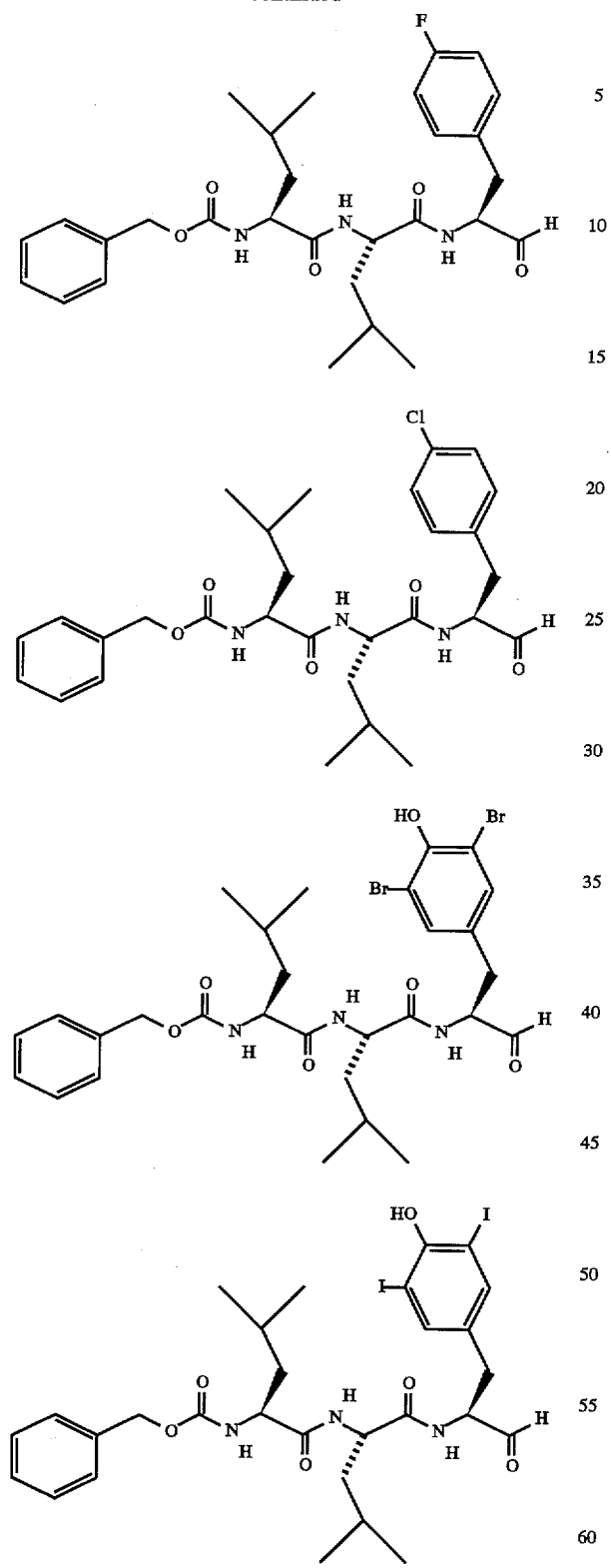
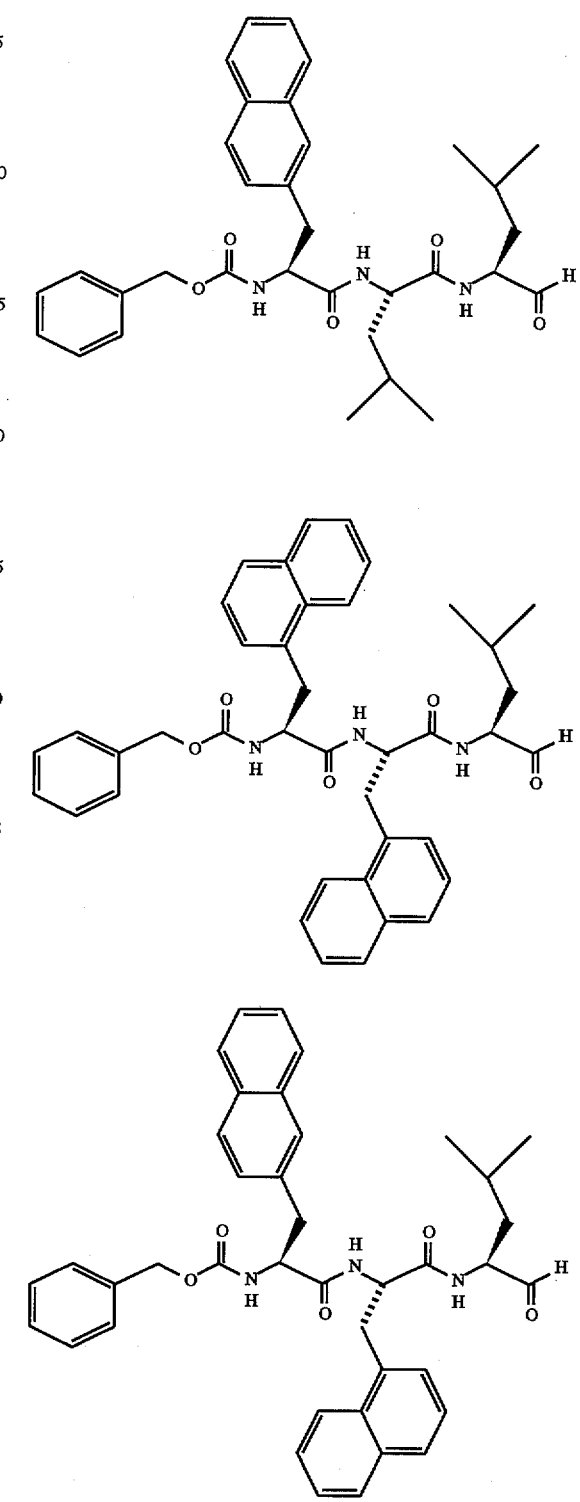

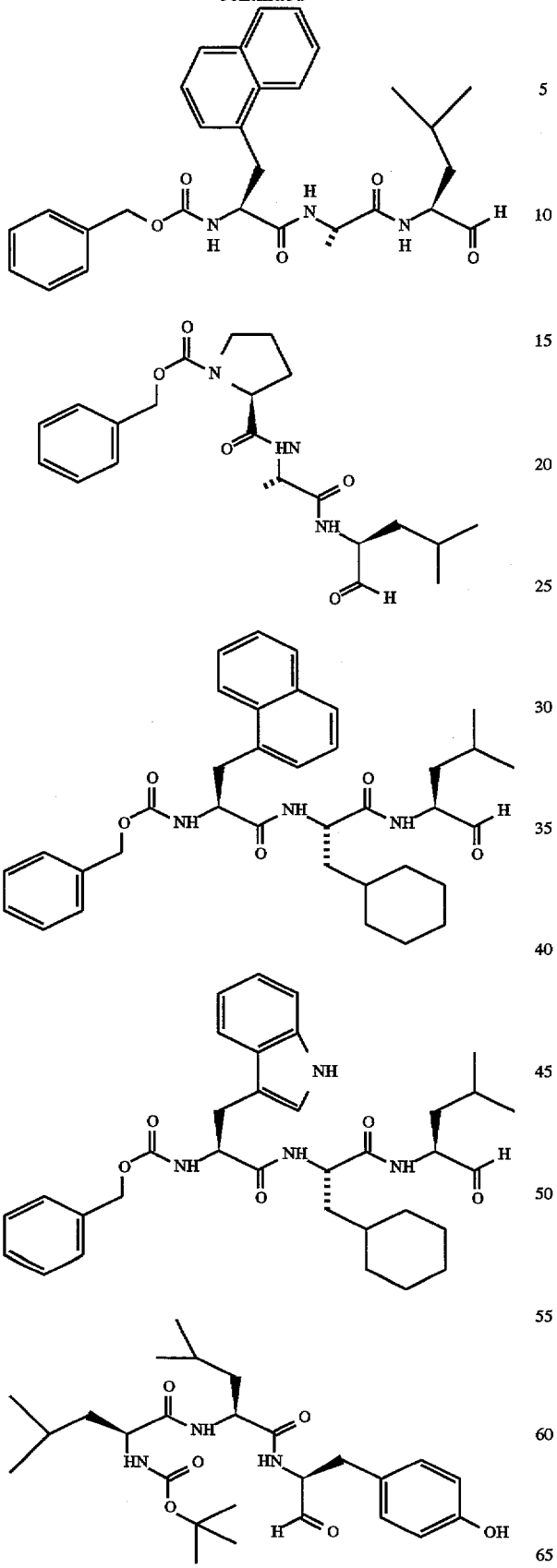
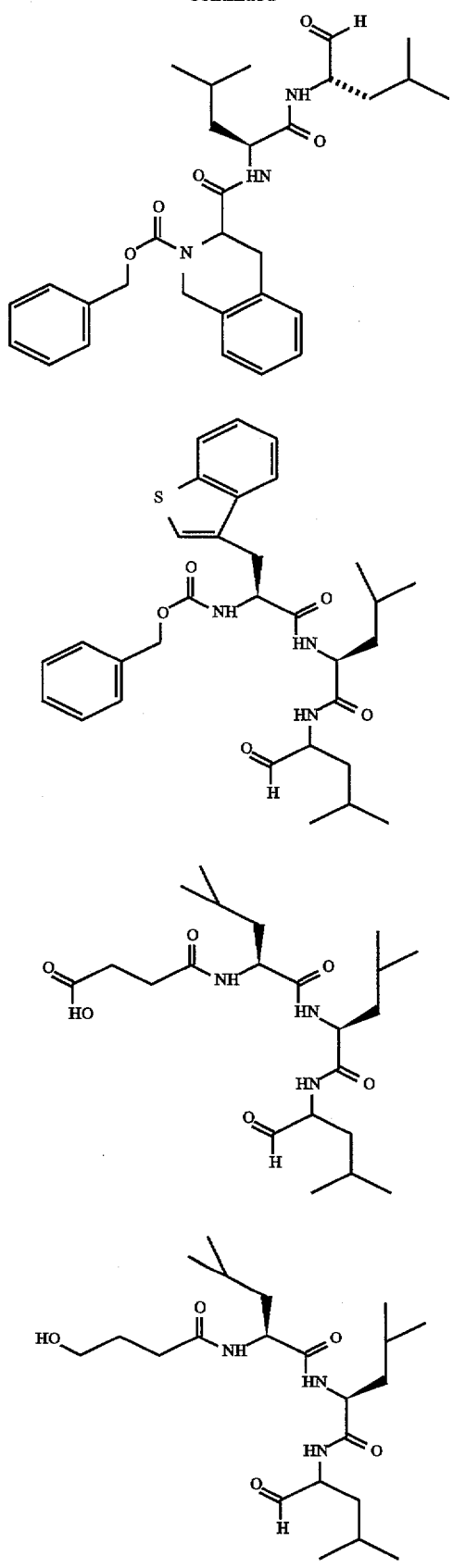

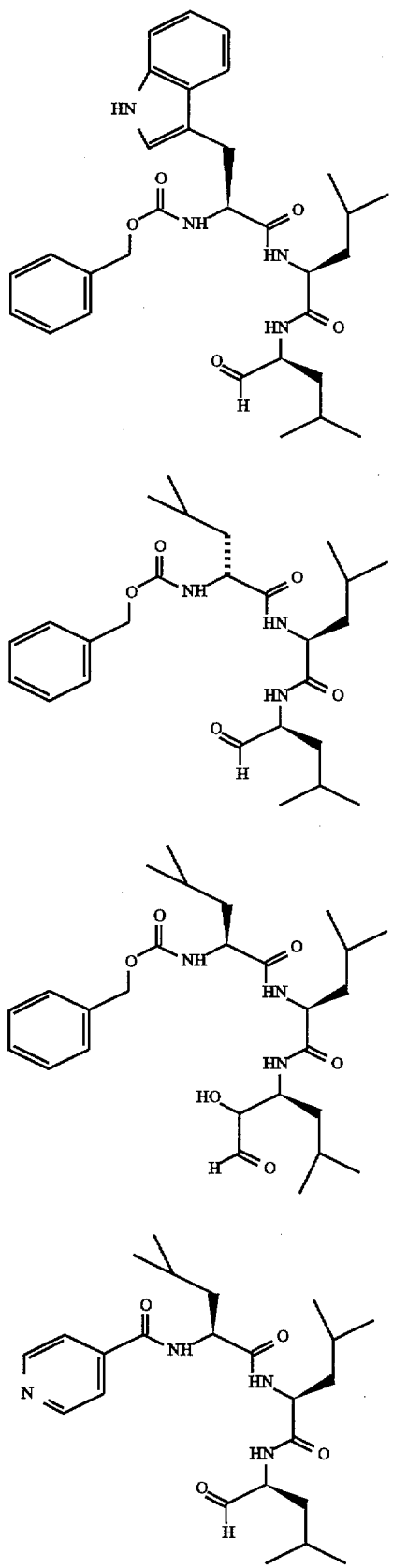
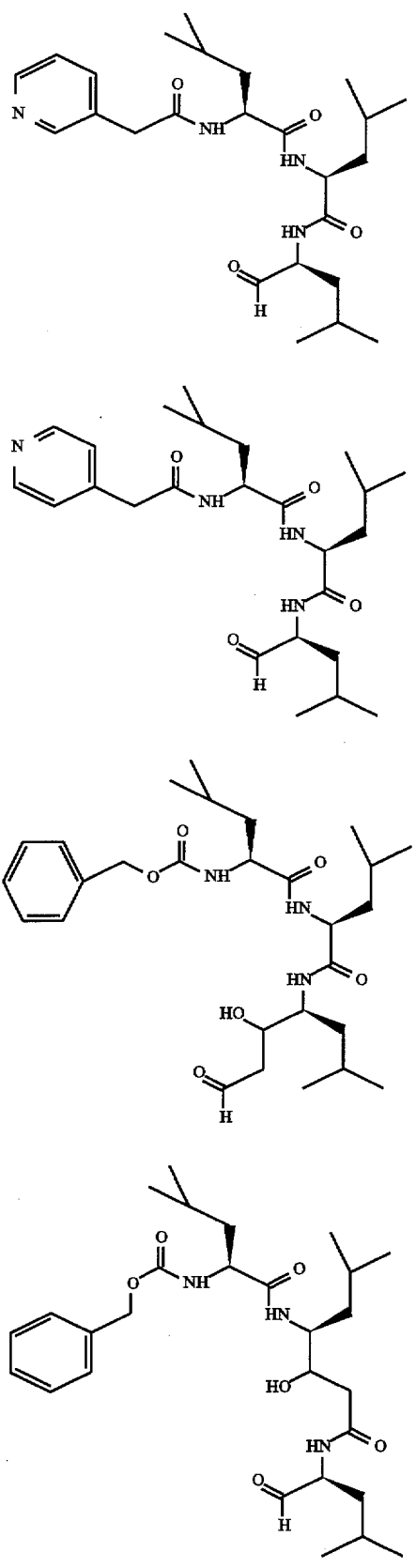

113
-continued
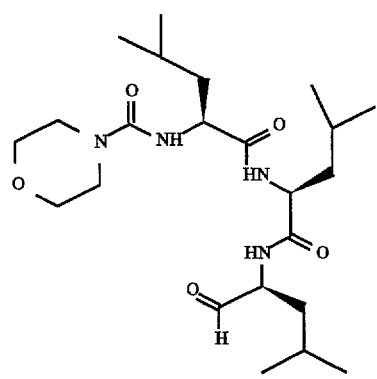
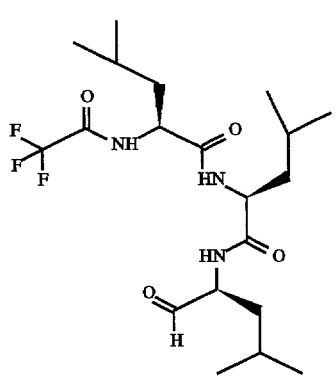
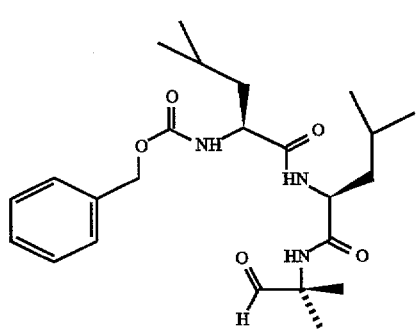
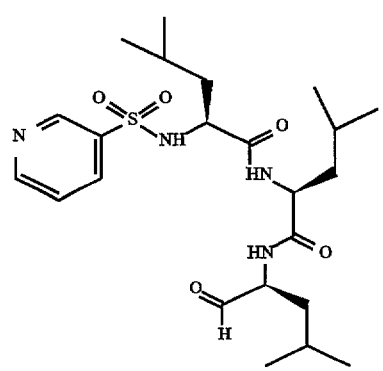
114
-continued
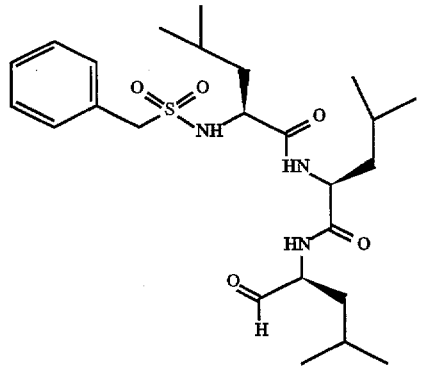
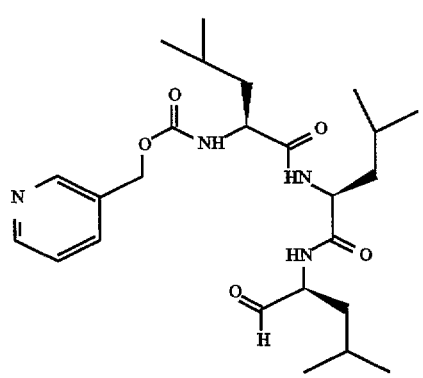
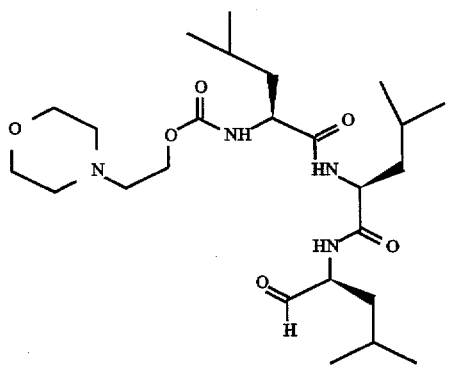
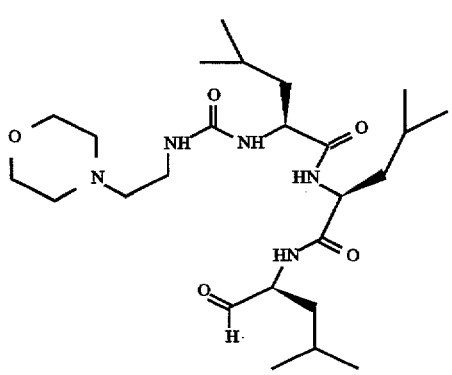

115
-continued
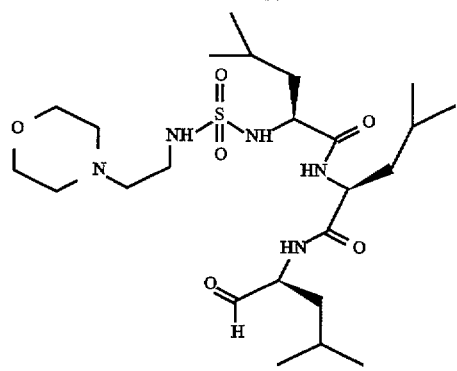
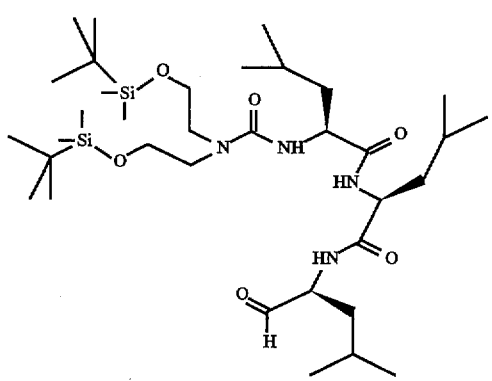
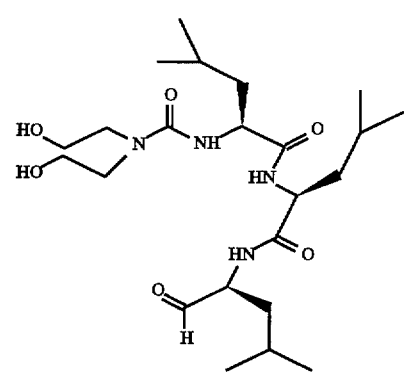
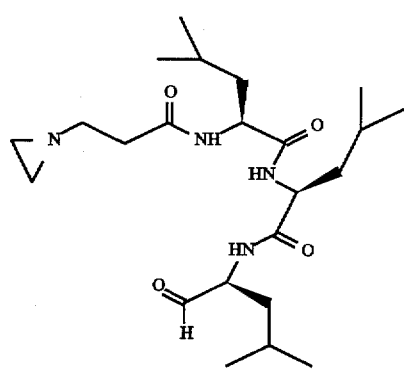
116
-continued
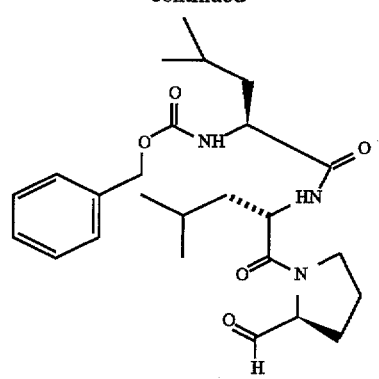
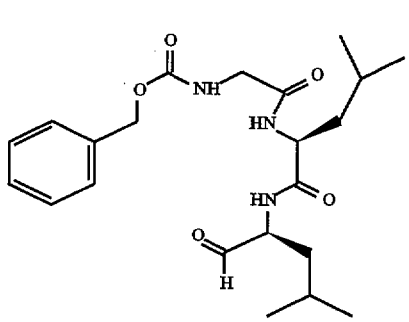
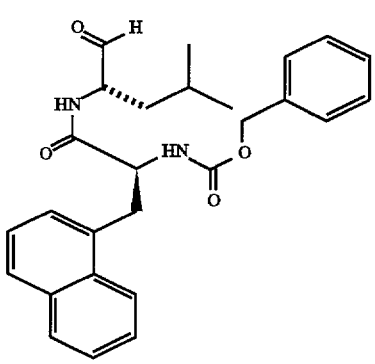
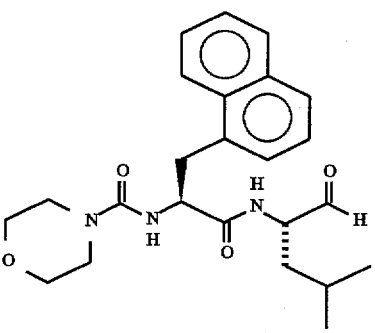
and

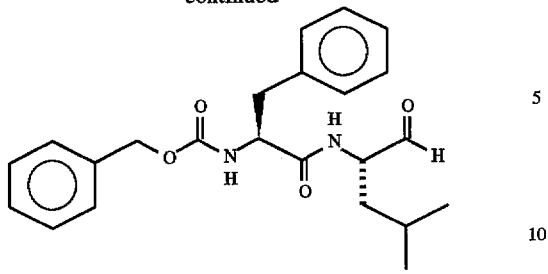
12. A method for reducing the rate of intracellular protein breakdown in an animal comprising contacting cells of the animal with a proteasome inhibitor selected from the group consisting of:
Z—Leu—Leu-2-Nal—H
Z—Leu—Leu—Abu—H
Z—Leu—Leu—Tyr—H
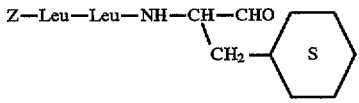
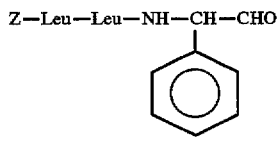
Z—Leu—Leu—Trp—H
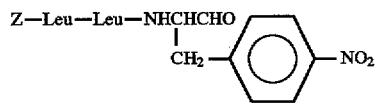
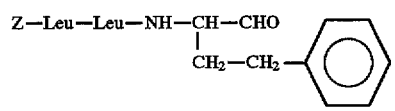
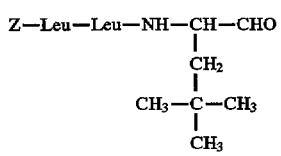
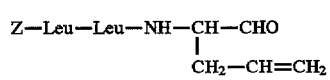
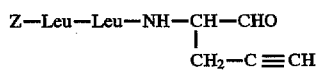
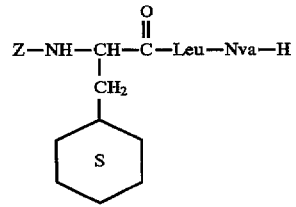
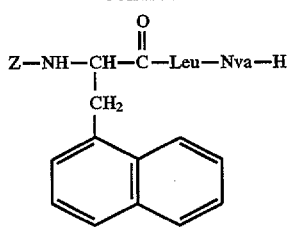
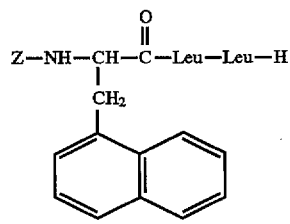
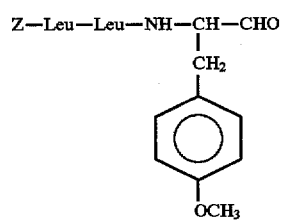
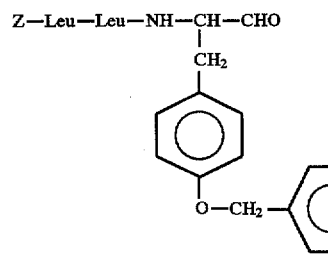
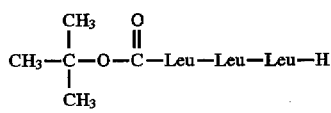
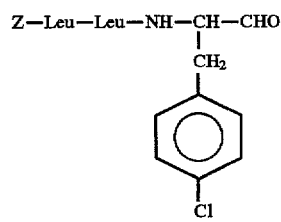
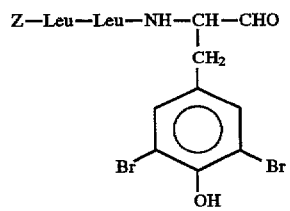

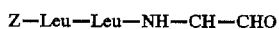
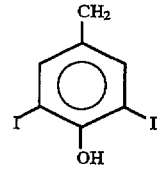
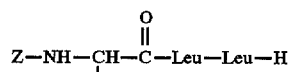
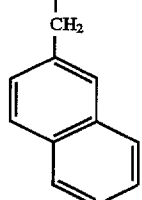
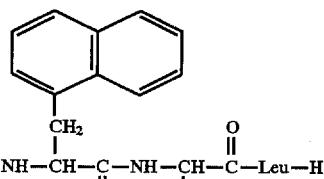
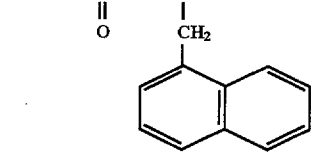
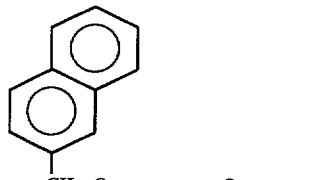
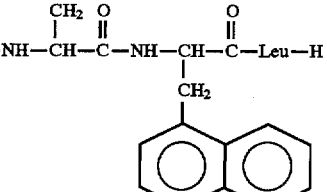
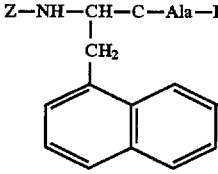
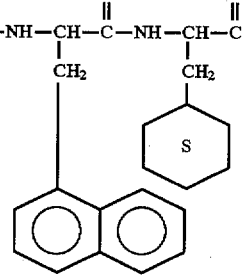
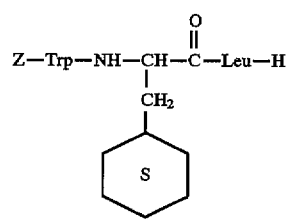
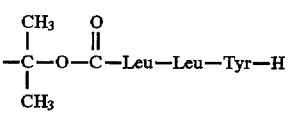
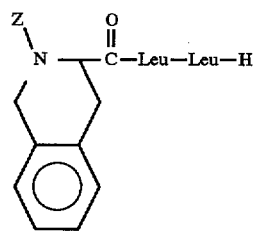
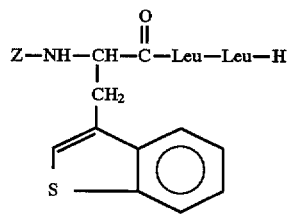
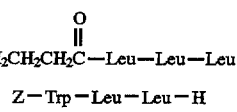
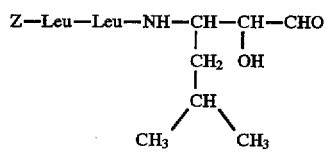
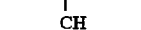
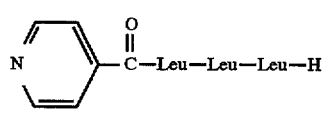
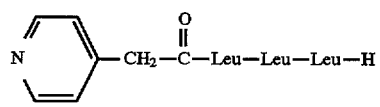

121
-continued 3-pyridyl-CH$_2$-CO-Leu-Leu-Leu-H morpholino-N-CO-Leu-Leu-Leu-H CF$_3$-CO-Leu-Leu-Leu-H Z-Leu-Leu-NH-C(CH$_3$)$_2$-CHO 3-pyridyl-SO$_2$-Leu-Leu-Leu-H Ph-CH$_2$-SO$_2$-Leu-Leu-Leu-H 3-pyridyl-CH$_2$-O-CO-Leu-Leu-Leu-H Z-Leu-NH-CH(CH$_2$CH(CH$_3$)$_2$)-CH(OH)-CH$_2$-CO-Leu-H Z-Leu-Leu-NH-CH(CH$_2$CH(CH$_3$)$_2$)-CH(OH)-CH$_2$-CHO morpholino-N-CH$_2$-CH$_2$-O-CO-Leu-Leu-Leu-H morpholino-N-CH$_2$-CH$_2$-NH-CO-Leu-Leu-Leu-H morpholino-N-CH$_2$-CH$_2$-NH-SO$_2$-Leu-Leu-Leu-H

122
-continued (CH$_3$)$_3$C-Si(CH$_3$)$_2$-O-CH$_2$CH$_2$-N(CH$_2$CH$_2$-O-Si(CH$_3$)$_2$-C(CH$_3$)$_3$)-CO-Leu-Leu-Leu-H HO-CH$_2$CH$_2$-N(CH$_2$CH$_2$-OH)-CO-Leu-Leu-Leu-H aziridinyl-N-CH$_2$CH$_2$-CO-Leu-Leu-Leu-H Z—Phe—Leu—H Z—Gly—Leu—Leu—H Z-NH-CH(CH$_2$-1-naphthyl)-CO-Leu-H morpholino-N-CO-NH-CH(CH$_2$-1-naphthyl)-CO-Leu-H Z-Leu-Leu-NH-CH(CH$_2$-(4-F-phenyl))-CHO and where: Z = Ph-CH$_2$-O-CO- Nal = Naphthylalanine

13. A method for reducing the rate of intracellular protein breakdown in an animal comprising contacting cells of the animal with a proteasome inhibitor selected from the group consisting of

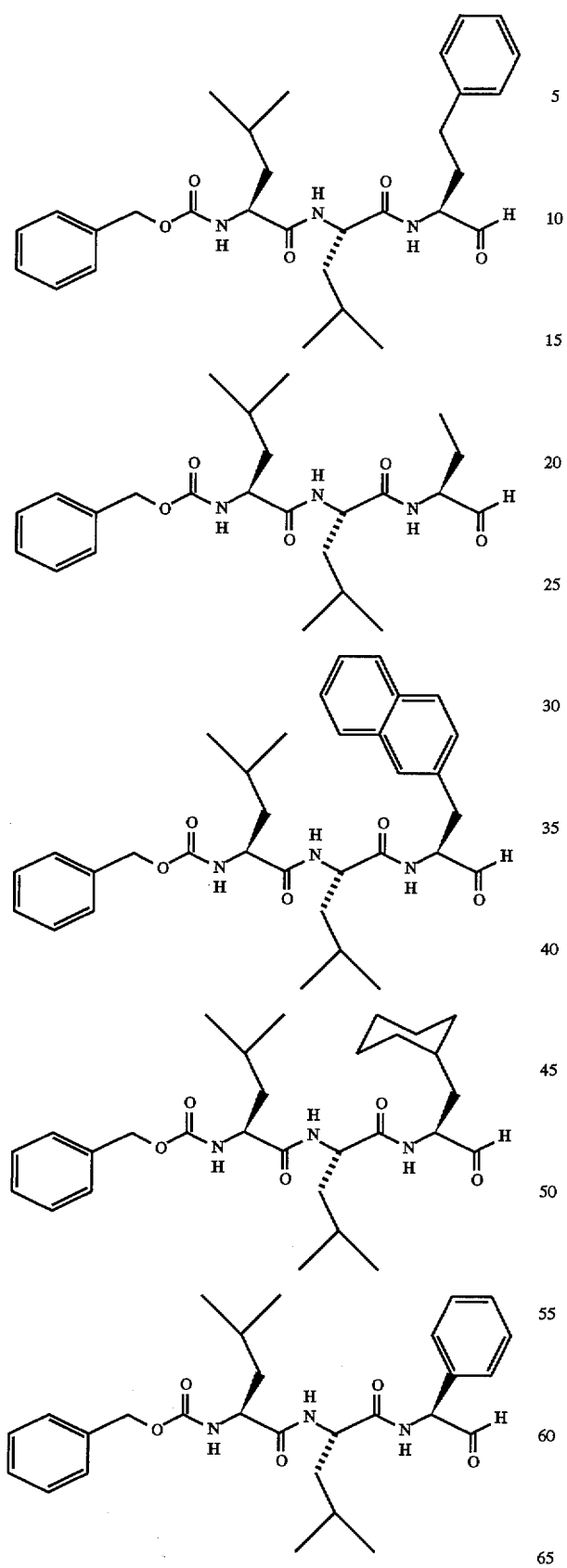
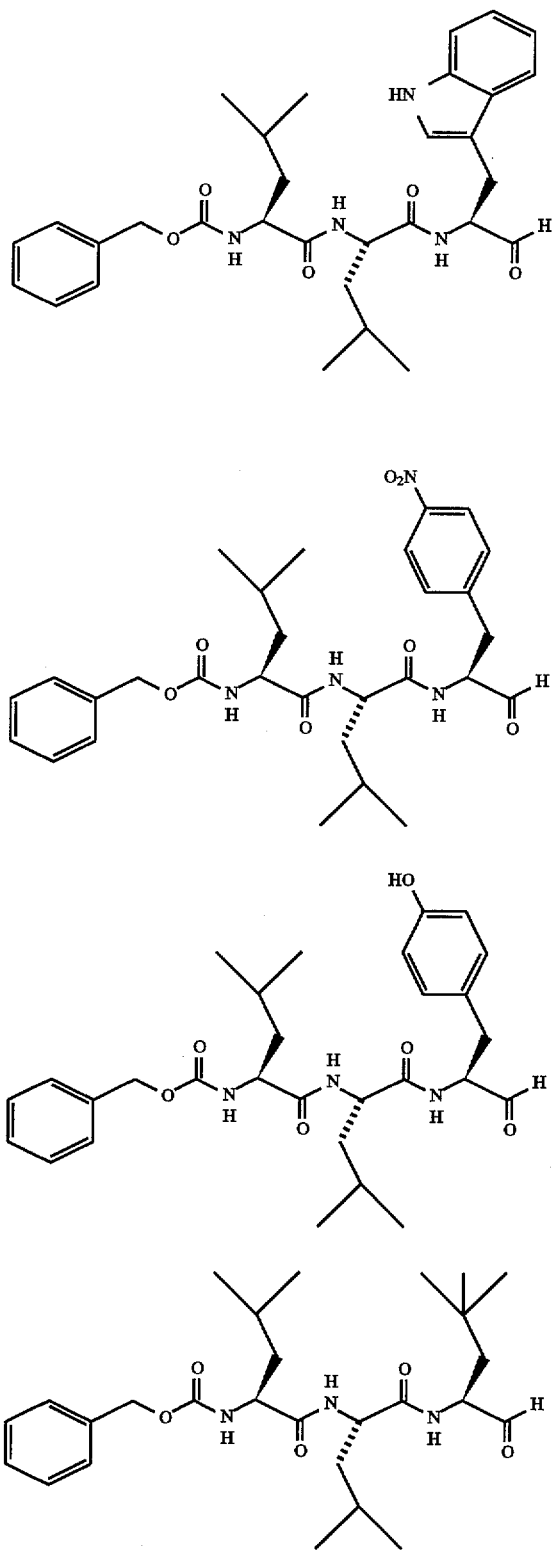

125
-continued
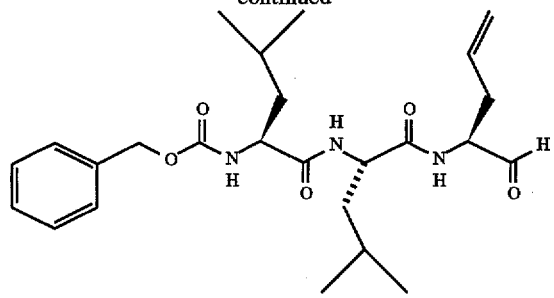
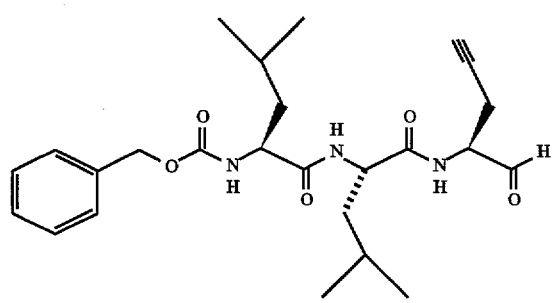
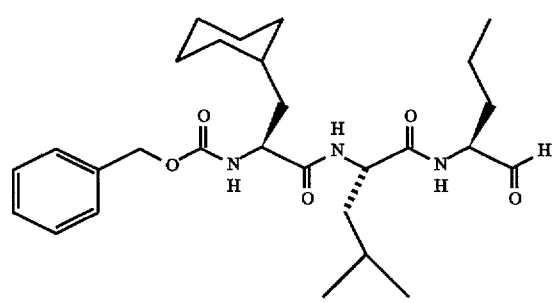
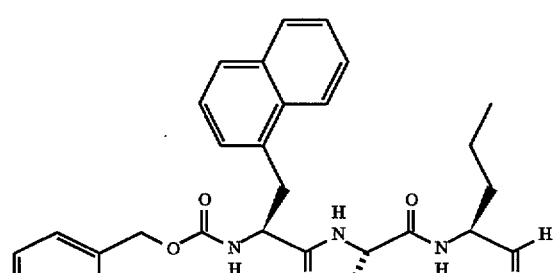
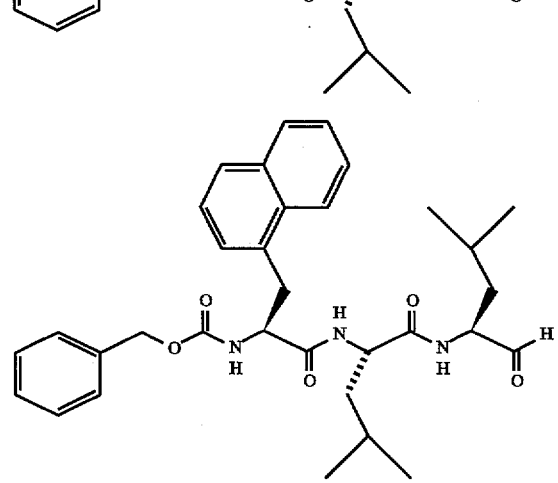
126
-continued
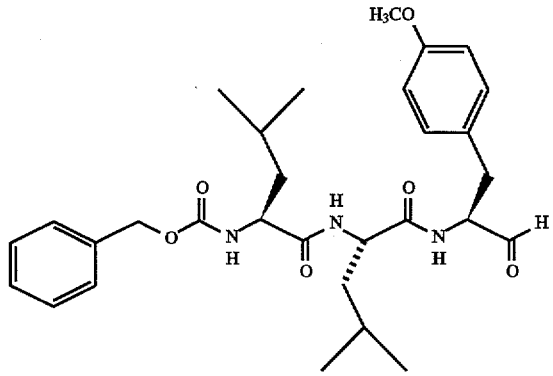
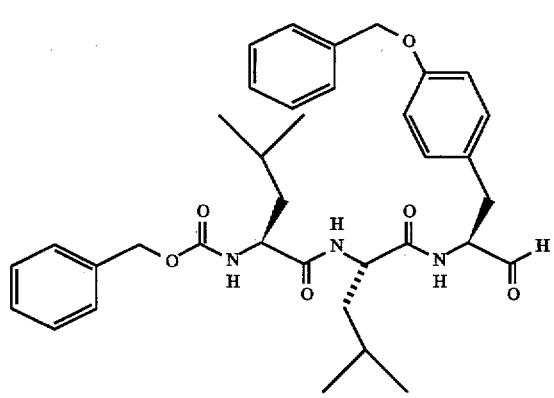
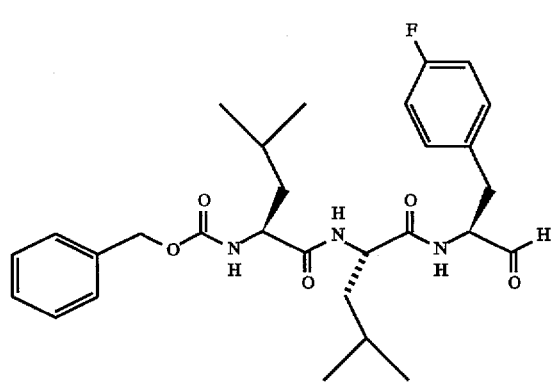
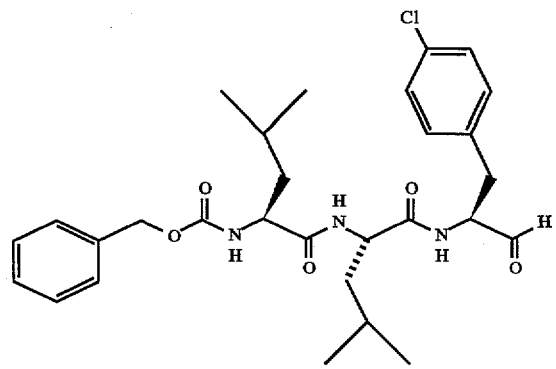

127
-continued
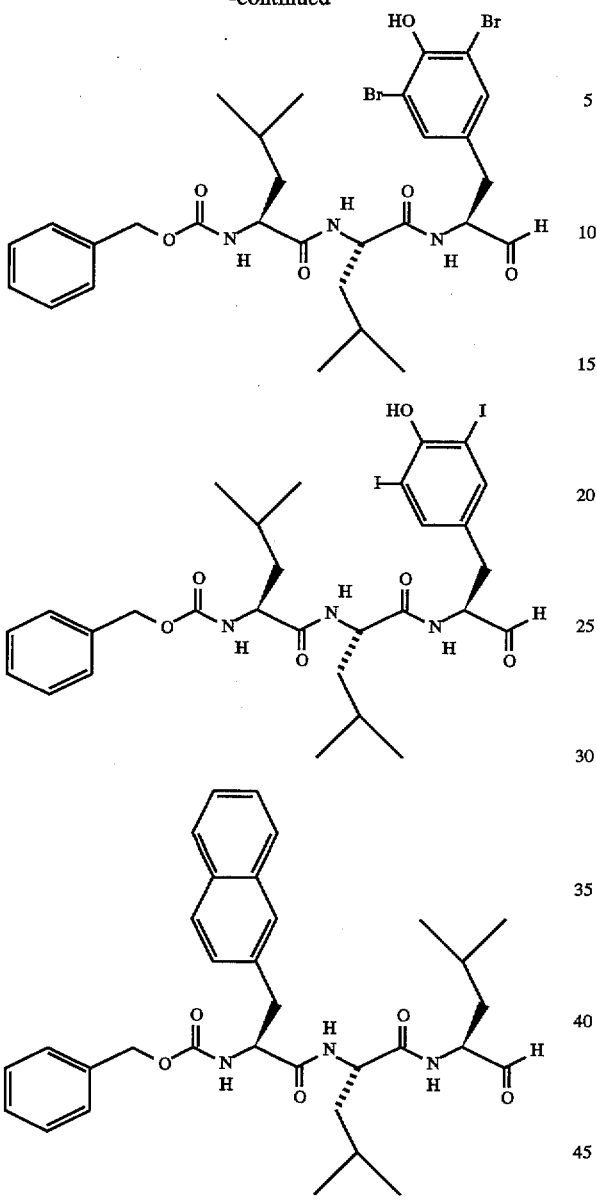
128
-continued
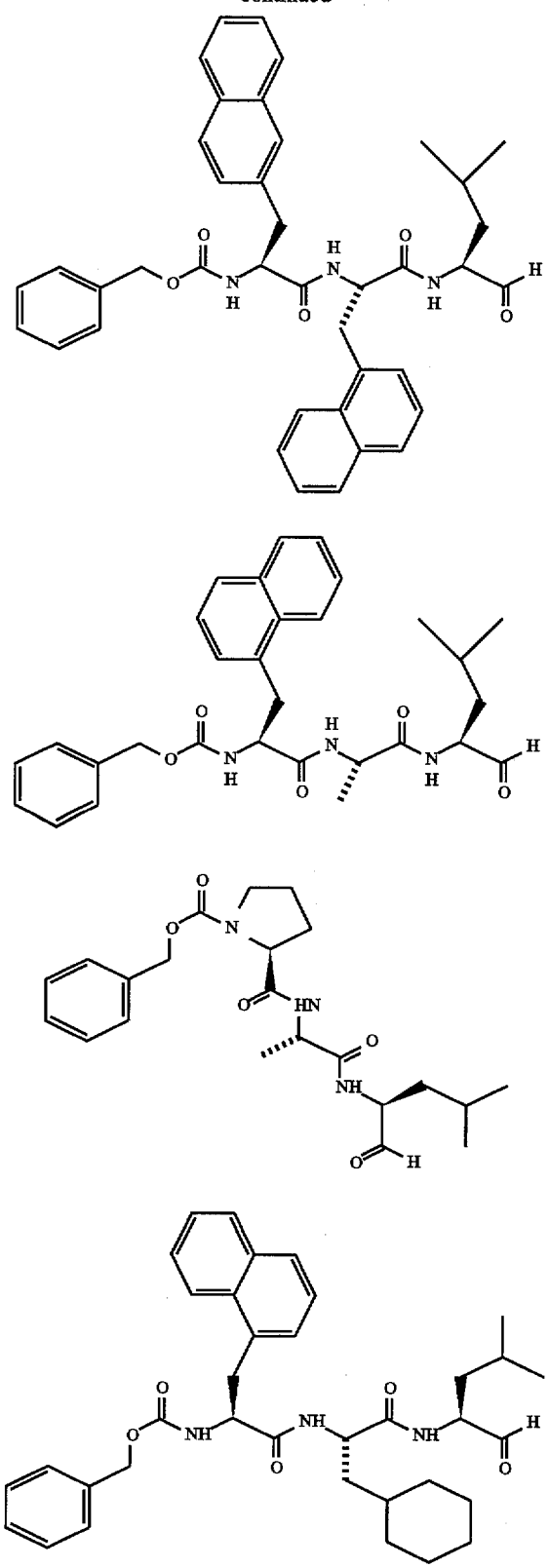

129
-continued
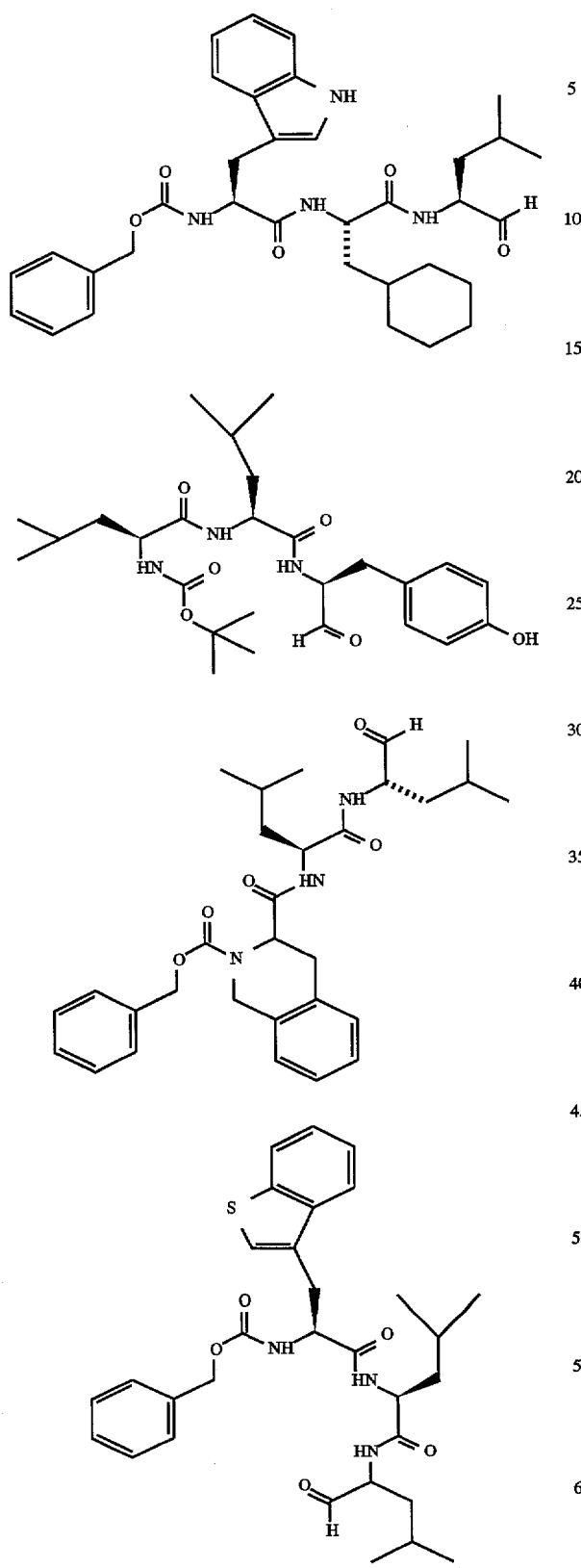
130
-continued
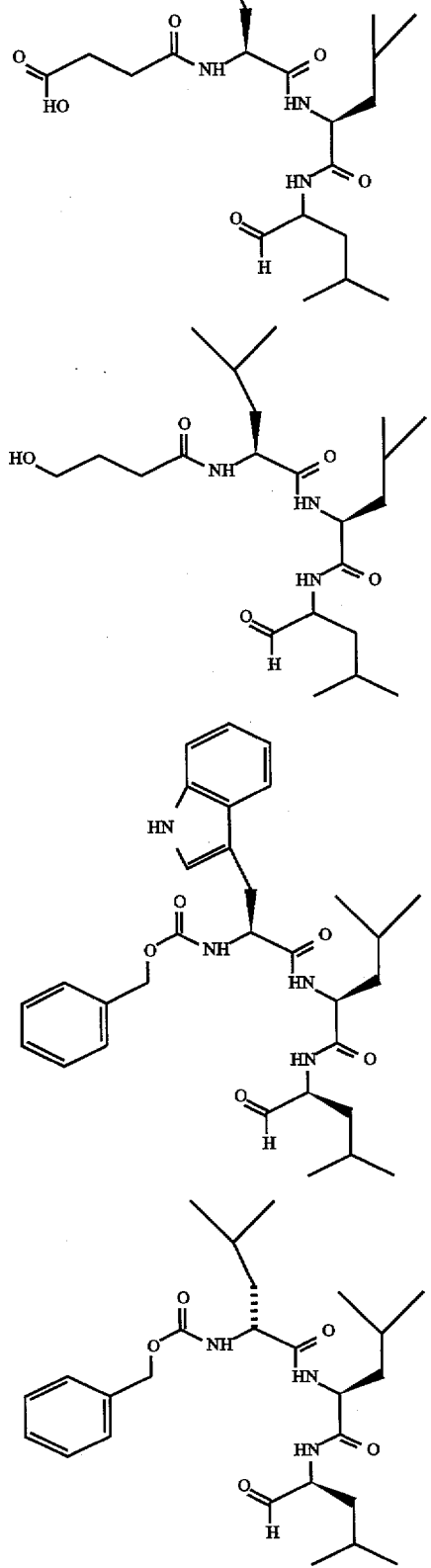

131
-continued
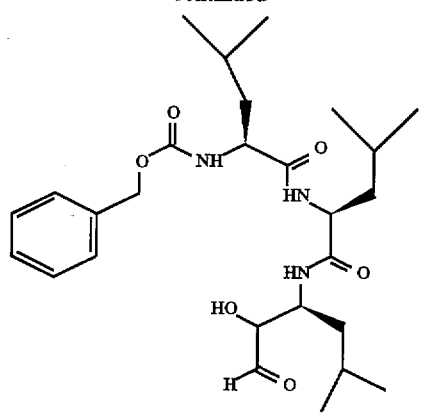
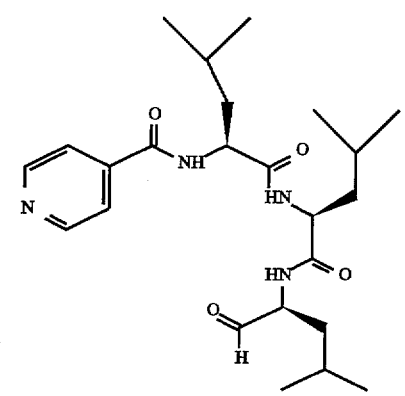
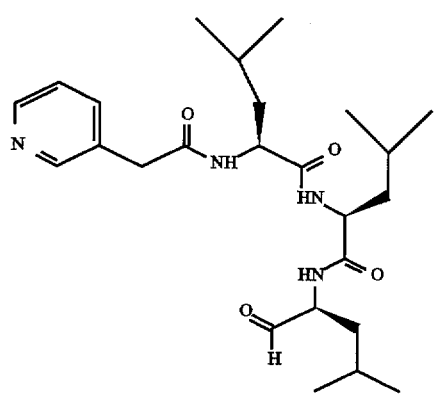
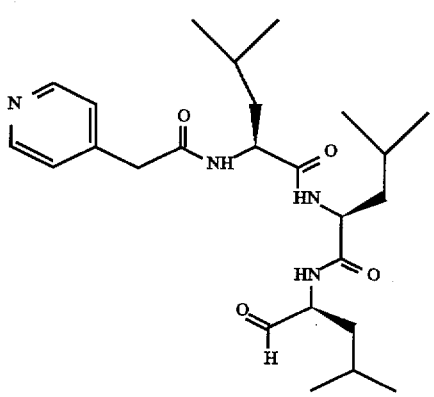
132
-continued
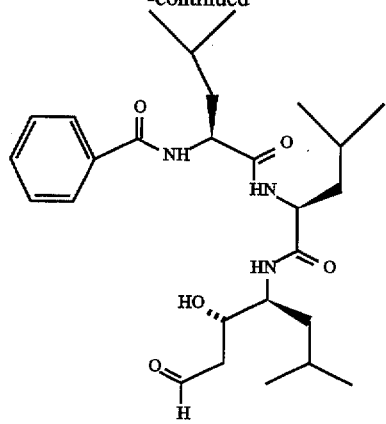
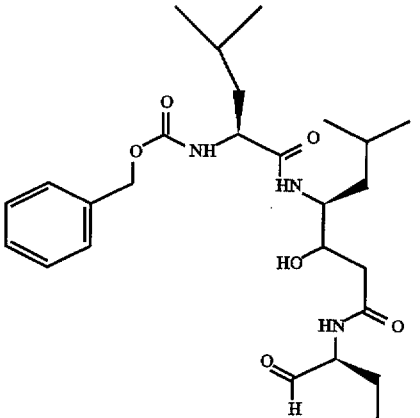
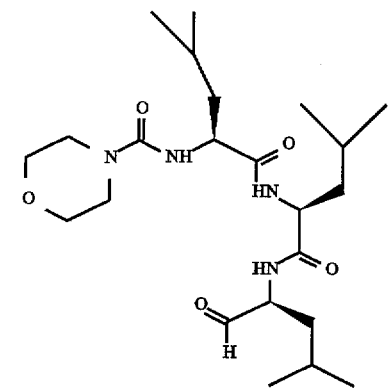
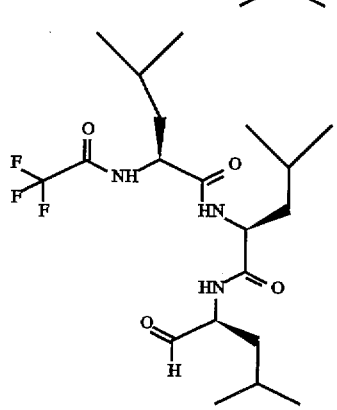

133
-continued
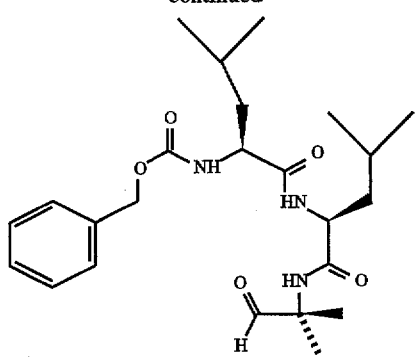
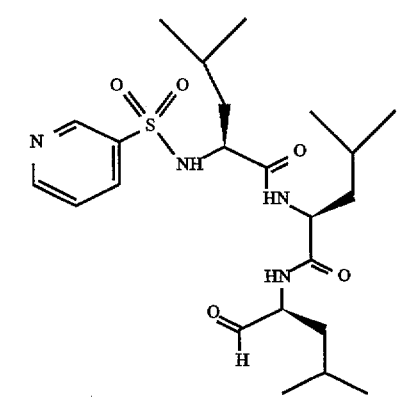
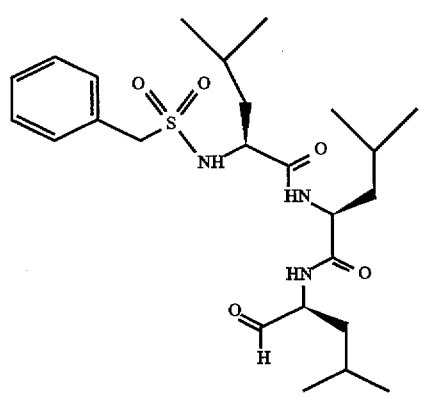
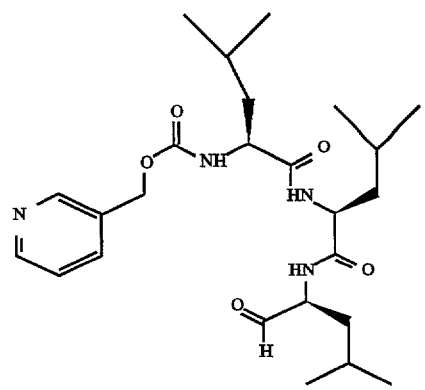
134
-continued
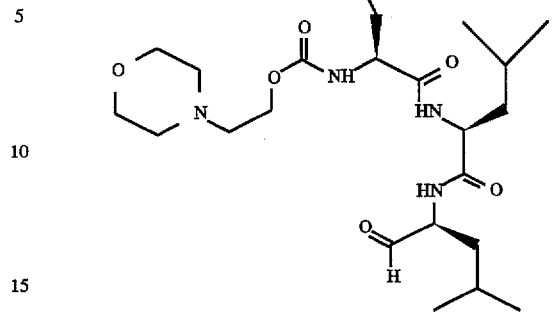
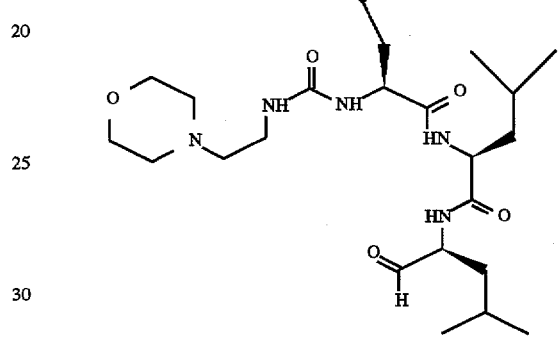
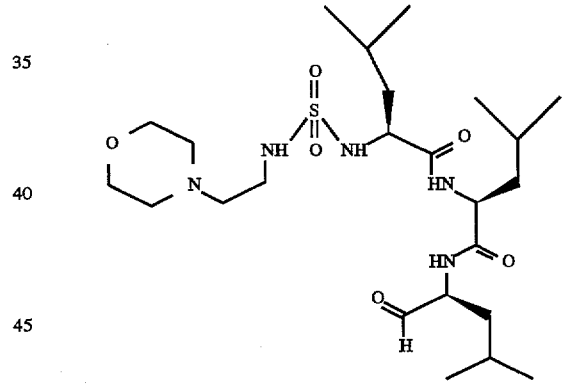
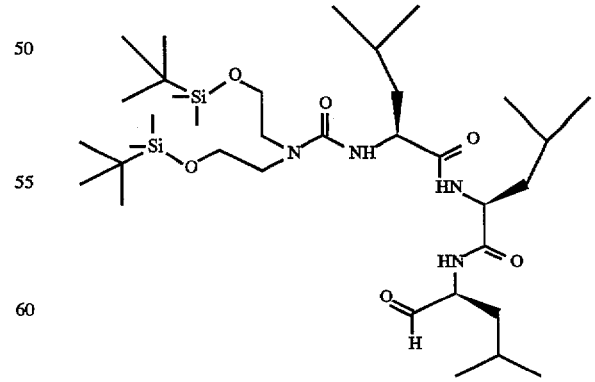

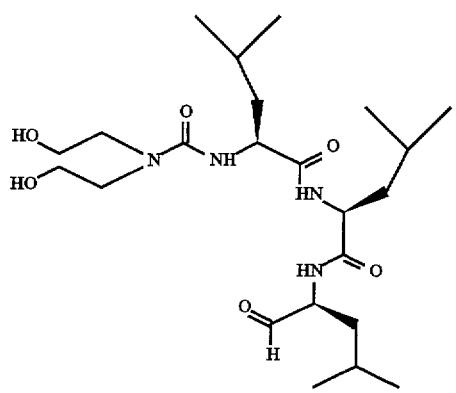

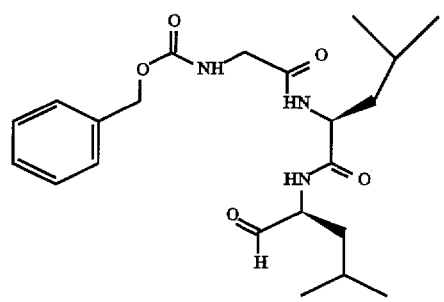

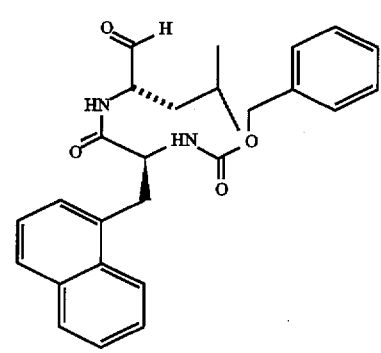

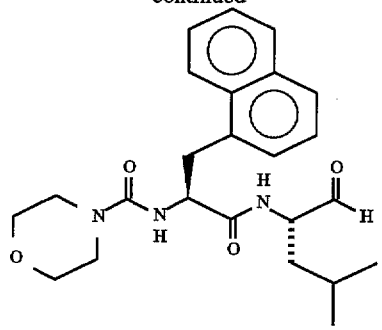

and

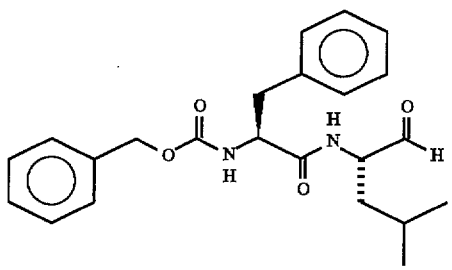

14. A method for reducing the rate of degradation of p53 protein in an animal comprising administering to said animal a proteasome inhibitor of the structure:

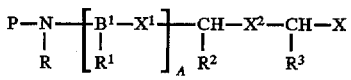

where

P is an amino-group-protecting moiety;

$B^1$ at each occurrence is independently selected from the group consisting of $$-\underset{|}{N}- \quad \text{and} \quad -\underset{|}{CH}-;$$

X is selected from the group consisting of

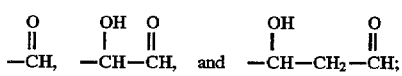

$X^1$ at each occurrence and $X^2$ are independently selected from the group consisting of

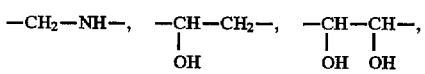

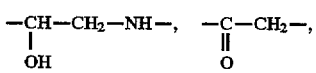

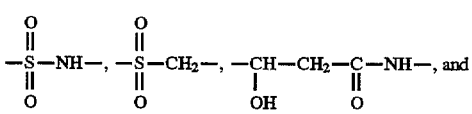

$-CH=CH-$ except that if B¹ is

then X¹ must be

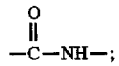

R is hydrogen or together with the adjacent R¹, or R² if A=0, forms a nitrogen-containing heterocyclic ring;

R¹ at each occurrence, R², and R³ are independently selected from the group consisting of hydrogen, alkyl, cycloalkyl, alkenyl, alkynyl, aryl, and —CH₂—R⁴, where R⁴ is aryl, aralkyl, alkaryl, cycloalkyl or —Y—R⁵, where Y is a chalcogen, and R⁵ is alkyl; and A is 0, 1, or 2; and wherein, stereochemically, B¹—R¹ is D, L, or a mixture thereof and CH—R² and CH—R² and CH—R³ are independently L or a mixture of D and L.

15. The method of claim 14 wherein P is

R⁷—R⁶ where R⁶ is

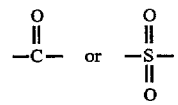

and R⁷ is alkyl, aryl, alkaryl, aralkyl, alkoxy, alkaryloxy, aralkoxy or a heterocyclic moiety.

16. The method of claim 15 wherein X¹ and X² are

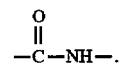

17. The method of claim 16 wherein A is 1 or 2 and B¹ is

18. The method of claim 17 wherein R³ is isobutyl.

19. The method of claim 17 wherein R¹ at each occurrence and R² are independently selected from the group consisting of alkyl and —CH₂—R⁴, where R⁴ is cyclohexyl or naphthyl.

20. The method of claim 19 wherein B¹—R¹, CH—R², and CH—R³ are all of the L-configuration.

21. The method of claim 14 wherein the proteasome inhibitor is selected from the group consisting of:

Ac—Leu—Leu—Nle—H

Z—Leu—Leu—Val—H

Z—Leu—Leu—Nle—H

Z—Leu—Leu—Phe—H

Z—Leu—Leu-2-Nal—H

Z—Leu—Leu—Gly—H

Z—Leu—Leu—Ala—H

-continued

Z—Leu—Leu—Abu—H

Z—Leu—Leu—Nva—H

Z—Leu—Leu—Tyr—H

Z—Leu—Leu—Leu—H

Z—Leu—Leu—Ile—H

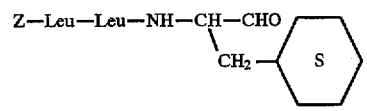

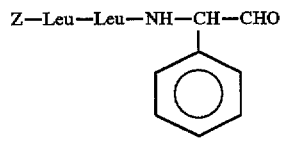

Z—Leu—Leu—Trp—H

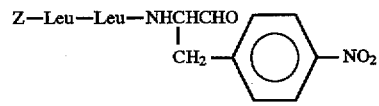

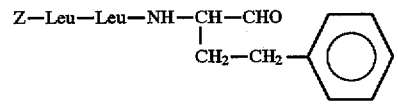

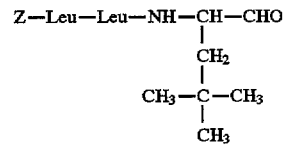

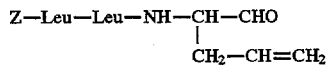

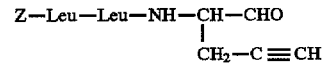

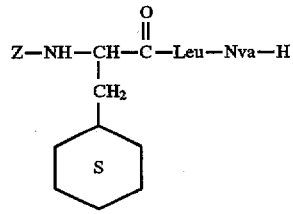

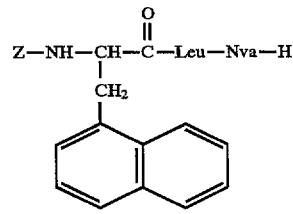

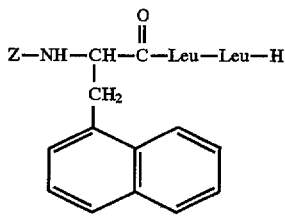
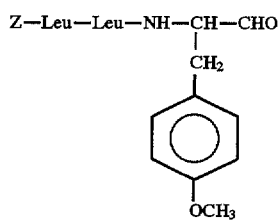
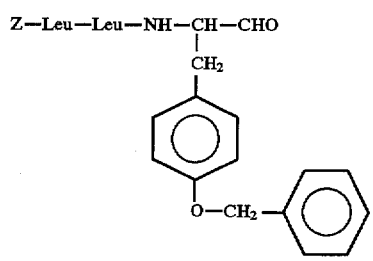
Ac—Leu—Leu—Leu—H
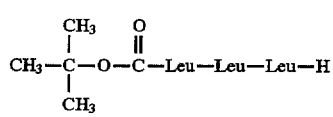
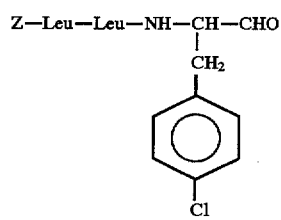
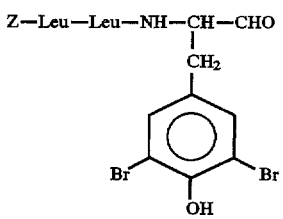
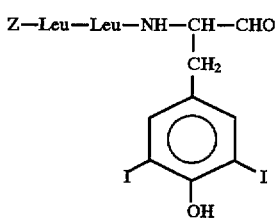
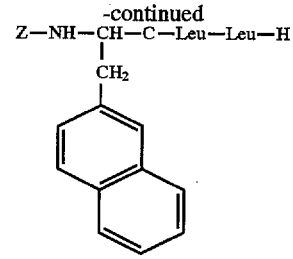
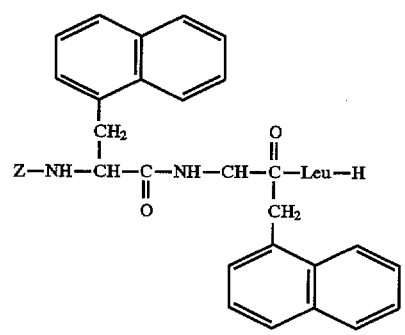
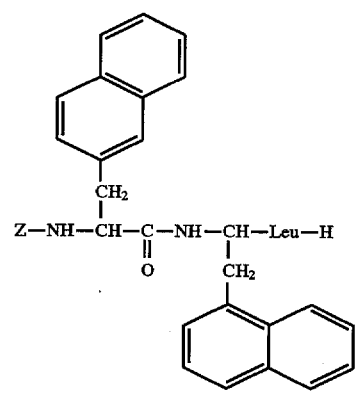
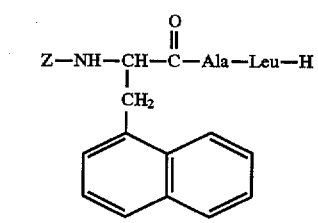
Z—Pro—Ala—Leu—H
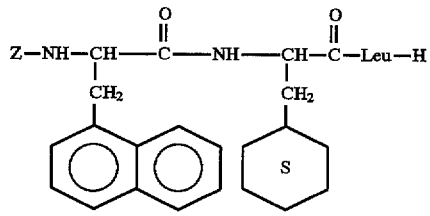
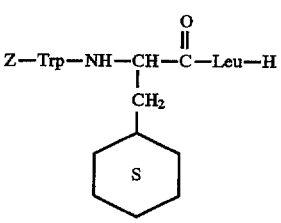

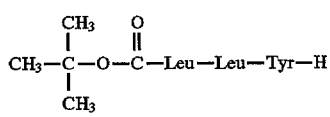
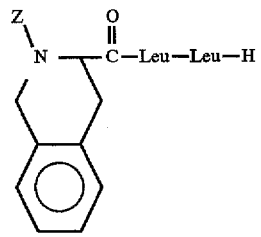
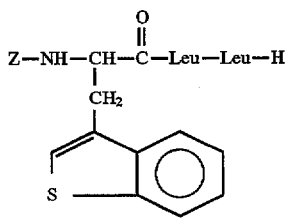
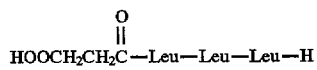
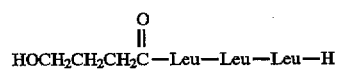
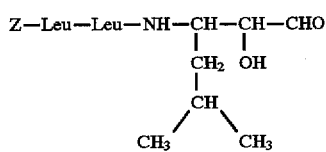
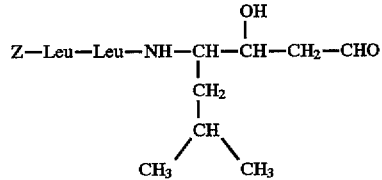
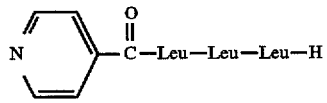
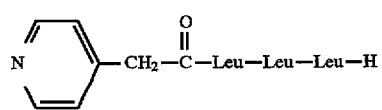
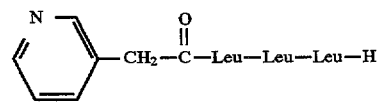
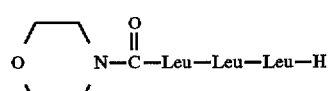
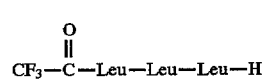
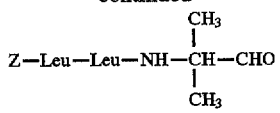
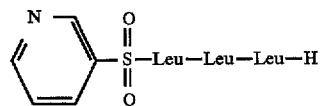
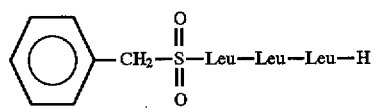
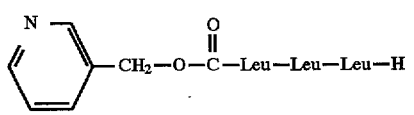
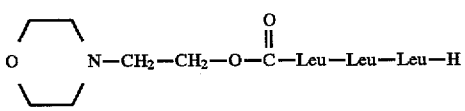
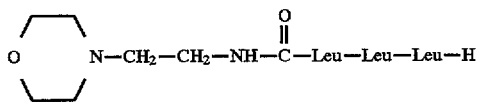
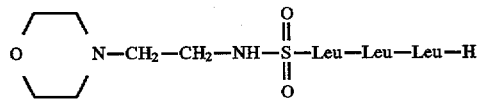
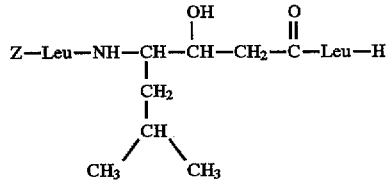
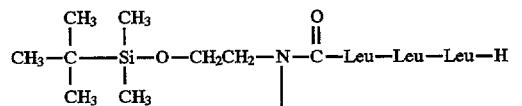
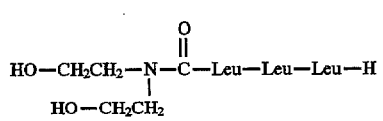
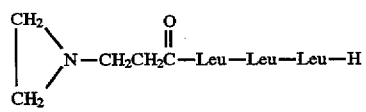

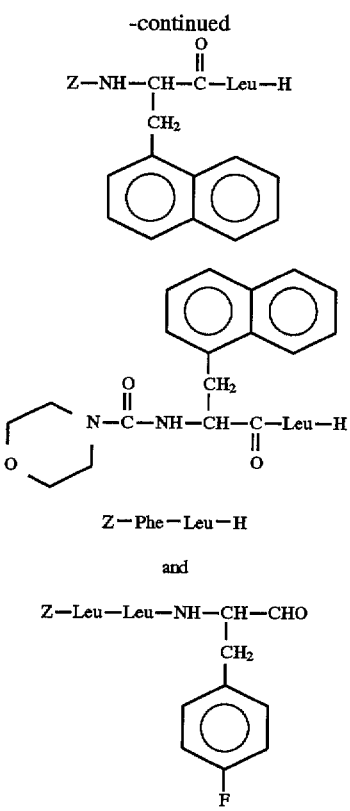
where:
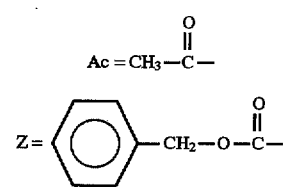
Nle = Norleucine
Nva = Norvaline
Nal = Naphthylalanine
22. The method of claim 14 wherein the proteasome inhibitor is selected from the group consisting of
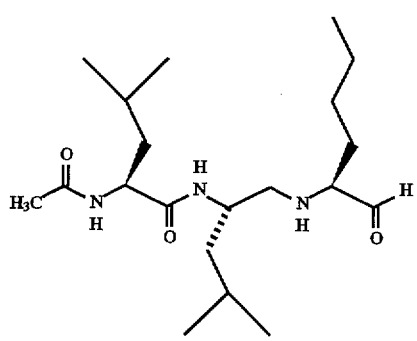
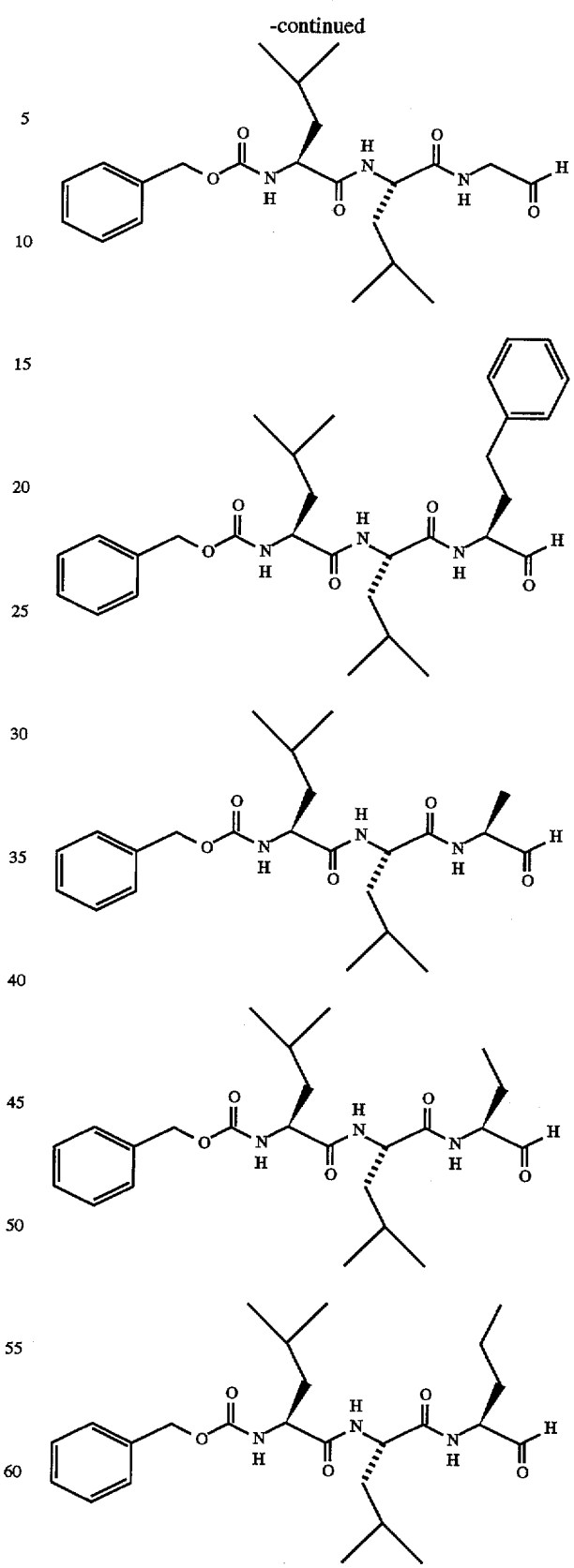

145
-continued
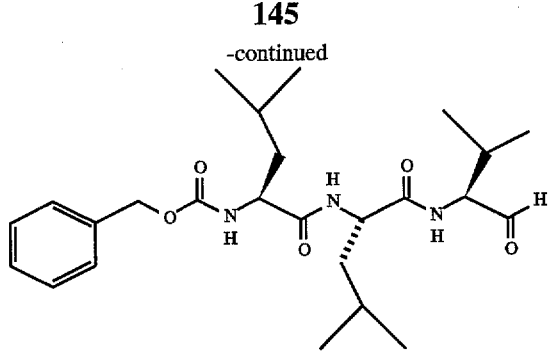
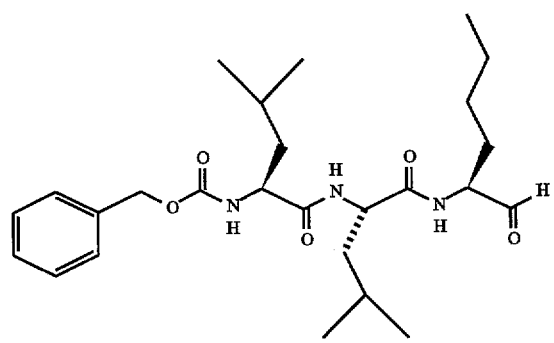
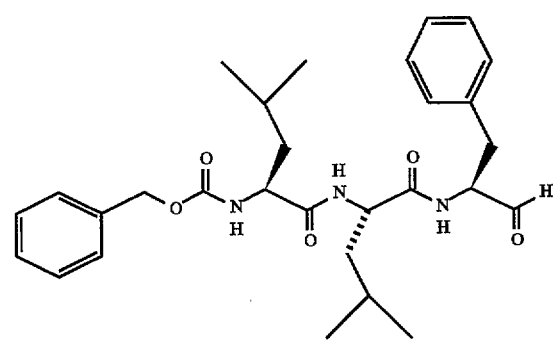
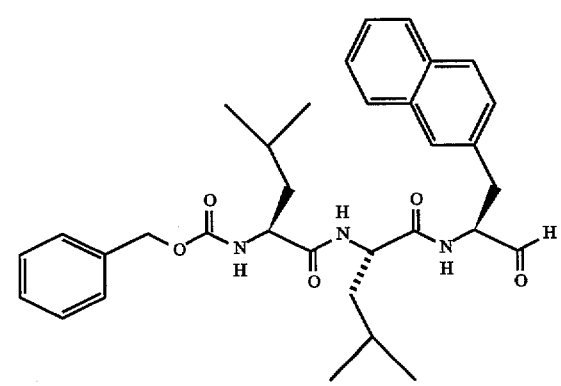
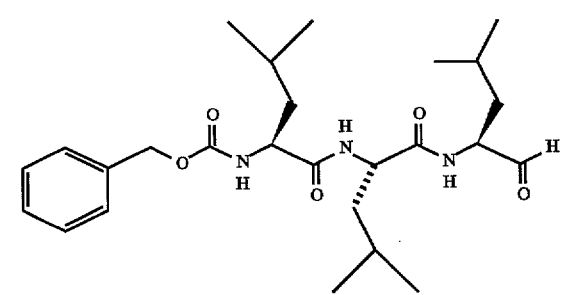
146
-continued
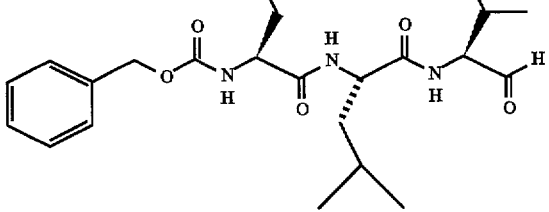
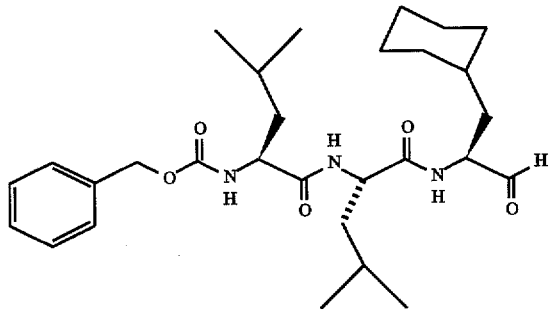
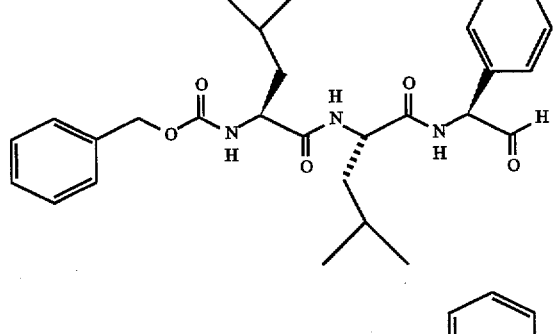
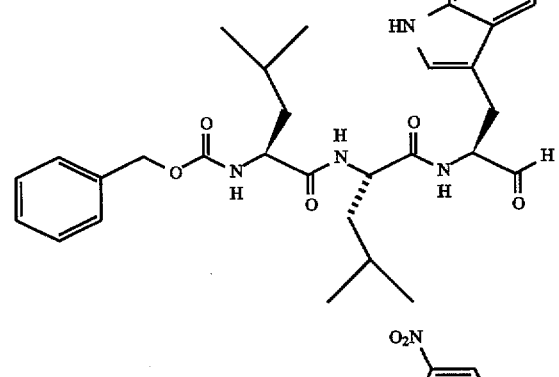
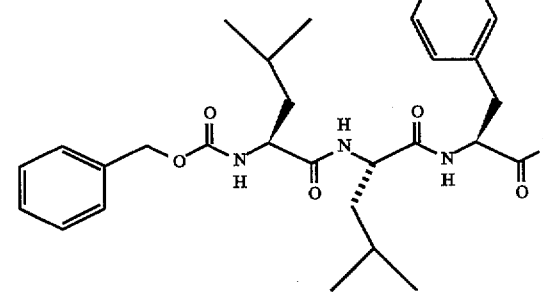

147
-continued
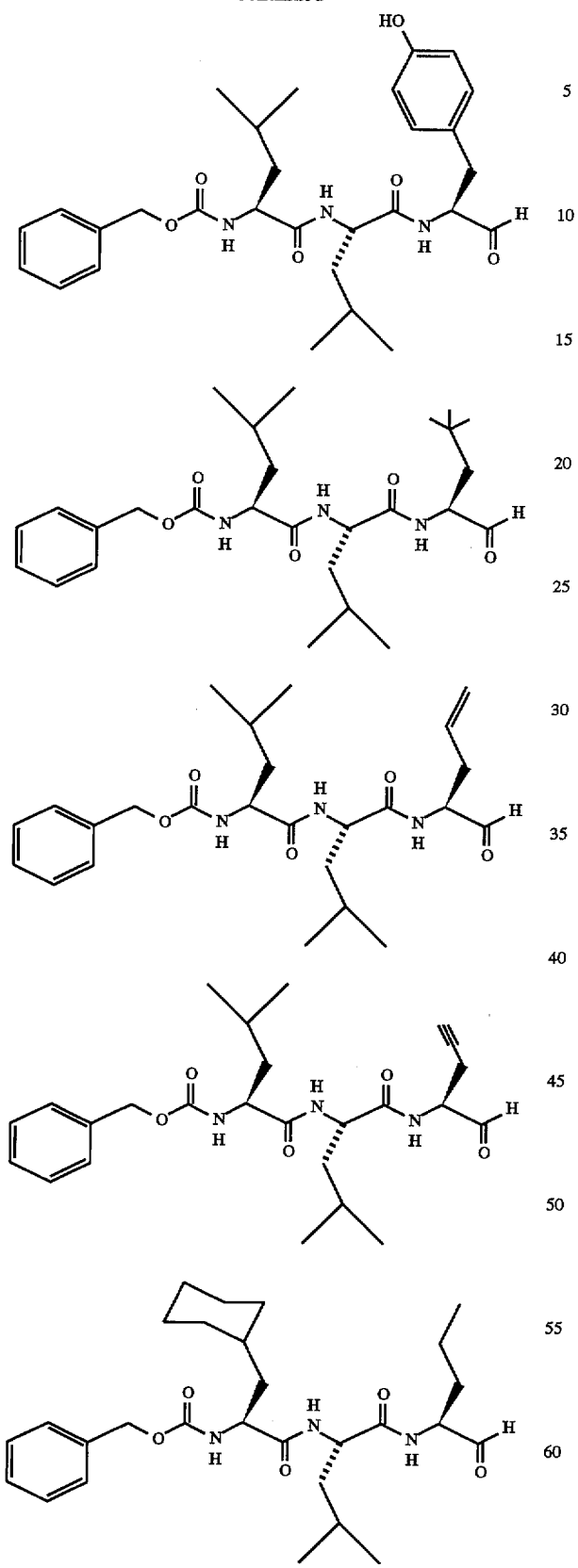
148
-continued
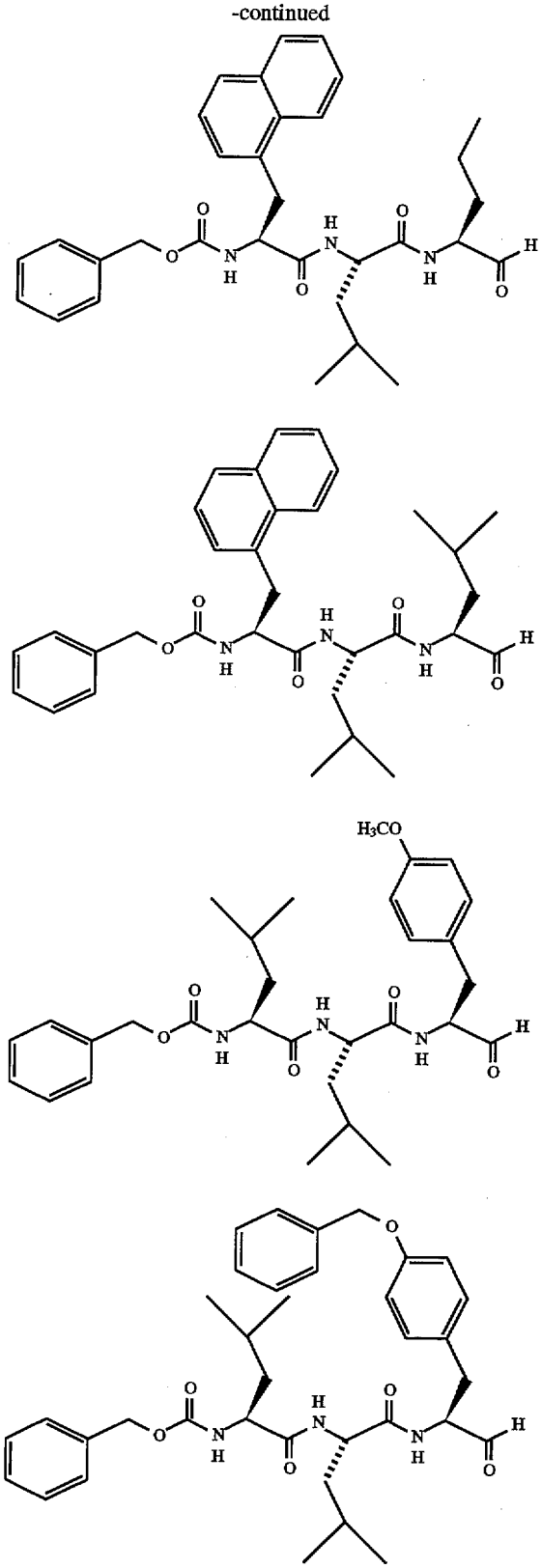

149
-continued
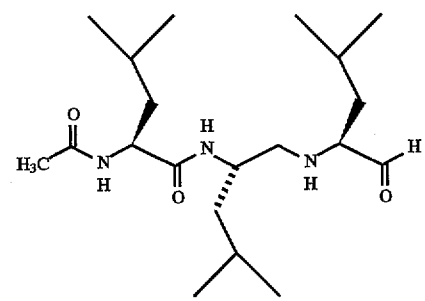
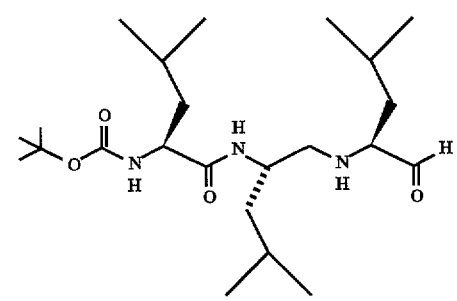
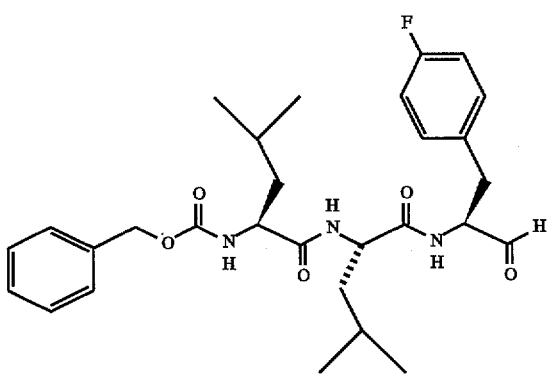
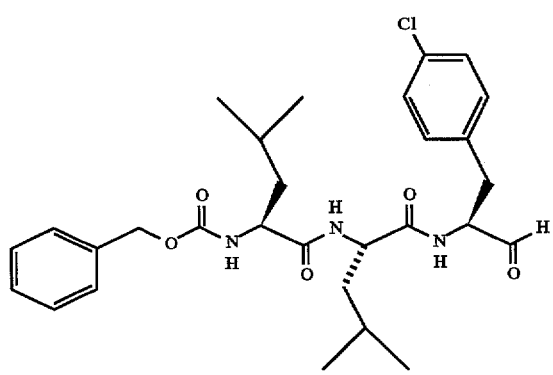
150
-continued
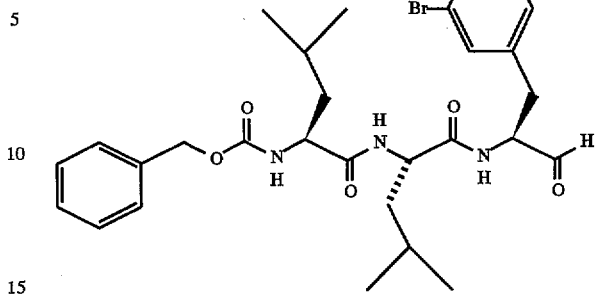
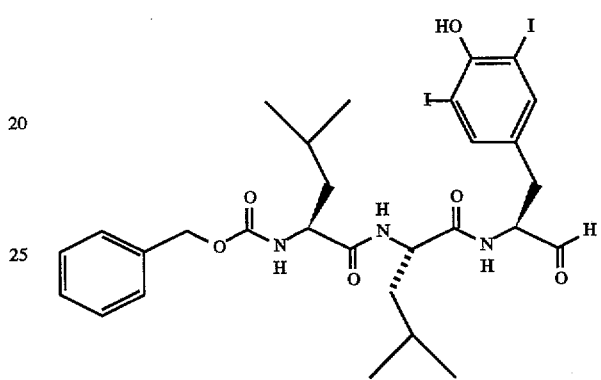
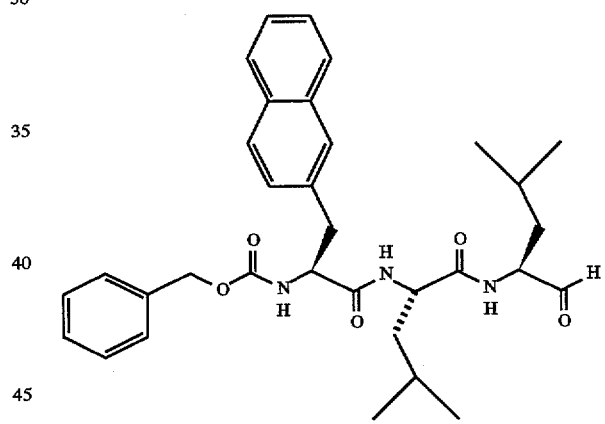
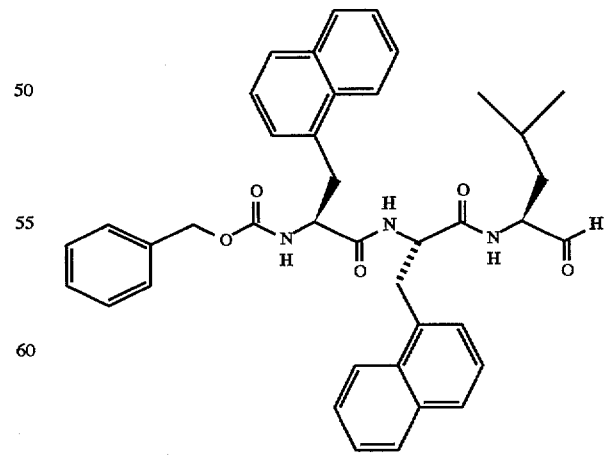

151
-continued
152
-continued
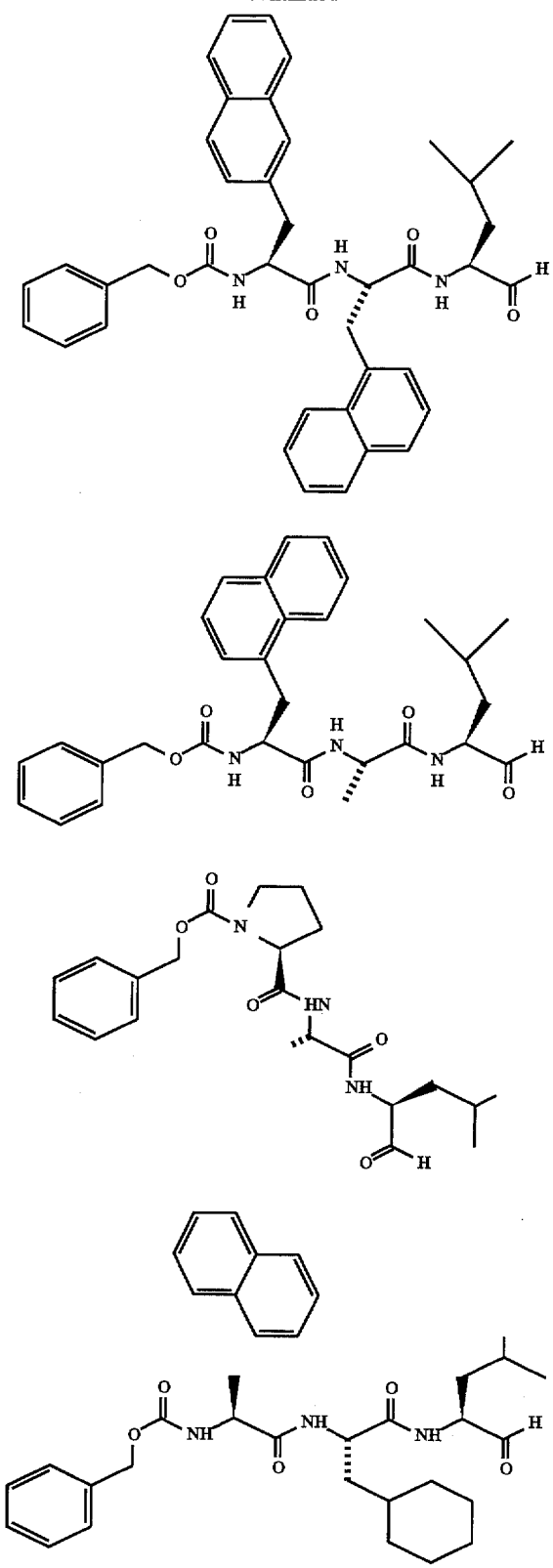
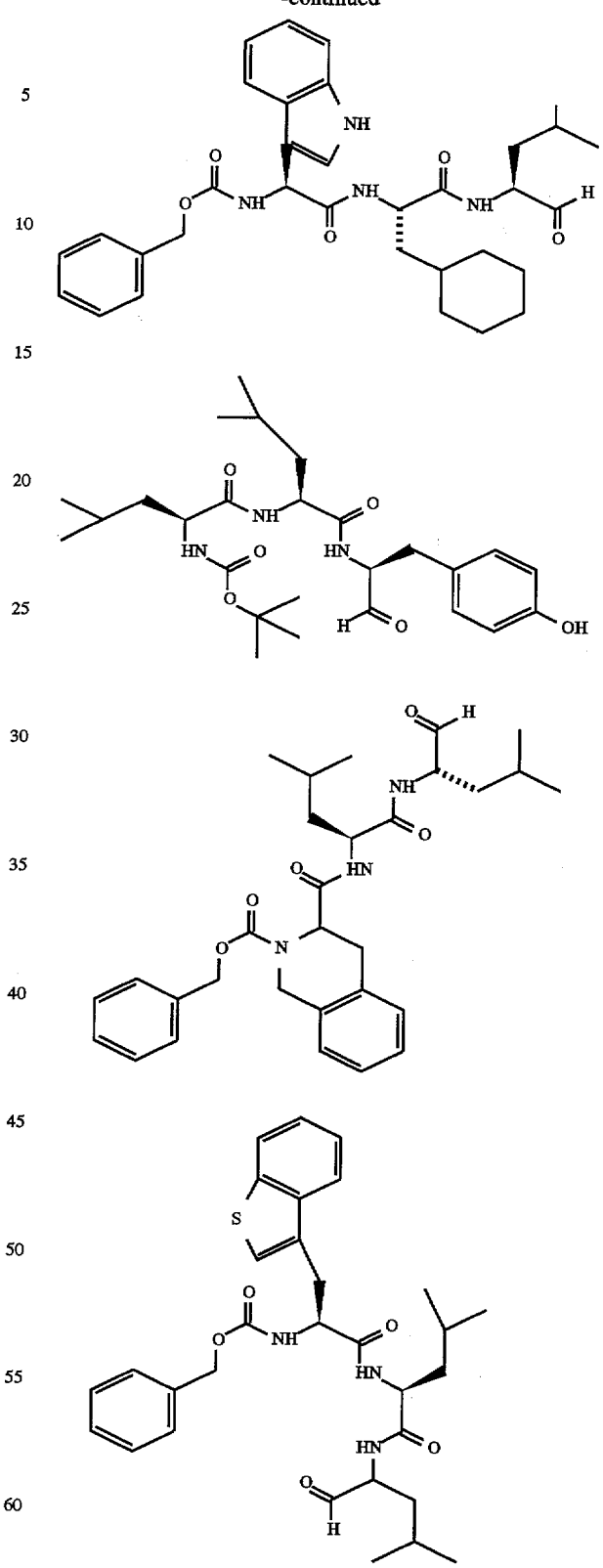

153
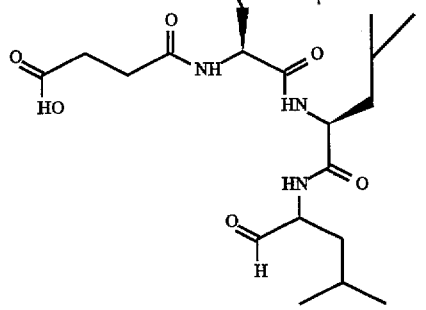
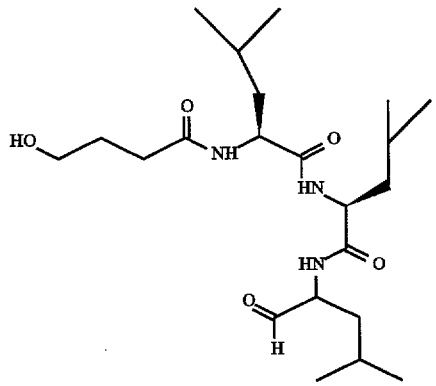
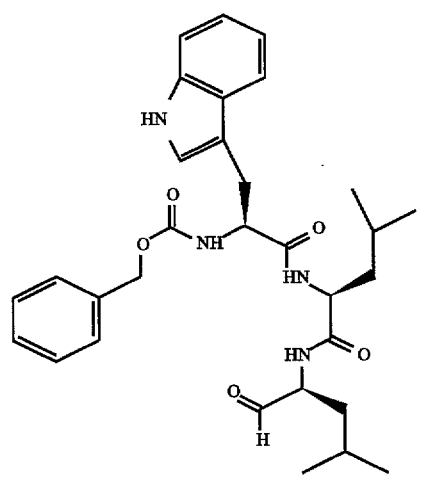
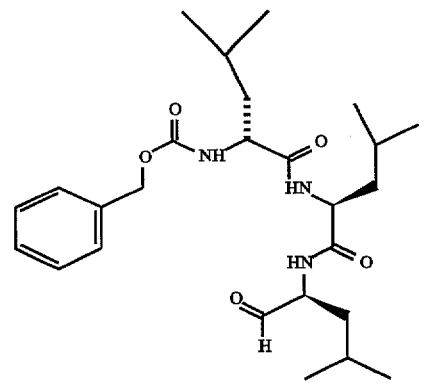
154
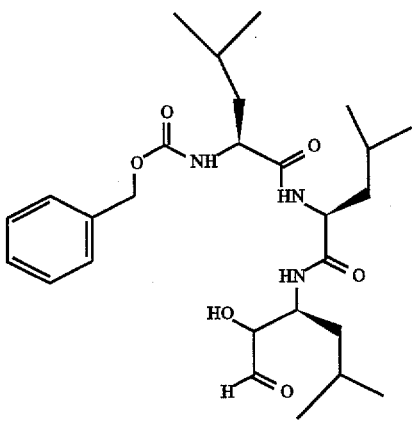
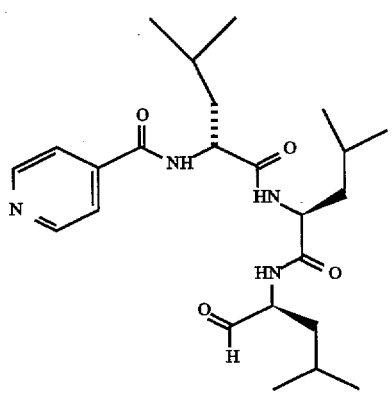
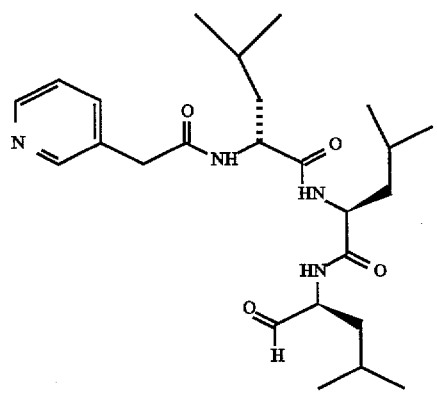
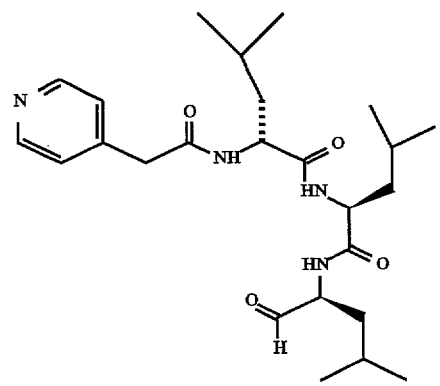

155
-continued
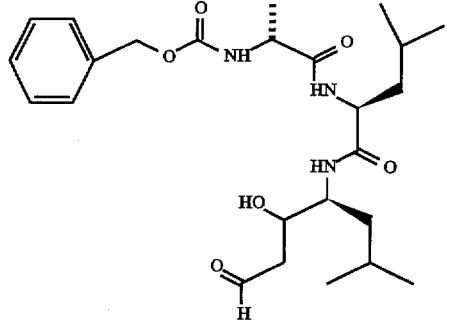
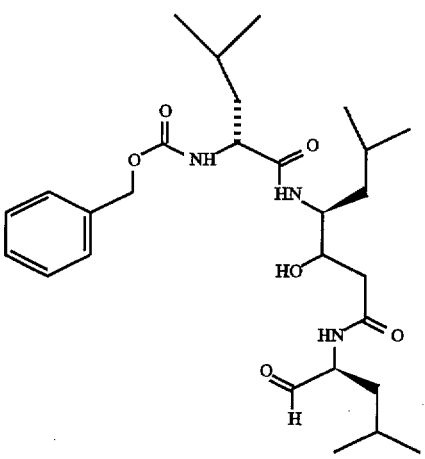
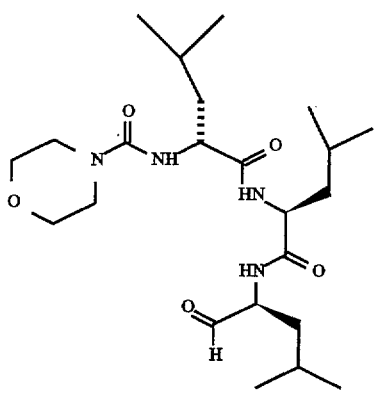
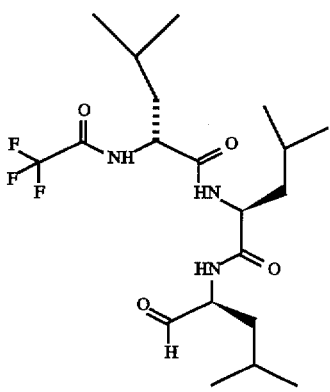
156
-continued
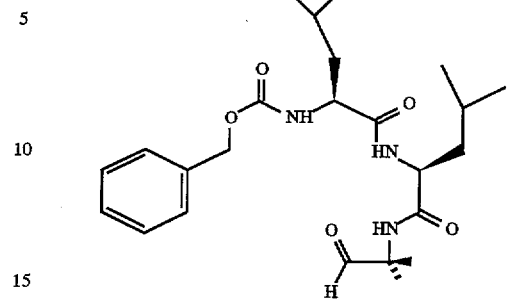
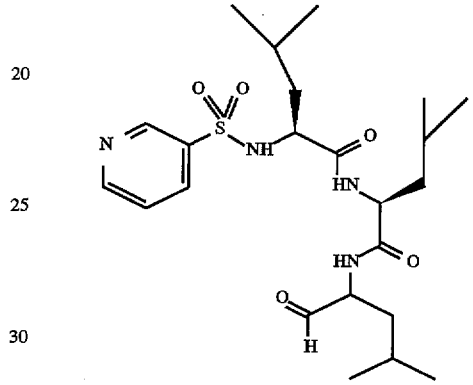
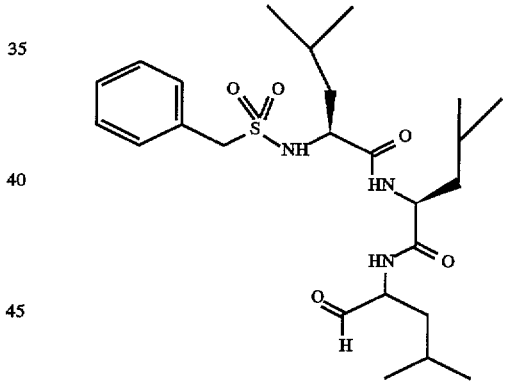
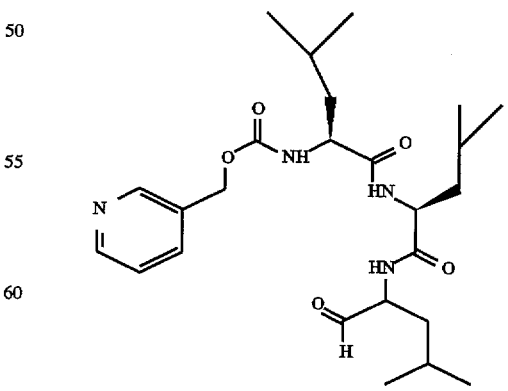

157
-continued
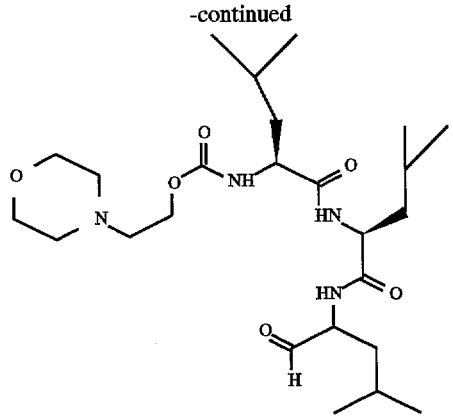
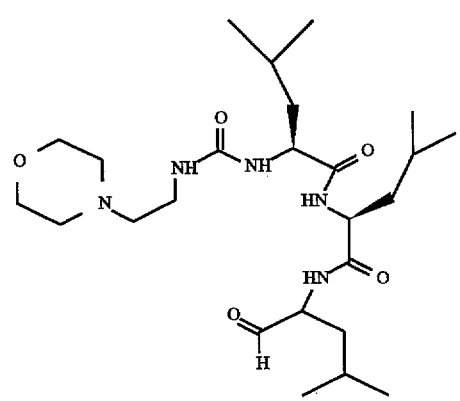
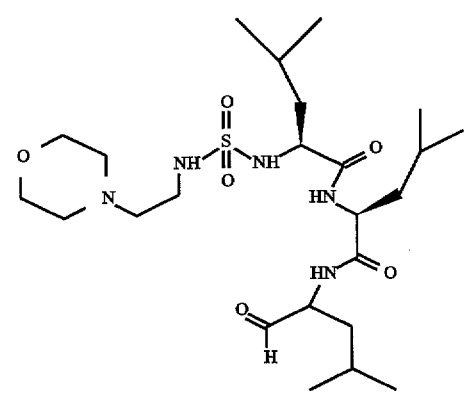
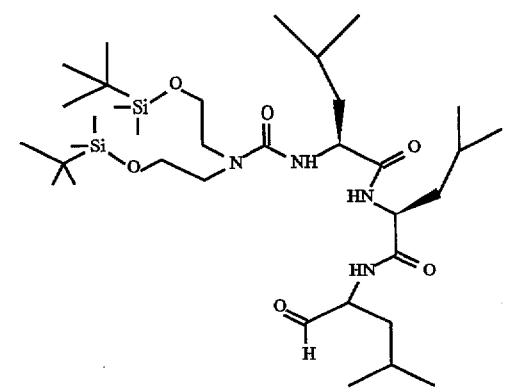
158
-continued
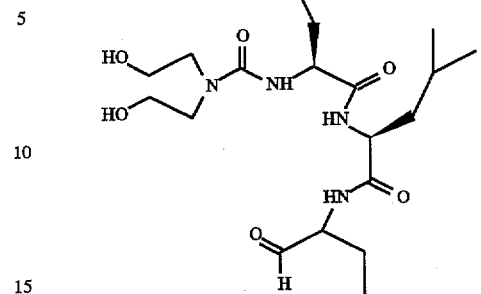
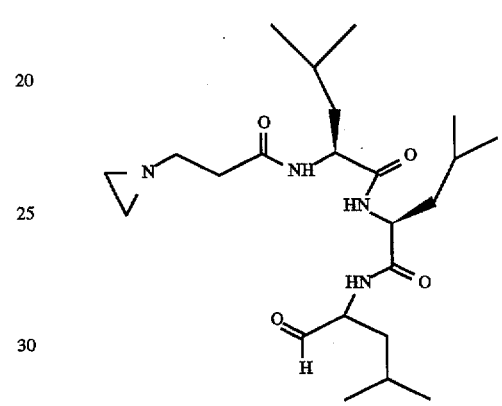
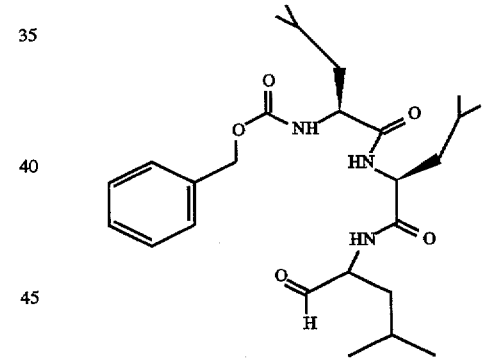
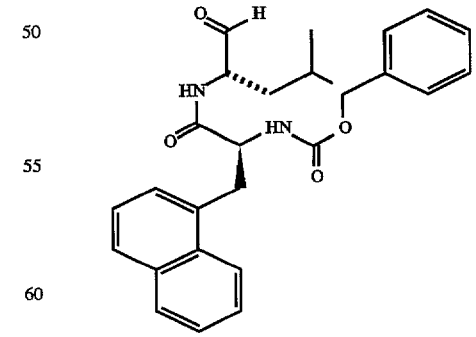

159
-continued
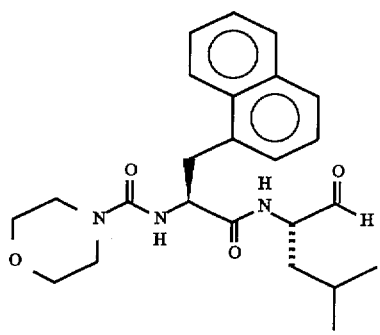
and
160
-continued
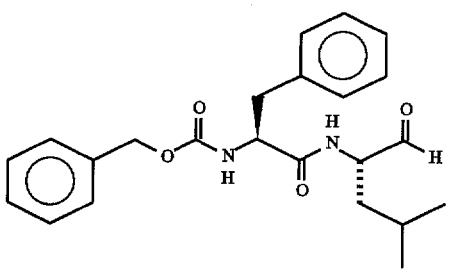
* * * * *